(12) United States Patent
Saadat et al.

(10) Patent No.: US 8,216,253 B2
(45) Date of Patent: Jul. 10, 2012

(54) APPARATUS FOR MANIPULATING AND SECURING TISSUE

(75) Inventors: Vahid Saadat, Saratoga, CA (US); Richard C. Ewers, Fullerton, CA (US); Cang C. Lam, Irvine, CA (US); Robert A. Vaughan, Laguna Niguel, CA (US); Chris Rothe, San Mateo, CA (US); Kenneth J. Michlitsch, Livermore, CA (US)

(73) Assignee: USGI Medical, Inc., San Clemente, CA (US)

( * ) Notice: Subject to any disclaimer, the term of this patent is extended or adjusted under 35 U.S.C. 154(b) by 1114 days.

(21) Appl. No.: 12/107,701

(22) Filed: Apr. 22, 2008

(65) Prior Publication Data

US 2008/0200930 A1 Aug. 21, 2008

Related U.S. Application Data

(63) Continuation of application No. 10/954,666, filed on Sep. 29, 2004, now Pat. No. 7,361,180, which is a continuation-in-part of application No. 10/840,950, filed on May 7, 2004.

(51) Int. Cl.
  *A61B 17/00* (2006.01)
  *A61B 17/10* (2006.01)
(52) U.S. Cl. ........ 606/139; 606/153; 606/142; 606/205; 606/207
(58) Field of Classification Search .................. 606/144, 606/153, 205–207
See application file for complete search history.

(56) References Cited

U.S. PATENT DOCUMENTS

| | | |
|---|---|---|
| 2,201,610 A | 5/1940 | Dawson, Jr. |
| 2,413,142 A | 12/1945 | Jones et al. |
| 3,150,379 A | 9/1964 | Brown |
| 3,166,072 A | 1/1965 | Sullivan, Jr. |
| 3,494,006 A | 2/1970 | Brumlik |
| 3,551,987 A | 1/1971 | Wilkinson |
| 3,646,615 A | 3/1972 | Ness |

(Continued)

FOREIGN PATENT DOCUMENTS

EP 0480428 A2 4/1992

(Continued)

OTHER PUBLICATIONS

AngioLINK, The Expanding Vascular Staple [brochure] 1, page total.

(Continued)

*Primary Examiner* — Gary Jackson
*Assistant Examiner* — Diane Yabut
(74) *Attorney, Agent, or Firm* — Kenneth H. Ohriner; Perkins Coie LLP

(57) ABSTRACT

Apparatus for manipulating and securing tissue are described herein. In creating tissue folds within the body of a patient, a tissue manipulation assembly may generally have an elongate tubular member, an engagement member slidably disposed through the tubular member and a distal end adapted to engage tissue via a helical member, tissue stabilizing members positioned at the tubular member distal end which are adapted to stabilize tissue therebetween, and a delivery tube pivotable about the tissue stabilizer. The stabilizing members can be adapted to become angled relative to a longitudinal axis of the elongate tubular member. Moreover, one or all the articulation controls and functions can be integrated into a singular handle assembly connectable to the tissue manipulation assembly via a rigid or flexible tubular body.

29 Claims, 64 Drawing Sheets

U.S. PATENT DOCUMENTS

| | | |
|---|---|---|
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |
| 4,006,747 A | 2/1977 | Kronenthal et al. |
| 4,007,743 A | 2/1977 | Blake |
| 4,060,089 A | 11/1977 | Noiles |
| 4,069,825 A | 1/1978 | Akiyama |
| 4,235,238 A | 11/1980 | Ogiu et al. |
| 4,245,624 A | 1/1981 | Komiya |
| 4,367,746 A | 1/1983 | Derechinsky |
| 4,414,720 A | 11/1983 | Crooms |
| 4,462,402 A | 7/1984 | Burgio et al. |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kuzmak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsch et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,254,126 A | 10/1993 | Filipi et al. |
| 5,261,916 A | 11/1993 | Engelson |
| 5,268,001 A | 12/1993 | Nicholson et al. |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,342,376 A | 8/1994 | Ruff |
| 5,345,949 A | 9/1994 | Shlain |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,662 A | 9/1997 | Bishop et al. |
| 5,662,663 A | 9/1997 | Shallman |
| 5,665,109 A | 9/1997 | Yoon |
| 5,665,112 A | 9/1997 | Thal |
| 5,667,513 A | 9/1997 | Torrie et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,421 A | 12/1997 | Schneidt |

| | | | | | | |
|---|---|---|---|---|---|---|
| 5,707,394 A | 1/1998 | Miller et al. | | 6,077,281 A | 6/2000 | Das |
| 5,709,708 A | 1/1998 | Thal | | 6,077,291 A | 6/2000 | Das |
| 5,713,903 A | 2/1998 | Sander et al. | | 6,079,414 A | 6/2000 | Roth |
| 5,720,765 A | 2/1998 | Thal | | 6,086,600 A | 7/2000 | Kortenbach |
| 5,724,978 A | 3/1998 | Tenhoff | | 6,086,601 A | 7/2000 | Yoon |
| 5,725,552 A | 3/1998 | Kotula et al. | | 6,110,183 A | 8/2000 | Cope |
| 5,732,707 A | 3/1998 | Widder et al. | | 6,113,609 A * | 9/2000 | Adams .................... 606/139 |
| 5,741,297 A | 4/1998 | Simon | | 6,113,611 A | 9/2000 | Allen et al. |
| 5,749,893 A | 5/1998 | Vidal et al. | | 6,119,913 A | 9/2000 | Adams et al. |
| 5,752,963 A | 5/1998 | Allard et al. | | 6,149,658 A | 11/2000 | Gardiner et al. |
| 5,766,189 A | 6/1998 | Matsuno | | 6,152,935 A | 11/2000 | Kammerer et al. |
| 5,779,719 A | 7/1998 | Klein et al. | | 6,159,146 A | 12/2000 | El Gazayerli |
| 5,782,859 A | 7/1998 | Nicholas et al. | | 6,162,168 A | 12/2000 | Schweich, Jr. et al. |
| 5,782,865 A | 7/1998 | Grotz | | 6,165,119 A | 12/2000 | Schweich, Jr. et al. |
| 5,787,897 A | 8/1998 | Kieturakis | | 6,165,120 A | 12/2000 | Schweich, Jr. et al. |
| 5,792,152 A | 8/1998 | Klein et al. | | 6,167,889 B1 | 1/2001 | Benetti |
| 5,792,153 A | 8/1998 | Swain et al. | | 6,171,320 B1 | 1/2001 | Monassevitch |
| 5,797,929 A | 8/1998 | Andreas et al. | | 6,174,323 B1 | 1/2001 | Biggs et al. |
| 5,797,960 A | 8/1998 | Stevens et al. | | 6,179,195 B1 | 1/2001 | Adams et al. |
| 5,810,849 A | 9/1998 | Kontos | | 6,183,411 B1 | 2/2001 | Mortier et al. |
| 5,810,851 A | 9/1998 | Yoon | | RE37,117 E | 3/2001 | Palermo |
| 5,810,853 A | 9/1998 | Yoon | | 6,197,022 B1 | 3/2001 | Baker |
| 5,814,070 A | 9/1998 | Borzone et al. | | 6,214,007 B1 | 4/2001 | Anderson |
| 5,817,110 A | 10/1998 | Kronner | | 6,231,561 B1 | 5/2001 | Frazier et al. |
| 5,823,956 A | 10/1998 | Roth et al. | | 6,245,079 B1 | 6/2001 | Nobles et al. |
| 5,824,011 A | 10/1998 | Stone et al. | | 6,260,552 B1 | 7/2001 | Mortier et al. |
| 5,827,298 A | 10/1998 | Hart et al. | | 6,261,222 B1 | 7/2001 | Schweich, Jr. et al. |
| 5,829,447 A | 11/1998 | Stevens et al. | | 6,264,602 B1 | 7/2001 | Mortier et al. |
| 5,836,955 A | 11/1998 | Buelna et al. | | 6,270,515 B1 | 8/2001 | Linden et al. |
| 5,840,078 A | 11/1998 | Yerys | | 6,283,973 B1 | 9/2001 | Hubbard et al. |
| 5,843,084 A | 12/1998 | Hart et al. | | 6,290,674 B1 | 9/2001 | Roue et al. |
| 5,843,126 A | 12/1998 | Jameel | | 6,293,956 B1 | 9/2001 | Crainich et al. |
| 5,846,261 A | 12/1998 | Kotula et al. | | 6,296,656 B1 | 10/2001 | Bolduc et al. |
| 5,855,614 A | 1/1999 | Stevens et al. | | 6,306,159 B1 | 10/2001 | Schwartz et al. |
| 5,860,991 A | 1/1999 | Klein et al. | | 6,312,437 B1 | 11/2001 | Kortenbach |
| 5,861,003 A | 1/1999 | Latson et al. | | 6,315,789 B1 | 11/2001 | Cragg |
| 5,865,791 A * | 2/1999 | Whayne et al. ............... 604/500 | | 6,322,563 B1 | 11/2001 | Cummings et al. |
| 5,868,762 A | 2/1999 | Cragg et al. | | 6,322,580 B1 | 11/2001 | Kanner |
| 5,879,371 A | 3/1999 | Gardiner et al. | | 6,332,468 B1 | 12/2001 | Benetti |
| 5,887,594 A | 3/1999 | LoCicero, III | | 6,332,863 B1 | 12/2001 | Schweich, Jr. et al. |
| 5,888,247 A | 3/1999 | Benetti | | 6,332,864 B1 | 12/2001 | Schweich, Jr. et al. |
| 5,891,168 A | 4/1999 | Thal | | 6,332,893 B1 | 12/2001 | Mortier et al. |
| 5,893,856 A | 4/1999 | Jacob et al. | | 6,336,940 B1 | 1/2002 | Graf et al. |
| 5,895,404 A | 4/1999 | Ruiz | | 6,346,074 B1 | 2/2002 | Roth |
| 5,897,562 A | 4/1999 | Bolanos et al. | | 6,348,064 B1 | 2/2002 | Kanner |
| 5,899,920 A | 5/1999 | DeSatnick et al. | | 6,355,052 B1 | 3/2002 | Neuss et al. |
| 5,899,921 A | 5/1999 | Caspari et al. | | 6,358,197 B1 | 3/2002 | Silverman et al. |
| 5,901,895 A | 5/1999 | Heaton et al. | | 6,363,938 B2 | 4/2002 | Saadat et al. |
| 5,916,224 A | 6/1999 | Esplin | | 6,368,339 B1 | 4/2002 | Amplatz |
| 5,925,059 A | 7/1999 | Palermo et al. | | 6,387,104 B1 | 5/2002 | Pugsley, Jr. et al. |
| 5,928,264 A | 7/1999 | Sugarbaker et al. | | 6,402,679 B1 | 6/2002 | Mortier et al. |
| 5,944,738 A | 8/1999 | Amplatz et al. | | 6,402,680 B2 | 6/2002 | Mortier et al. |
| 5,947,983 A | 9/1999 | Solar et al. | | 6,406,420 B1 | 6/2002 | McCarthy et al. |
| 5,947,997 A | 9/1999 | Pavcnik et al. | | H2037 H | 7/2002 | Yates et al. |
| 5,948,001 A | 9/1999 | Larsen | | 6,423,087 B1 | 7/2002 | Sawada |
| 5,954,731 A | 9/1999 | Yoon | | 6,425,911 B1 | 7/2002 | Akerfeldt et al. |
| 5,954,732 A | 9/1999 | Hart et al. | | 6,447,533 B1 | 9/2002 | Adams |
| 5,961,440 A | 10/1999 | Schweich, Jr. et al. | | 6,494,888 B1 | 12/2002 | Laufer et al. |
| 5,964,765 A | 10/1999 | Fenton, Jr. et al. | | 6,506,196 B1 | 1/2003 | Laufer |
| 5,964,782 A | 10/1999 | Lafontaine et al. | | 6,517,552 B1 | 2/2003 | Nord et al. |
| 5,964,783 A | 10/1999 | Grafton et al. | | 6,533,796 B1 | 3/2003 | Sauer et al. |
| 5,976,127 A | 11/1999 | Lax | | 6,537,285 B1 | 3/2003 | Hatasaka, Jr. et al. |
| 5,976,158 A | 11/1999 | Adams et al. | | 6,554,845 B1 | 4/2003 | Fleenor et al. |
| 5,976,159 A | 11/1999 | Bolduc et al. | | 6,558,400 B2 | 5/2003 | Deem et al. |
| 5,980,558 A | 11/1999 | Wiley | | 6,572,629 B2 | 6/2003 | Kalloo et al. |
| 5,984,933 A | 11/1999 | Yoon | | 6,641,592 B1 | 11/2003 | Sauer et al. |
| 5,993,476 A | 11/1999 | Groiso | | 6,656,194 B1 | 12/2003 | Gannoe et al. |
| 6,013,083 A | 1/2000 | Bennett | | 6,663,639 B1 | 12/2003 | Laufer et al. |
| 6,017,358 A | 1/2000 | Yoon et al. | | 6,692,506 B1 | 2/2004 | Ory et al. |
| 6,027,523 A | 2/2000 | Schmieding | | 6,695,764 B2 | 2/2004 | Silverman et al. |
| 6,033,430 A | 3/2000 | Bonutti | | 6,716,232 B1 | 4/2004 | Vidal et al. |
| 6,045,497 A | 4/2000 | Schweich, Jr. et al. | | 6,719,763 B2 | 4/2004 | Chung et al. |
| 6,045,573 A | 4/2000 | Wenstrom, Jr. et al. | | 6,719,764 B1 | 4/2004 | Gellman et al. |
| 6,050,936 A | 4/2000 | Schweich, Jr. et al. | | 6,736,828 B1 | 5/2004 | Adams et al. |
| 6,053,935 A | 4/2000 | Brenneman et al. | | 6,746,460 B2 | 6/2004 | Gannoe et al. |
| 6,059,715 A | 5/2000 | Schweich, Jr. et al. | | 6,755,843 B2 | 6/2004 | Chung et al. |
| 6,059,719 A | 5/2000 | Yamamoto et al. | | 6,773,440 B2 | 8/2004 | Gannoe et al. |
| 6,074,401 A | 6/2000 | Gardiner et al. | | 6,773,441 B1 | 8/2004 | Laufer et al. |
| 6,077,214 A | 6/2000 | Mortier et al. | | 6,821,285 B2 | 11/2004 | Laufer et al. |

| | | |
|---|---|---|
| 6,835,199 B2 | 12/2004 | McGuckin, Jr. et al. |
| 2001/0016675 A1 | 8/2001 | Mortier et al. |
| 2001/0025171 A1 | 9/2001 | Mortier et al. |
| 2001/0049509 A1 | 12/2001 | Sekine et al. |
| 2001/0051815 A1 | 12/2001 | Esplin |
| 2001/0056282 A1 | 12/2001 | Sonnenschein et al. |
| 2002/0010490 A1 | 1/2002 | Schaller et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 * | 4/2002 | Laufer et al. .................. 606/153 |
| 2002/0055757 A1 | 5/2002 | Torre et al. |
| 2002/0058855 A1 | 5/2002 | Schweich et al. |
| 2002/0065534 A1 | 5/2002 | Hermann et al. |
| 2002/0068849 A1 | 6/2002 | Schweich et al. |
| 2002/0068945 A1 | 6/2002 | Sixto et al. |
| 2002/0072761 A1 | 6/2002 | Abrams et al. |
| 2002/0077524 A1 | 6/2002 | Schweich et al. |
| 2002/0078967 A1 | 6/2002 | Sixto et al. |
| 2002/0082621 A1 | 6/2002 | Schurr et al. |
| 2002/0082622 A1 | 6/2002 | Kane |
| 2002/0107530 A1 | 8/2002 | Sauer et al. |
| 2002/0156344 A1 | 10/2002 | Pasricha et al. |
| 2002/0183768 A1 | 12/2002 | Deem et al. |
| 2002/0193816 A1 | 12/2002 | Laufer et al. |
| 2003/0009085 A1 | 1/2003 | Arai et al. |
| 2003/0055442 A1 | 3/2003 | Laufer et al. |
| 2003/0065359 A1 | 4/2003 | Weller et al. |
| 2003/0109892 A1 | 6/2003 | Deem et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236536 A1 | 12/2003 | Grigoryants et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0122452 A1 | 6/2004 | Deem et al. |
| 2004/0122453 A1 | 6/2004 | Deem et al. |
| 2004/0122474 A1 | 6/2004 | Gellman et al. |
| 2004/0138682 A1 | 7/2004 | Onuki et al. |
| 2004/0147941 A1 | 7/2004 | Takemoto et al. |
| 2004/0176784 A1 | 9/2004 | Okada |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0215216 A1 | 10/2004 | Gannoe et al. |
| 2004/0243152 A1 | 12/2004 | Taylor et al. |
| 2004/0249362 A1 | 12/2004 | Levine et al. |
| 2004/0249392 A1 | 12/2004 | Mikkaichi et al. |
| 2004/0249395 A1 | 12/2004 | Mikkaichi et al. |
| 2005/0033320 A1 | 2/2005 | McGuckin et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0075654 A1 | 4/2005 | Kelleher |

FOREIGN PATENT DOCUMENTS

| | | |
|---|---|---|
| EP | 0847727 A1 | 6/1998 |
| EP | 1031321 A1 | 8/2000 |
| FR | 2768324 A1 | 3/1999 |
| GB | 2165559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/075787 A1 | 9/2004 |
| WO | WO 2004/103189 A1 | 12/2004 |
| WO | WO 2005/004727 A1 | 1/2005 |

OTHER PUBLICATIONS

Bluett et al.. "Experimental Evaluation of Staple Lines in Gastric Surgery." *Arch. Surg.*. vol. 122, Jul. 1987. pp. 772-776.

Brolin et al., "Experimental Evaluation of Techniques of Gastric Paritioning for Morbid Obesity," *Surgery, Gynecology & Obstetrics*. vol. 153, Dec. 1981. pp. 878-882.

Chuttani, Ram et al. "A Novel Endoscopic Full-Thickness Plicator for Treatment of DERD: An Animal Model Study." *Gastointestinal Endoscopy*, 2002: vol. 56, pp. 116-122.

Johnston et al. "The Magenstrasse and Mill Operation of Morbid Obesity." *Obesity Surgery* 13, 2003. pp. 10-16.

Okudaira et al., "The Healing and Tensile Strength of the Gastroplasty Staple Line," *The American Surgeon*, Oct. 1984, pp. 564-568.

Surgical Dynamics Inc.. The S D sorb Meniscal Stapler [brochure] (1997). 3 pages total.

Sutura. The Next Generation in Vascular Suturing Devices: Superstitch [brochure]. 2 pages total.

* cited by examiner

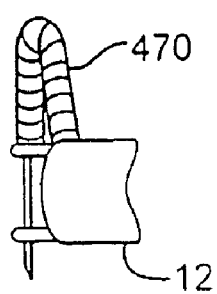
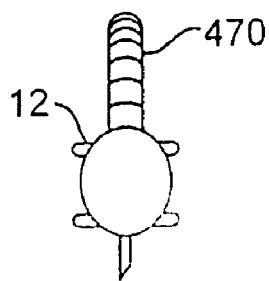
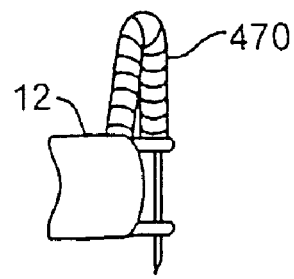
FIG. 35B    FIG. 35A    FIG. 35C
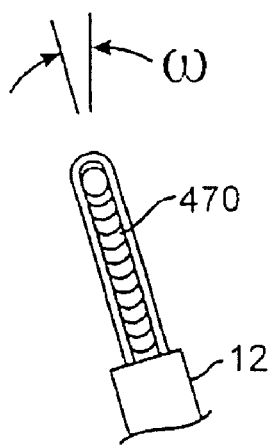
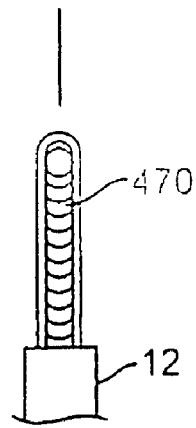
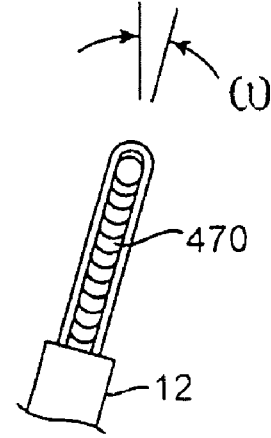
FIG. 36B    FIG. 36A    FIG. 36C
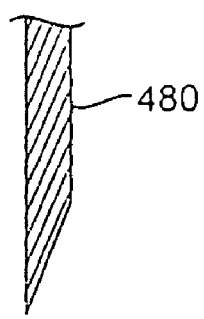
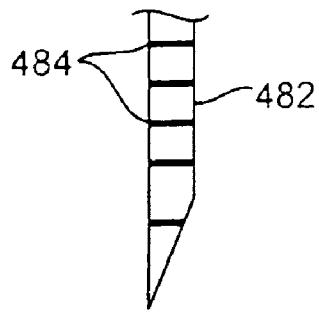
FIG. 37A    FIG. 37B

APPARATUS FOR MANIPULATING AND SECURING TISSUE

CROSS-REFERENCE TO RELATED APPLICATIONS

This application is a continuation of U.S. patent application Ser. No. 10/954,666, filed Sep. 29, 2004, now U.S. Pat. No. 7,361,180, which is a continuation-in-part of U.S. patent application Ser. No. 10/840,950, filed May 7, 2004, and now pending, both incorporated herein by reference.

BACKGROUND OF THE INVENTION

Field of the Invention

The present invention relates to methods and apparatus for forming and securing gastrointestinal ("GI") tissue folds. More particularly, the present invention relates to methods and apparatus for reducing the effective cross-sectional area of a gastrointestinal lumen.

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

A number of surgical techniques have been developed to treat morbid obesity, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in these surgical procedures typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen includes four tissue layers, wherein the mucosa layer is the inner-most tissue layer followed by connective tissue, the muscularis layer and the serosa layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intra-operatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., may of these devices are configured to be placed only after the tissue has been plicated and not during the actual plication procedure.

BRIEF SUMMARY OF THE INVENTION

In creating tissue plications, a tissue plication tool having a distal tip may be advanced (transorally, transgastrically, etc.) into the stomach. The tissue may be engaged or grasped and the engaged tissue may be moved to a proximal position relative to the tip of the device, thereby providing a substantially uniform plication of predetermined size. In order to first create the plication within a body lumen of a patient, various methods and devices may be implemented. The anchoring and securement devices may be delivered and positioned via an endoscopic apparatus that engages a tissue wall of the gastrointestinal lumen, creates one or more tissue folds, and disposes one or more of the anchors through the tissue fold(s). The tissue anchor(s) may be disposed through the muscularis and/or serosa layers of the gastrointestinal lumen.

One variation of an apparatus which may be used to manipulate tissue and create a tissue fold may generally comprise an elongate tubular member having a proximal end, a distal end, and a length therebetween, an engagement member which is slidably disposed through the tubular member and having a distal end adapted to engage tissue, a first stabilizing member and a second stabilizing member positioned at the tubular member distal end and adapted to stabilize tissue therebetween, wherein the first and second stabilizing members are further adapted to be angled relative to a longitudinal axis of the elongate tubular member, and a delivery tube adapted to pivot about the first stabilizing member The elongate tubular member or launch tube may be advanced from its proximal end at a handle located outside a patient's body such that a portion of the launch tube is forced to rotate at a hinge or pivot and reconfigure itself such that the distal portion forms a curved or arcuate shape that positions the launch tube opening perpendicularly relative to a longitudinal axis of body. The launch tube, or at least a portion of the launch tube, is preferably fabricated from a highly flexible material or it may be fabricated, e.g., from Nitinol tubing material which is adapted to flex, e.g., via circumferential slots, to permit bending.

The tissue engagement member may be an elongate member, e.g., a wire, hypotube, etc., which has a tissue grasper or engager attached or integrally formed at its distal end for grasping or engaging the tissue. In one variation, the tissue grasper may be formed as a helix having a uniform outer diameter with a constant pitch. The helix 80 may be attached to an elongate acquisition member via any suitable fastening method, e.g., adhesives, solder, etc. Alternatively, the helix may be integrally formed from the distal portion of the acquisition member by winding or coiling the distal portion in a helix configuration.

Alternative configurations for the helix may include a number of variations. For instance, the helix may have a varied pitch or one or more regions with varying pitch along the length of the helix. Alternatively, a helix may include a piercing needle extending through the center and protruding distally of the helix. Other variations may include a dual-helix, a helix having a decreasing diameter, the addition of an articulatable grasping jaw in combination with the helix. Moreover, the helix may be completely or partially hollow with one or more deployable anchors positioned within or advanced through hollow helix.

Alternative variations for the helix may also include optional measures to prevent the helix from inadvertently damaging any surrounding tissue. For example, one variation may include a sheathed helix assembly while another variation may have an insertion member which defines an atraumatic distal end which may be advanced through the center of the helix. Another alternative may include a helix which may be configured to reconfigure itself into a straightened configuration to facilitate its removal from the tissue. In such a device, the helix may be electrically connected via a connection of wires to a power source.

In addition to the variations of the tissue grasper or helix, the stabilizing members, otherwise called extension members, may also include various embodiments. For instance, the upper and/or lower extension members or bails may also be configured with any of the helix variations as practicable. Although the upper and lower extension members or bails may be maintained rigidly relative to one another, the upper and/or lower extension members may be alternatively configured to articulate from a closed to an open configuration or conversely from an open to a closed configuration for facilitating manipulation or stabilization of tissue drawn between the bail members.

Articulation or manipulation of the extension members may be accomplished via any number of methods. For instance, the upper and/or lower extension members may include a pivoting cam member, a linkage assembly, biased extension members which are urged closed or open, etc. Moreover, lower extension member may alternatively be extended in length relative to upper extension member or one or both extension members may be configured to have atraumatic blunted ends to prevent inadvertently damaging surrounding tissue.

Moreover, it is preferable to have sufficient clearance with respect to the lower extension member so that unhindered deployment of the needle assembly or anchors from the apparatus is facilitated. One method for ensuring unhindered deployment is via a lower extension member having a split opening defined near or at its distal end. Alternatively, the lower extension member may be configured to create a "C"-shaped member which allows for an opening along the member.

Alternatively, the lower extension member may be fabricated from a non-conductive material upon which wires may be integrated such that the entire lower member may be electrically conductive, to selectively ablate regions of tissue, if so desired.

Aside from creating ablation regions, the tissue manipulation assembly may be connected to the tubular body via a hinged or segmented articulatable portion which allows the tissue manipulation assembly to be reconfigured from a low-profile configuration straightened relative to the tubular body to an articulated configuration where the assembly forms an angle relative to the tubular body. The articulatable portion may be configured to allow the assembly to become articulated in a single plane or it may also be configured to allow a full range of motion unconstrained to a single plane relative to tubular body to facilitate manipulation of the tissue.

In addition to the extension members, the launch tube itself may be fabricated from a metal such as Nitinol, stainless steel, titanium, etc., to facilitate the flexure of the tube. Such a tube may be selectively scored or cut to enhance the directional flexibility of the tube.

The launch tube may be advanced distally until the deployed needle body of the needle assembly emerges from the launch tube perpendicularly to the tissue drawn between the extension members, and particularly to upper extension member. Thus, the distal opening of the launch tube may be configured to form an angle, .beta., relative generally to the tissue manipulation assembly. The angle, .beta., is preferably close to 90.degree. but it may range widely depending upon the amount of tissue grasped as well as the angle desired.

A distal portion of the launch tube may also be modified to include an extended portion which is configured to remain straight even when the launch tube is flexed into its deployment configuration. This extended portion may provide additional columnar support to a needle body passing through during needle deployment from the launch tube to help ensure the linear deployment of the needle body into or through the tissue.

Alternatively, the needle body may define a cross-sectional shape, other than circular, which is keyed to the extended distal portion of the launch tube. The needle body may be keyed to the launch tube to ensure a specified deployment trajectory of the needle body from the keyed launch tube. Alternatively, the launch tube may be overdriven relative to the tissue manipulation assembly and upper extension member.

The needle assembly which is advanced through the launch tube may generally comprise the needle body attached or integrally formed with a tubular catheter or push tube. The needle body is preferably a hollow tapered needle which is configured to pierce into and through tissue. The needle body may have a variety of tapered piercing ends to facilitate its entry into tissue. One variation which may be utilized to ensure the needle trajectory through the tissue may include a curvable needle body deployed from the launch tube. Such a needle body may be constrained into a straightened configuration when positioned within the launch tube. However, once deployed the needle body may be adapted to reconfigure itself into a curved configuration directed towards the tissue manipulation assembly. The needle body may be curved via an anvil configured to receive and deflect the travel of the needle body into a curved needle body.

Alternatively, the needle body may be replaced with a fiber optic needle which may be deployed through the launch tube to provide visualization of the tissue region prior to, during, or after anchor deployment. In another alternative, advancement of the needle body into and/or through the tissue may be facilitated via an ultrasonic vibrating needle body or a torqueable needle body which may be torqued about its proximal end to facilitate entry into the tissue. The torqueable needle body may be connected via a catheter length having high-torque characteristics.

Rather than deploying anchors from the needle assembly via a distal opening in the needle body, the tissue anchor may alternatively be deployed through one or more side openings defined proximally of the distal tip of the needle body. In yet another alternative, the needle body may have gradations or indicators along its surface to provide a visual indication to the surgeon or physician of the position of the needle body when advanced into or through the tissue or when deployed from the launch tube.

Moreover, the outer surface of the needle body may be dimpled to enhance the visualization of the needle body within the patient body. Moreover, dimples may also enhance the visualization of needle body under ultrasound imaging. Aside from dimples, the outer surface of the needle body may be coated or covered with a radio-opaque material to further enhance visualization of the needle body.

The tissue manipulation assembly may be manipulated and articulated through various mechanisms. One such assembly which integrates each of the functions into a singular unit may comprise a handle assembly which is connected via a tubular body to the tissue manipulation assembly. Such a handle assembly may be configured to separate from the tubular body, thus allowing for reusability of the handle. A tissue manipulation articulation control may also be positioned on the handle to provide for selective articulation of the tissue manipulation assembly.

One particular variation of the handle assembly may have handle enclosure formed in a tapered configuration which is generally symmetrically-shaped about a longitudinal axis extending from the distal end to the proximal end of the handle assembly. The symmetric feature may allow for the handle to be easily manipulated by the user regardless of the orientation of the handle enclosure during a tissue manipulation procedure.

To articulate the multiple features desirably integrated into a singular handle assembly, e.g., advancement and/or deployment of the launch tube, anchor assembly, needle assembly, articulation of the extension members and tissue manipulation assembly, etc., a specially configured locking mechanism may be located within the handle enclosure. Such a locking mechanism may generally be comprised of an outer sleeve disposed about inner sleeve where the outer sleeve has a diameter which allows for its unhindered rotational and longitudinal movement relative to the inner sleeve. A needle deployment locking control may extend radially from the outer sleeve and protrude externally from the enclosure for manipulation by the user. The outer sleeve may also define a needle assembly travel path along its length. The travel path may define the path through which the needle assembly may traverse in order to be deployed.

The needle assembly may define one or more guides protruding from the surface of the assembly which may be configured to traverse within the travel path. The inner sleeve may also define guides protruding from the surface of the inner sleeve for traversal within grooves defined in the handle enclosure. Moreover, the outer sleeve is preferably disposed rotatably about the inner sleeve such that the outer sleeve and inner sleeve are configured to selectively interlock with one another in a corresponding manner when the locking control is manipulated into specified positions.

The needle deployment assembly may be deployed through the approximation assembly by introducing the needle deployment assembly into the handle and through the tubular body such that the needle assembly is advanced from the launch tube and into or through approximated tissue. An elongate and flexible sheath or catheter may extend removably from the needle assembly control or housing which may be interconnected via an interlock which may be adapted to allow for the securement as well as the rapid release of the sheath from the housing through any number of fastening methods, e.g., threaded connection, press-fit, releasable pin, etc. The needle-body, which may be configured into any one of the variations described above, may extend from the distal end of the sheath while maintaining communication between the lumen of the sheath and needle opening.

An elongate pusher may comprise a flexible wire or hypotube which is translationally disposed within the sheath and movably connected within the housing. A proximally-located actuation member may be rotatably or otherwise connected to the housing to selectively actuate the translational movement of elongate pusher relative to the sheath for deploying the anchors from the needle opening. The anchor assembly may be positioned distally of the elongate pusher within the sheath for deployment from sheath. The housing for the needle deployment assembly may also define an indicator window along its length to provide a visual indicator utilized to indicate the position of the elongate pusher within the sheath.

To ensure that the anchor is not prematurely ejected from the needle assembly, various interlocking features or spacing elements may be employed. For instance, adjacent anchors positioned within the needle deployment assembly may be interlocked with one another via a temporary interlocking feature. Likewise, the elongate pusher and an adjacent anchor may be optionally interlocked together as well. Such an interlocking feature may enable the anchor assembly to be advanced distally as well as withdrawn proximally within the sheath and needle body in a controlled manner without the risk of inadvertently pushing one or more anchors out of the needle body.

BRIEF DESCRIPTION OF THE SEVERAL VIEWS OF THE DRAWINGS

FIGS. 35A to 35C show end views of a tissue manipulation assembly which may incorporate various colors into the device to facilitate orientation.

FIGS. 36A to 36C show the corresponding top views, respectively, of the device of FIGS. 35A to 35C.

FIGS. 37A to 37D show side views of various needle bodies which may be colored, have visual markers thereon, dimpled, or have radio-opaque coatings respectively.

DETAILED DESCRIPTION OF THE INVENTION

Figure 1A:
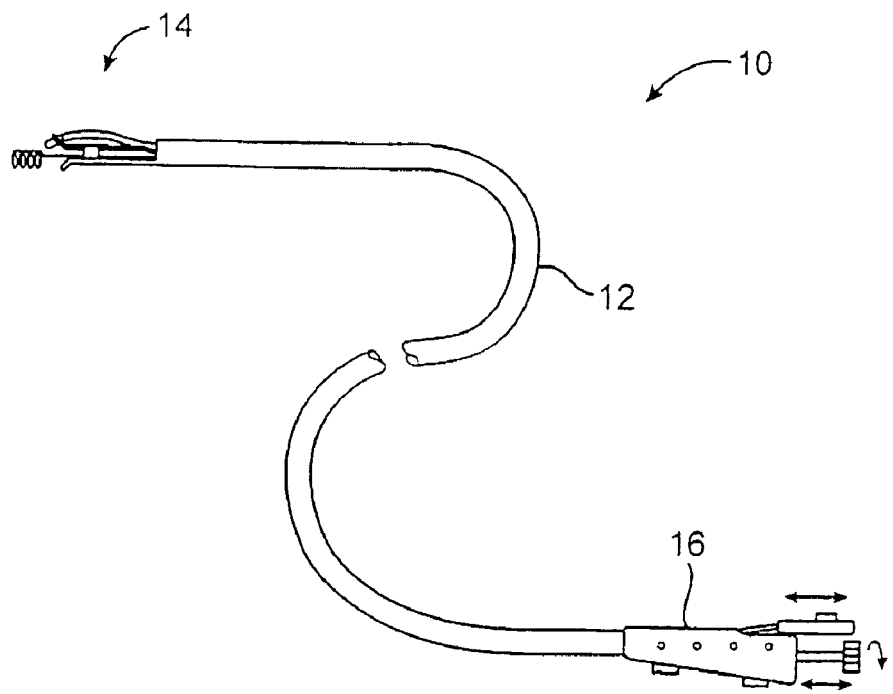
FIG. 1A shows a side view of one variation of a tissue plication apparatus which may be used to create tissue plications and to deliver cinching or locking anchors into the tissue.

In creating tissue plications, a tissue plication tool having a distal tip may be advanced (transorally, transgastrically. etc.) into the stomach. The tissue may be engaged or grasped and the engaged tissue may be moved to a proximal position relative to the tip of the device, thereby providing a substantially uniform plication of predetermined size. Examples of creating and forming tissue plications may be seen in further detail in U.S. patent application Ser. No. 10/735,030 filed Dec. 12, 2003, which is incorporated herein by reference in its entirety.

In order to first create the plication within a body lumen of a patient, various methods and devices may be implemented. The anchoring and securement devices may be delivered and positioned via an endoscopic apparatus that engages a tissue wall of the gastrointestinal lumen, creates one or more tissue folds, and disposes one or more of the anchors through the tissue fold(s). The tissue anchor(s) may be disposed through the muscularis and/or serosa layers of the gastrointestinal lumen.

Generally, in creating a plication through which a tissue anchor may be disposed within or through, a distal tip of a tissue application apparatus may engage or grasp the tissue and move the engaged tissue to a proximal position relative to the tip of the device, thereby providing a substantially uniform plication of predetermined size.

Formation of a tissue fold may be accomplished using at least two tissue contact areas that are separated by a linear or curvilinear distance, wherein the separation distance between the tissue contact points affects the length and/or depth of the fold. In operation, a tissue grabbing assembly engages or grasps the tissue wall in its normal state (i.e., non-folded and substantially flat), thus providing a first tissue contact area. The first tissue contact area then is moved to a position proximal of a second tissue contact area to form the tissue fold. The tissue anchor assembly then may be extended across the tissue fold at the second tissue contact area. Optionally, a third tissue contact point may be established such that, upon formation of the tissue fold, the second and third tissue contact areas are disposed on opposing sides of the tissue fold, thereby providing backside, stabilization during extension of the anchor assembly across the tissue fold from the second tissue contact area.

The first tissue contact area may be utilized to engage and then stretch or rotate the tissue wall over the second tissue contact area to form the tissue fold. The tissue fold may then be articulated to a position where a portion of the tissue fold overlies the second tissue contact area at an orientation that is substantially normal to the tissue fold. A tissue anchor may then be delivered across the tissue fold at or near the second tissue contact area. An apparatus in particular which is particularly suited to deliver the anchoring and securement devices described herein may be seen in further detail in co-pending U.S. patent application Ser. No. 10/840,950 filed May 7, 2004, which is incorporated herein by reference in its entirety.

An illustrative side view of a tissue plication assembly 10 which may be utilized with the tissue anchors described herein is shown in FIG. 1A. The plication assembly 10 generally comprises a catheter or tubular body 12 which may be configured to be sufficiently flexible for advancement into a body lumen, e.g., transorally, percutaneously, laparoscopically, etc. Tubular body 12 may be configured to be torqueable through various methods, e.g., utilizing a braided tubular construction, such that when handle 16 is manipulated and rotated by a practitioner from outside the body, the torquing force is transmitted along body 12 such that the distal end of body 12 is rotated in a corresponding manner.

Figure 1B:
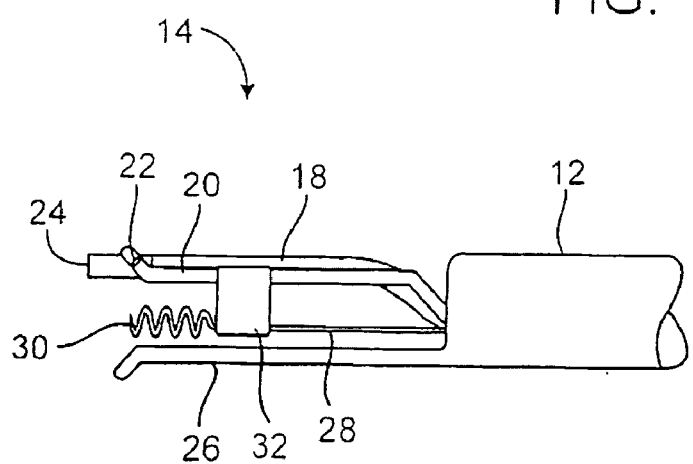
FIGS. 1B and 1C show detail side and perspective views, respectively, of the tissue approximation assembly of the device of FIG. 1A.
Figure 1C:
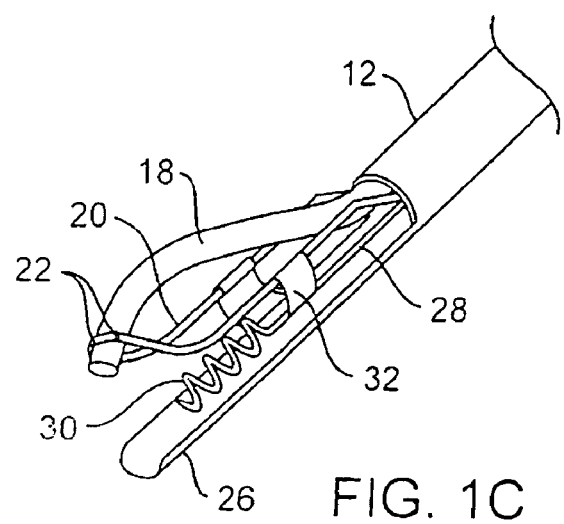

Tissue manipulation assembly 14 is located at the distal end of tubular body 12 and is generally used to contact and form the tissue plication, as mentioned above. FIG. 1B shows an illustrative detail side view and FIG. 1C shows a perspective view of tissue manipulation assembly 14 which shows launch tube 18 extending from the distal end of body 12 and in-between the arms of upper extension member or bail 20. Launch tube 18 may define launch tube opening 24 and may be pivotally connected near or at its distal end via hinge or pivot 22 to the distal end of upper bail 20. Lower extension member or bail 26 may similarly extend from the distal end of body 12 in a longitudinal direction substantially parallel to upper bail 20. Upper bail 20 and lower bail 26 need not be completely parallel so long as an open space between upper bail 20 and lower bail 26 is sufficiently large enough to accommodate the drawing of several layers of tissue between the two members.

Upper bail 20 is shown in the figure as an open looped member and lower bail 26 is shown as a solid member; however, this is intended to be merely illustrative and either or both members may be configured as looped or solid members. Tissue acquisition member 28 may be an elongate member, e.g., a wire, hypotube, etc., which terminates at a tissue grasper or engager 30, in this example a helically-shaped member, configured to be reversibly rotatable for advancement into the tissue for the purpose of grasping or acquiring a region of tissue to be formed into a plication. Tissue acquisition member 28 may extend distally from handle 16 through body 12 and distally between upper bail 20 and lower bail 26. Acquisition member 28 may also be translatable and rotatable within body 12 such that tissue engager 30 is able to translate longitudinally between upper bail 20 and lower bail 26. To support the longitudinal and rotational movement of acquisition member 28, an optional guide or linear bearing 32 may be connected to upper 20 or lower bail 26 to freely slide thereon. Guide 32 may also be slidably connected to acquisition member 28 such that the longitudinal motion of acquisition member 28 is supported by guide 32.

Figure 2A:
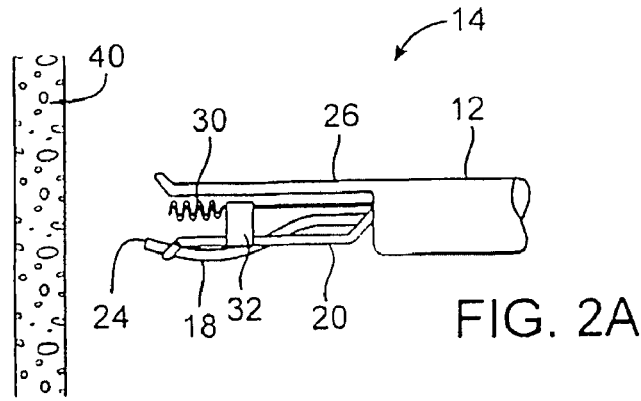
FIG. 2A is a detail side view of the device shown in FIGS. 1A-1C advanced into a body lumen and positioned adjacent to a tissue wall.

An example of a tissue plication procedure is seen in FIGS. 2A to 2D for delivering and placing a tissue anchor and is disclosed in further detail in co-pending U.S. patent application Ser. No. 10/840,950 filed May 7, 2004, which has been incorporated by reference above. Tissue manipulation assembly 14, as seen in FIG. 2A, may be advanced into a body lumen such as the stomach and positioned adjacent to a region of tissue wall 40 to be plicated. During advancement, launch tube 18 may be configured in a delivery profile such that tube 18 is disposed within or between the arms of upper bail 20 to present a relatively small profile.

Figure 2B:
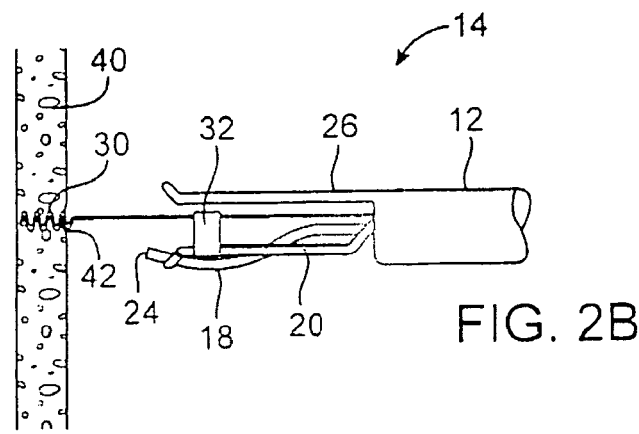
FIG. 2B is a detail side view of the device shown in FIG. 2A with the tissue grasper engaging the tissue wall.

Once tissue manipulation assembly 14 has been desirably positioned relative to tissue wall 40, tissue grasper or engager 30 may be advanced distally such that tissue grasper or engager 30 comes into contact with tissue wall 40 at acquisition location or point 42. As tissue grasper or engager 30 is distally advanced relative to body 12, guide 32, if utilized, may slide distally along with tissue grasper or engager 30 to aid in stabilizing the grasper. If a helically-shaped tissue grasper or engager 30 is utilized, as illustrated in FIG. 2B, it may be rotated from its proximal end at handle 16 and advanced distally until the tissue at point 42 has been firmly engaged by tissue grasper or engager 30. This may require advancement of tissue grasper or engager 30 through the mucosal layer and at least into or through the underlying muscularis layer and possibly into or through the serosa layer.

Figure 2C:
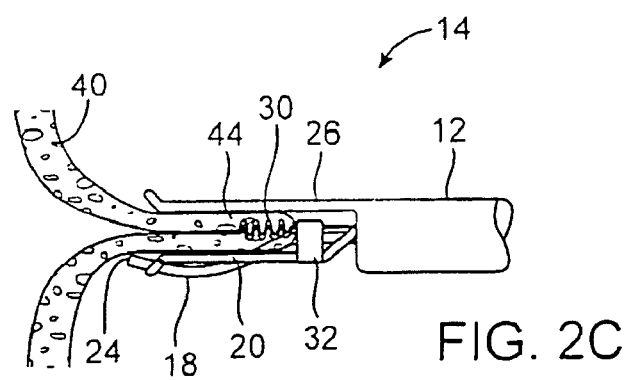
FIG. 2C is a detail side view of the device shown in FIGS. 2A and 2B forming a tissue fold.

The grasped tissue may then be pulled proximally between upper 20 and lower bails 26 via tissue grasper or engager 30 such that the acquired tissue is drawn into a tissue fold 44, as seen in FIG. 2C. As tissue grasper or engager 30 is withdrawn proximally relative to body 12, guide 32 may also slide proximally to aid in stabilizing the device especially when drawing the tissue fold 44.

Once the tissue fold 44 has been formed, launch tube 18 may be advanced from its proximal end at handle 16 such that a portion 46 of launch tube 18, which extends distally from body 12, is forced to rotate at hinge or pivot 22 and reconfigure itself such portion 46 forms a curved or arcuate shape that positions launch tube opening 24 perpendicularly relative to a longitudinal axis of body 12 and/or bail members 20, 26. Launch tube 18, or at least portion 46 of launch tube 18, is preferably fabricated from a highly flexible material or it may be fabricated, e.g., from Nitinol tubing material which is adapted to flex, e.g., via circumferential slots, to permit bending. Alternatively, assembly 14 may be configured such that launch tube 18 is reconfigured simultaneously with the proximal withdrawal of tissue grasper or engager 30 and acquired tissue 44.

As discussed above, the tissue wall of a body lumen, such as the stomach, typically comprises an inner mucosal layer, connective tissue, the muscularis layer and the serosa layer. To obtain a durable purchase, e.g., in performing a stomach reduction procedure, the staples or anchors used to achieve reduction of the body lumen are preferably engaged at least through or at the muscularis tissue layer, and more preferably, the serosa layer. Advantageously, stretching of tissue fold 44 between bail members 20, 26 permits an anchor to be ejected through both the muscularis and serosa layers, thus enabling durable gastrointestinal tissue approximation.

Figure 2D:
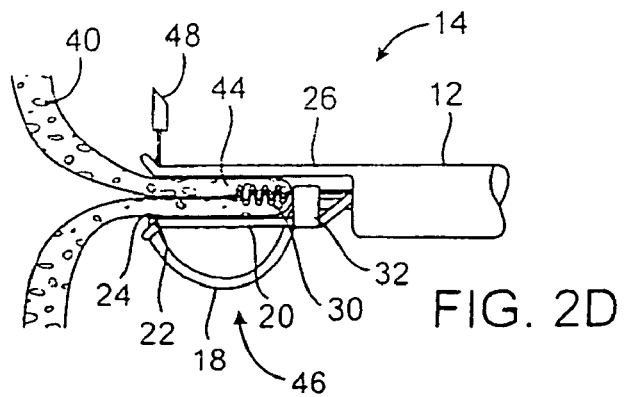
FIG. 2D is a detail side view of the device shown in FIGS. 2A-2C with the needle assembly piercing the tissue fold.

As shown in FIG. 2D, once launch tube opening 24 has been desirably positioned relative to the tissue fold 44, needle assembly 48 may be advanced through launch tube 18 via manipulation from its proximal end at handle 16 to pierce preferably through a dual serosa layer through tissue fold 44. Needle assembly 48 is preferably a hollow tubular needle through which one or several tissue anchors may be delivered through and ejected from in securing the tissue fold 44, as further described below.

Figure 3A:
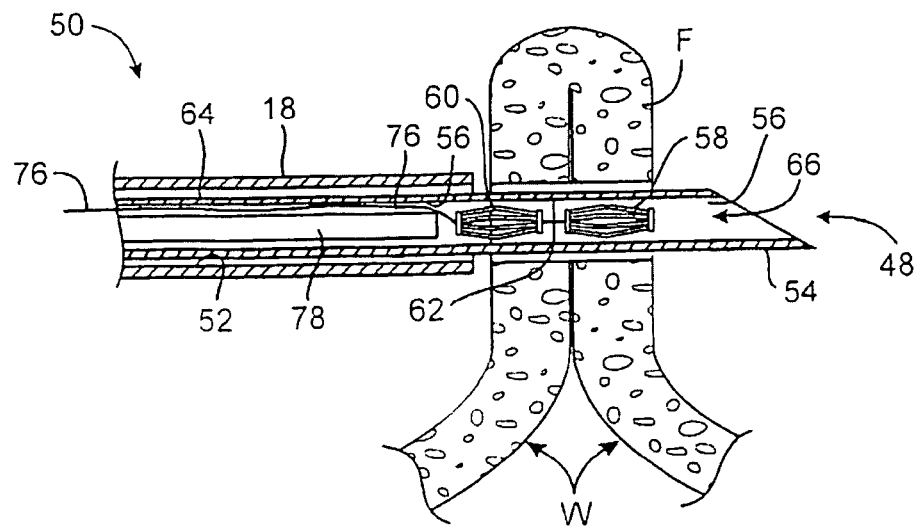
FIG. 3A shows a cross-sectional side view of an anchor delivery assembly delivering a basket-type anchor into or through a tissue fold.

Because needle assembly 48 penetrates the tissue wall twice, it exits within the body lumen, thus reducing the potential for injury to surrounding organs. A detail cross-sectional view is shown in FIG. 3A of anchor delivery assembly 50 in proximity to tissue fold F. In this example, tissue fold F may comprise a plication of tissue created using the apparatus described herein or any other tool configured to create such a tissue plication. Tissue fold F may be disposed within a gastrointestinal lumen, such as the stomach, where tissue wall W may define the outer or serosal layer of the stomach. Anchor delivery assembly may generally comprise launch tube 18 and needle assembly 48 slidingly disposed within launch tube lumen 52. Needle assembly 48 is generally comprised of needle 54, which is preferably a hollow needle having a tapered or sharpened distal end to facilitate its travel into and/or through the tissue. Other parts of the assembly, such as upper and lower bail members 20, 26, respectively, and tissue acquisition member 28 have been omitted from these figures only for clarity.

Once launch tube 18 has been desirably positioned with respect to tissue fold F, needle 54 may be urged or pushed into or through tissue fold F via delivery push tube or catheter 64 from its proximal end preferably located within handle 16. Delivery push tube or catheter 64 may comprise an elongate flexible tubular member to which needle 54 is connected or attached via joint 62. Alternatively, needle 54 and delivery push tube 64 may be integrally formed from a singular tubular member. Needle 54 may define needle lumen 56 through which basket anchor assembly 66, i.e., distal anchor 58 and/or proximal anchor 60 may be situated during deployment and positioning of the assembly. A single suture or flexible element 76 (or multiple suture elements) may connect proximal anchor 60 and distal anchor 58 to one another. For instance, element 76 may comprise various materials such as monofilament, multifilament, or any other conventional suture material, elastic or elastomeric materials, e.g., rubber, etc.

Alternatively, metals which are biocompatible may also be utilized for suture materials. For instance, sutures may be made from metals such as Nitinol, stainless steels, Titanium, etc., provided that they are formed suitably thin and flexible. Using metallic sutures with the anchoring mechanisms described herein may additionally provide several benefits. For example, use of metallic suture material may decrease any possibilities of suture failure due to inadvertent cutting or shearing of the suture, it may provide a suture better able to withstand the acidic and basic environment of the gastrointestinal system, and it may also enhance imaging of the suture and anchor assembly if examined under conventional imaging systems such as X-rays, fluoroscopes, MRI, etc. As used herein, suture 76 may encompass any of these materials or any other suitable material which is also biocompatible.

Needle 54 may optionally define a needle slot along its length to allow suture 76 to pass freely within and out of needle 54 when distal anchor 58 is ejected from needle lumen 56. Alternatively, rather than utilizing a needle slot, needle 54 may define a solid structure with suture 76 being passed into and through needle lumen 56 via the distal opening of needle 54.

The proximal end of suture 76 may pass slidingly through proximal anchor 60 to terminate in a suture loop. The proximal end of suture 76 may terminate proximally of the apparatus 10 within control handle 16, proximally of control handle 16, or at some point distally of control handle 16. In this variation, a suture loop may be provided to allow for a grasping or hooking tool to temporarily hold the suture loop for facilitating the cinching of proximal 60 and distal 58 anchors towards one another for retaining a configuration of tissue fold F, as described in further detail in U.S. patent application Ser. No. 10/840,950, which has been incorporated by reference above.

After needle assembly 48 has been pushed distally out through launch tube opening 24 and penetrated into and/or through tissue fold F, as shown in FIG. 3A, anchor pushrod or member 78 may be actuated also via its proximal end to eject distal anchor 58. Once distal anchor 58 has been ejected distally of tissue fold F, needle 54 may be retracted back through tissue fold F by either retracting needle 54 back within launch tube lumen 18 or by withdrawing the entire anchor delivery assembly 50 proximally relative to tissue fold F.

Figure 3B:
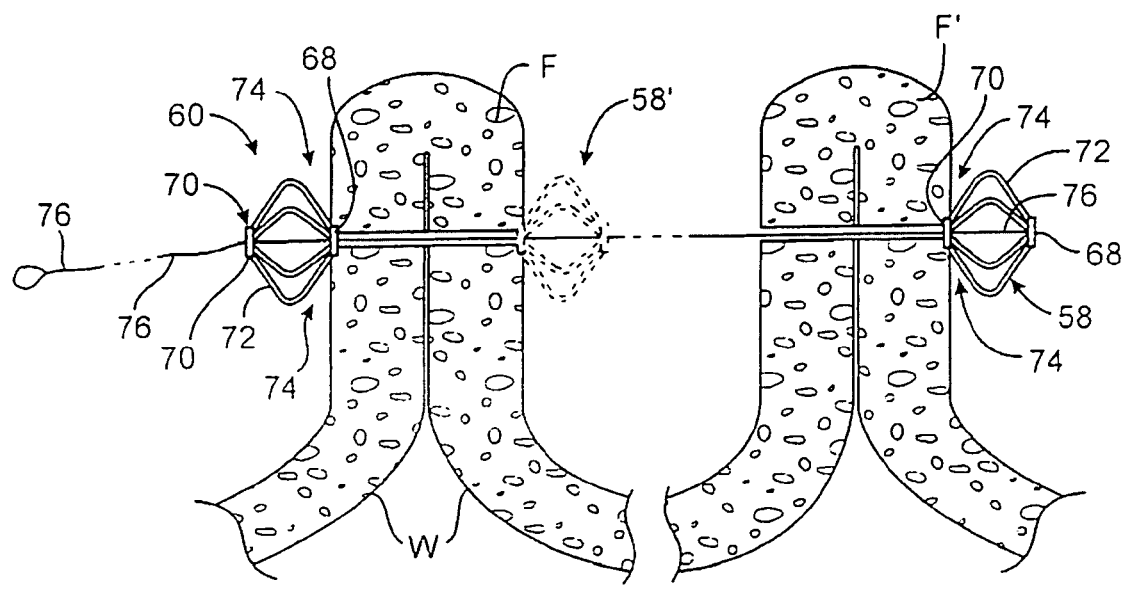
FIG. 3B shows a cross-sectional side view of multiple tissue folds which may be approximated towards one another and basket anchors as being deliverable through one or both tissue folds.

Once needle 54 has been retracted, proximal anchor 60 may then be ejected from launch tube 18 on a proximal side of tissue fold F. With both anchors 58, 60 disposed externally of launch tube 18 and suture 76 connecting the two, proximal anchor 60 may be urged into contact against tissue fold F, as shown in FIG. 3B. As proximal anchor 60 is urged against tissue fold F, proximal anchor 60 or a portion of suture 76 may be configured to provide any number of directionally translatable locking mechanisms which provide for movement of an anchor along suture 76 in a first direction and preferably locks, inhibits, or prevents the reverse movement of the anchor back along suture 76. In other alternatives, the anchors may simply be delivered through various elongate hollow tubular members, e.g., a catheter, trocars, etc.

The basket anchors may comprise various configurations suitable for implantation within a body lumen. Basket anchors are preferably reconfigurable from a low profile delivery configuration to a radially expanded deployment configuration in which a number of struts, arms, or mesh elements may radially extend once released from launch tube 18 or needle 54. Materials having shape memory or superelastic characteristics or which are biased to reconfigure when unconstrained are preferably used, e.g., spring stainless steels, Ni—Ti alloys such as Nitinol, etc. In FIGS. 3A and 3B, each of the basket anchor 58, 60 is illustrated as having a number of reconfigurable struts or arm members 72 extending between distal collar 68 and proximal collar 70; however, this is intended only to be illustrative and suitable basket anchors are not intended to be limited to baskets only having struts or arms. Examples of suitable anchors are further described in detail in U.S. patent application Ser. No. 10/612,170, which has already been incorporated herein above.

FIG. 3B shows distal basket anchor 58 delivered through tissue fold F via needle 54 and launch tube 18. As above, the other parts of the plication assembly, such as upper and lower bail members 20, 26, respectively, and tissue acquisition member 28 have been omitted from these figures only for clarity.

FIG. 3B shows one variation where a single fold F may be secured between proximal anchor 60 and distal anchor 58'. As seen, basket anchor 58' has been urged or ejected from needle 54 and is shown in its radially expanded profile for placement against the tissue surface. In such a case, a terminal end of suture 76 may be anchored within the distal collar of anchor 58' and routed through tissue fold F and through, or at least partially through, proximal anchor 60, where suture 76 may be cinched or locked proximally of, within, or at proximal anchor 60 via any number of cinching mechanisms. Proximal anchor 60 is also shown in a radially expanded profile contacting tissue fold F along tissue contact region 74. Locking or cinching of suture 76 proximally of proximal anchor 60 enables the adequate securement of tissue fold F.

Various examples of cinching devices and methods which may be utilized with the tools and devices herein are described in further detail in U.S. patent application Ser. No. 10/840,950 filed May 7, 2004, which has been incorporated herein above.

If additional tissue folds are plicated for securement, distal basket anchor 58 may be disposed distally of at least one additional tissue fold F', as shown in FIG. 3B, while proximal anchor 60 may be disposed proximally of tissue fold F. As above, suture 76 may be similarly affixed within distal anchor 58 and routed through proximal anchor 60, where suture 76 may be cinched or locked via proximal anchor 60, as necessary. If tissue folds F and F' are to be positioned into apposition with one another, distal basket anchor 58 and proximal anchor 60 may be approximated towards one another. As described above, proximal anchor 60 is preferably configured to allow suture 76 to pass freely therethrough during the anchor approximation. However, proximal anchor 60 is also preferably configured to prevent or inhibit the reverse translation of suture 76 through proximal anchor 60 by enabling uni-directional travel of anchor 60 over suture 76. This cinching feature thereby allows for the automated locking of anchors 58, 60 relative to one another during anchor approximation.

With respect to the anchor assemblies described herein, the types of anchors shown and described are intended to be illustrative and are not limited to the variations shown. For instance, several of the tissue anchor variations are shown as "T"-type anchors while other variations are shown as reconfigurable "basket"-type anchors, which may generally comprise a number of configurable struts or legs extending between at least two collars or support members. Other variations of these or other types of anchors are also contemplated for use in an anchor assembly. Moreover, a single type of anchor may be used exclusively in an anchor assembly; alternatively, a combination of different anchor types may be used in an anchor assembly. Furthermore, the different types of cinching or locking mechanisms are not intended to be limited to any of the particular variations shown and described but may be utilized in any of the combinations or varying types of anchors as practicable.

Tissue Engagement Tools

Figure 4A:
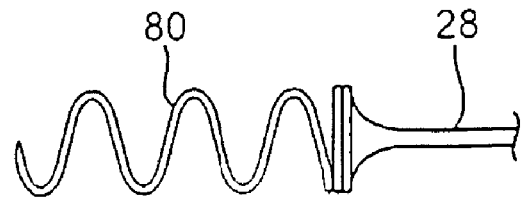
FIG. 4A shows a side view of one variation for a tissue engaging helix.

As mentioned above, tissue acquisition member 28 may be an elongate member, e.g., a wire, hypotube, etc., which has a tissue grasper or engager 30 attached or integrally formed at its distal end for grasping or engaging the tissue. In one variation, the tissue grasper may be formed as a helix having a uniform outer diameter with a constant pitch, as shown in the detail view of helix 80 in FIG. 4A. Helix 80 may be attached to acquisition member 28 via any suitable fastening method, e.g., adhesives, solder, etc. Alternatively, helix 80 may be integrally formed from the distal portion of acquisition member 28 by winding or coiling the distal portion in a helix configuration.

Figure 4B:
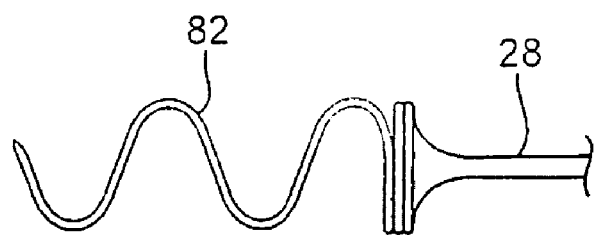
FIG. 4B shows a side view of another variation for a helix having a reduced pitch.
Figure 4C:
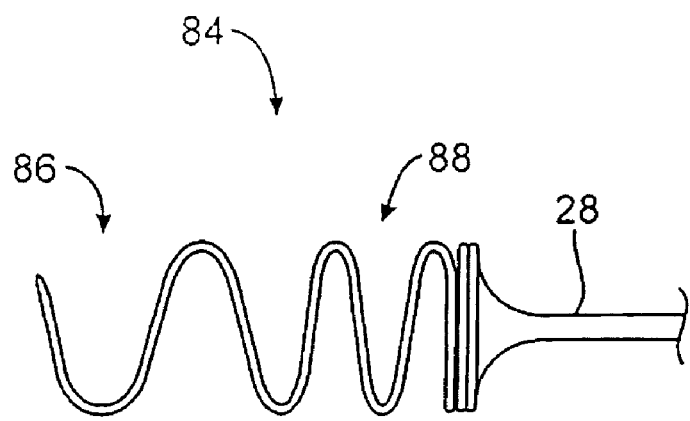
FIG. 4C shows a side view of another variation for a helix having a varied pitch.

In another variation, the tissue grasper may be formed into a helix 82 having a pitch which is greater relatively than helix 80 such that the variation of helix 82 has relatively fewer windings, as shown in FIG. 4B. Alternatively, a multi-pitch helix 84 may be formed having one or more regions with varying pitch along a length of helix 84. As seen in FIG. 4C, multi-pitch helix 84 may have a distal portion 86 having a relatively lower pitch and a proximal portion having a relatively higher pitch 88. A single helix having regions of varied pitch may be utilized to initially pierce and grasp tissue onto the region of lower pitch 86; when the helix 84 is rotated to advance into or through the tissue, the pierced tissue advanced over helix 84 may be wound upon the region of higher pitch 88 where the tissue may be better adhered to helix 84 by the tighter windings.

Figure 4D:
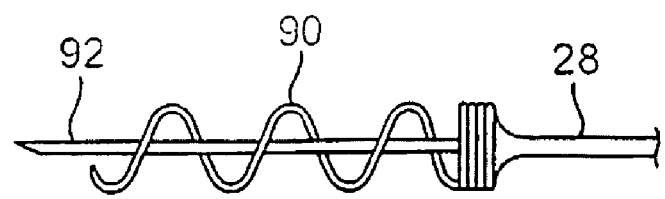
FIG. 4D shows a side view of another variation for a helix having a piercing needle positioned through the helix.
Figure 4E:
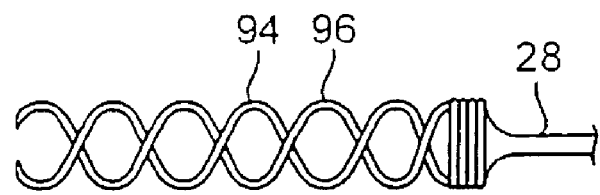
FIG. 4E shows a side view of another variation having a dual helix.

Another variation of a tissue grasper may be seen in FIG. 4D. In this variation, helix 90 may have a piercing needle 92 extending through the center and protruding distally of helix 90 to facilitate piercing of the tissue and initial entry of helix 90 into the tissue. Yet another variation is shown in FIG. 4E where a dual-helix variation may be utilized. Here, first helix 94 may be inter-wound with second helix 96 in a dual helix configuration.

Figure 4F:
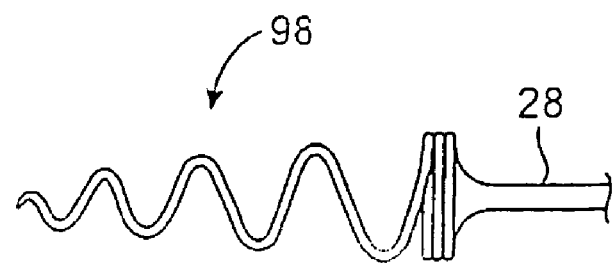
FIG. 4F shows a side view of another variation for a helix having a decreasing diameter.

Another variation is shown in FIG. 4F in which helix 98 may define a helix having a decreasing diameter distally of acquisition member 28. In this variation or any of the variations of the helix described herein, certain aspects of one helix variation may be utilized in any number of combinations with any of the other aspects of other variations as practicable. For instance, the variation of the dual-helix in FIG. 4E may also comprise the piercing needle 92 of FIG. 4D. This variation may also include aspects of the helix 84 having varying regions of differing pitch, as shown in FIG. 4C, and so on in any number of combinations as practicable.

Figure 4G:
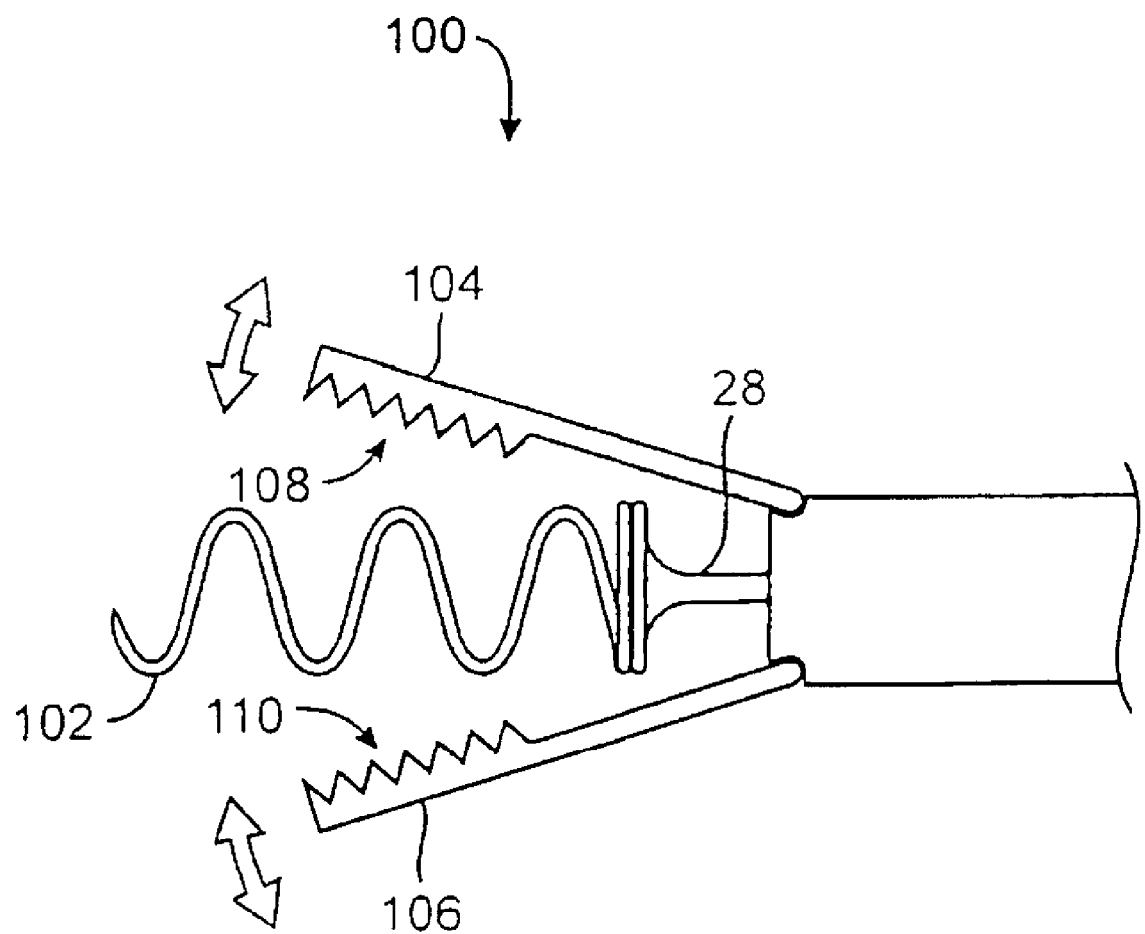
FIG. 4G shows a side view of another variation for a helix combined with a grasper.

FIG. 4G shows yet another variation in dual grasping assembly 100 where helix 102 may utilize articulatable grasping jaw members 104, 106 in combination with the helix 102. As the helix 102 initially pierces and rotatingly retains the tissue, acquisition member 28 may be withdrawn proximally to pull the tissue between jaws 104, 106, which may then be articulated to further clamp onto the tissue to ensure tissue retention by assembly 100. Articulatable jaws 104, 106 may optionally define serrations or teeth 108, 110 upon one or more of the jaw members 104, 106 in contact against the tissue to further facilitate tissue retention.

Figure 5A:
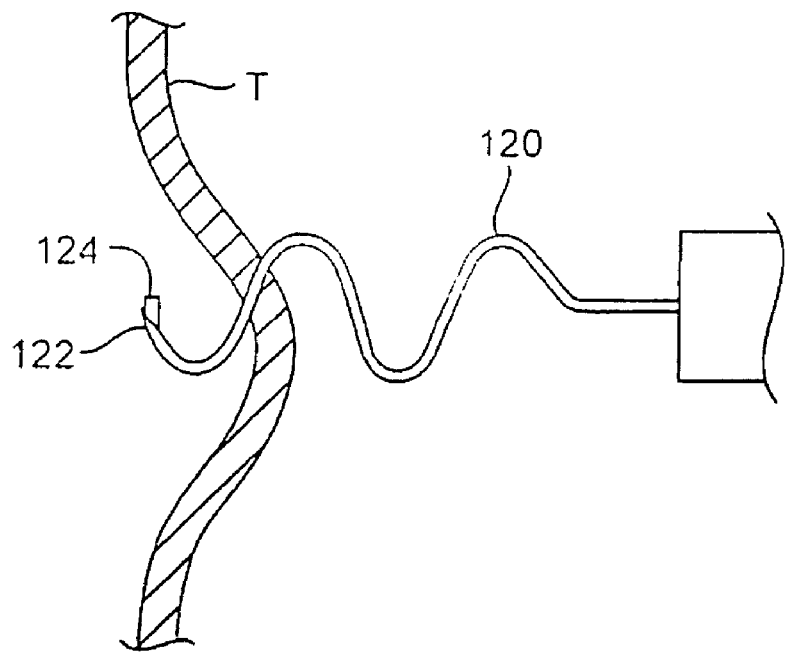
FIGS. 5A and 5B show a hollow helix variation for deploying anchors directly through the helix.
Figure 5B:
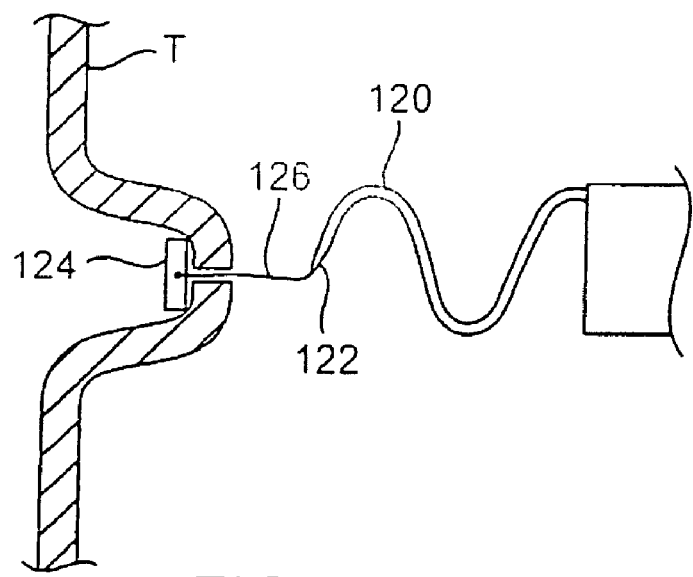

In addition to the various configurations, the tissue grasper may be further utilized to retain tissue via tissue anchors. FIGS. 5A and 5B show side views of a helix variation 120 which may be completely or partially hollow for engaging tissue. One or more deployable anchors 124 may be positioned within or advanced through hollow helix 120. With at least the distal portion or tip of hollow helix 120 pierced into or through the tissue T, as shown in FIG. 5A, tissue anchor 124 may be urged from opening 122 defined in hollow helix 120 through any number of methods, e.g., an elongate pusher. Once tissue anchor 124 has been deployed or ejected from distal opening 122, helix 120 may be withdrawn proximally partially or entirely from tissue T while leaving anchor 124 behind. Anchor 124 may be connected to suture 126 which may be routed through or connected to helix 120 such that creation of a tissue fold from tissue T may be achieved by pulling anchor 124 proximally, as shown in FIG. 5B. After the tissue T has been desirably manipulated or folded, suture 126 may be released from helix 120 so that helix 120 may be withdrawn from the region.

Figure 6A:
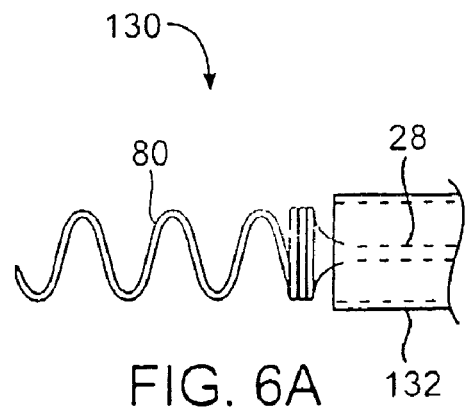
FIGS. 6A and 6B show another variation of a helix with a protective sheath which may be advanced over the helix.
Figure 6B:
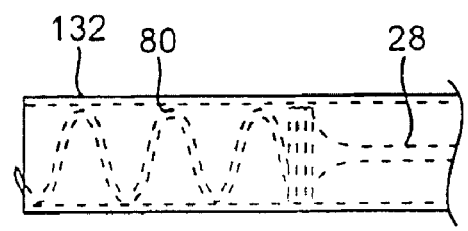

During manipulation of the tissue and articulation of the helix within the patient's body, e.g., within the stomach, optional measures may be taken to prevent the helix from inadvertently damaging any surrounding tissue. One variation may be seen in the detail side view of sheathed helix assembly 130 in FIG. 6A. The sheath 132 may completely or partially cover helix 80 to present an atraumatic surface to the surrounding tissue when the helix 80 is not in use within the patient's body, as shown in FIG. 6B. Additionally, sheath 132 may also be utilized outside the patient to protect helix 80 when handled for transport or during preparation of the device for use. Sheath 132 may be optionally advanced distally over helix 80 or helix 80 may be withdrawn proximally into sheath 132.

Figure 7A:
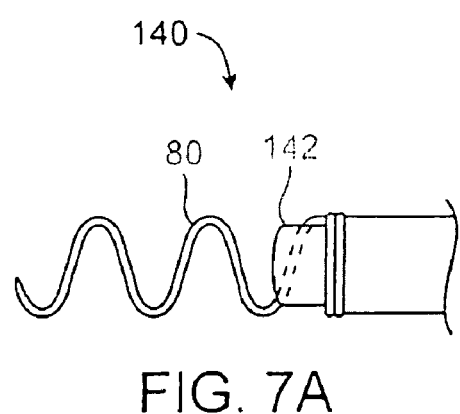
FIGS. 7A and 7B show another variation of a helix with an atraumatic member which may be advanced longitudinally through the helix.
Figure 7B:
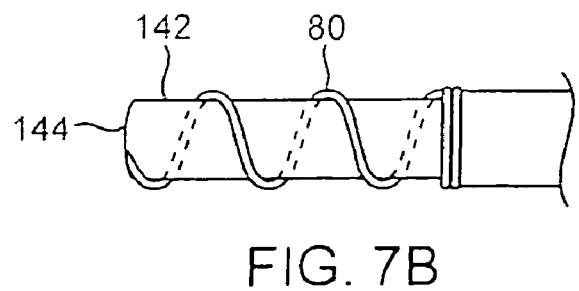

Another variation for providing an atraumatic surface for the helix to surrounding tissue may be seen in FIGS. 7A and 7B. As shown, helix assembly 140 may have an insertion member 142 which defines an atraumatic distal end 144 advanced through the center of helix 80. When the helix 80 is not in use, insertion member 142 may be advanced distally within helix 80 to the distal end of helix 80 such that inadvertent tissue piercing is prevented by member 142.

Figure 8:
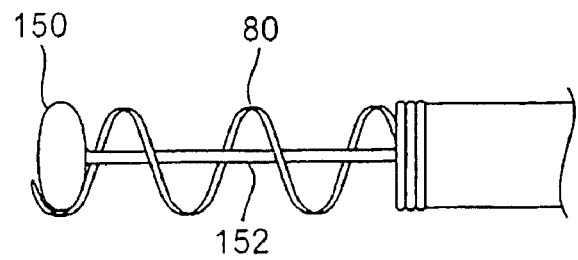
FIG. 8 shows another variation of a helix with a blunted member which may be advanced longitudinally through the helix.

Yet another variation is shown in FIG. 8 in which blunted element 150 may be advanced through the center of helix 80 via an elongate delivery member 152. When helix 80 is utilized, member 150 may be withdrawn proximally relative to helix 80 in the same manner as helix assembly 140 above.

Figure 9A:
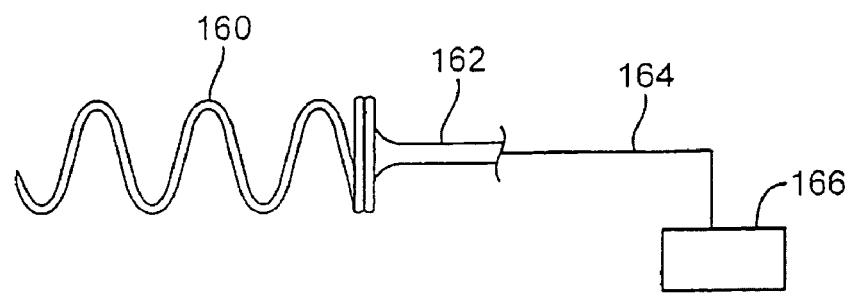
FIGS. 9A and 9B show a helix which may be energized to reform into a straightened configuration, respectively, to facilitate its withdrawal from tissue.
Figure 9B:
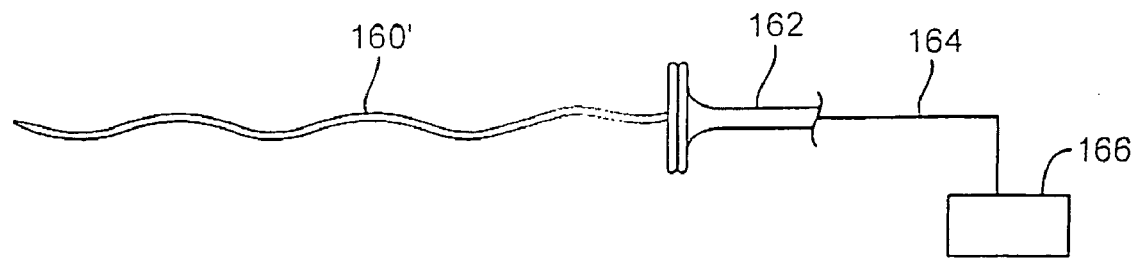

Another variation of the helix assembly is shown in the illustrative side views of FIGS. 9A and 9B. In this variation, reconfigurable helix 160 may be configured to have a configuration for facilitating its advancement into tissue or for withdrawing the helix 160 from tissue. FIG. 9A shows reconfigurable helix 160 is seen in its coiled configuration for piercing and adhering tissue thereto. Helix 160 may be fabricated from a shape memory alloy, such as Nitinol, to have a relaxed configuration of a helix, as shown in FIG. 9A. Once energy is applied, helix 160 may be configured to reconfigure itself into a straightened configuration 160', as shown in FIG. 9B, to facilitate its removal from the tissue. Helix 160 may be electrically connected via electrically conductive acquisition member 162 and connection or wires 164 to a power source 166. If helix 160 were advanced into tissue in its coiled configuration, withdrawal of the helix 160 may be quickly effected by applying energy to helix 160 via power source 166. Alternatively, power may be applied to helix 160 such that its straightened configuration 160' takes shape to facilitate piercing into tissue. Power may then be removed such that helix 160 conforms into its coiled configuration once in the tissue such that the tissue adheres to the helix 160.

Figure 10:
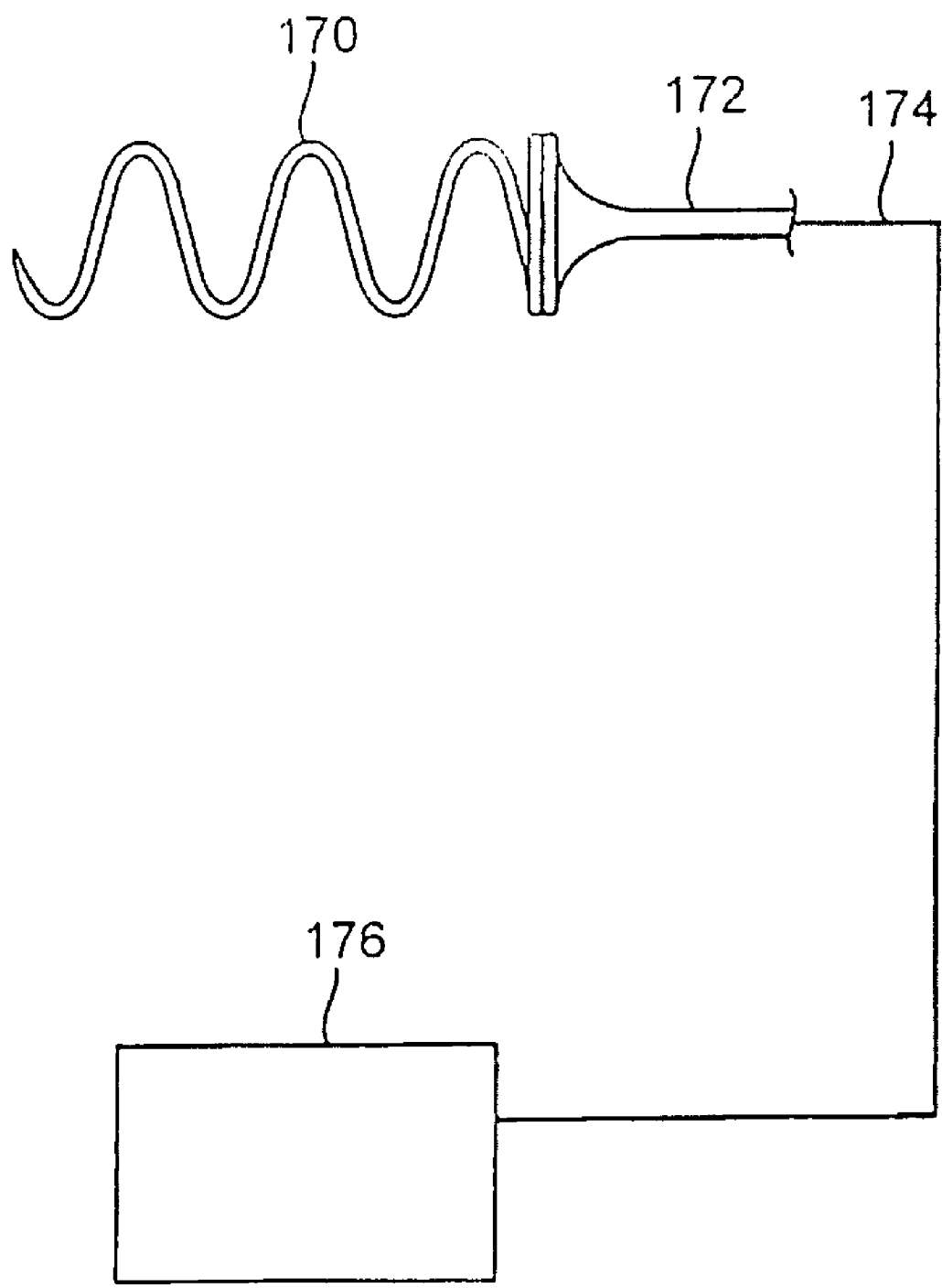
FIG. 10 shows a helix variation which may be energized by a power source for use in ablating surrounding tissue.

In the reconfigurable helix 160 above, the length of helix 160 may be insulated to shield the surrounding tissue from the applied energy. However, another variation of the tissue grasping member may be seen in energizable helix 170 in FIG. 10. In this variation, the entire length or a partial length of helix 170 may be uninsulated such that when helix 170 is energized through electrical connection 174 and through electrically conductive acquisition member 172 via power source 176, the uninsulated portion or portions of energized helix 170 may be utilized to contact and ablate selected regions of tissue. For instance, prior to or after a tissue fold has been formed, helix 170 may be energized to ablate the areas of the tissue which are to be approximated towards one another to facilitate tissue adhesion between selected regions of tissue folds.

As mentioned above, in this variation or any of the variations of the helix, certain aspects of one helix variation may be utilized in any number of combinations with any of the other aspects of other variations as practicable.

Extension Members

In addition to the variations of the tissue grasper or helix, the upper and/or lower extension members or bails may also be configured into a variety of embodiments which may be utilized in any number of combinations with any of the helix variations as practicable. Although the upper and lower extension members or bails may be maintained rigidly relative to one another, the upper and/or lower extension members may be alternatively configured to articulate from a closed to an open configuration or conversely from an open to a closed configuration for facilitating manipulation or stabilization of tissue drawn between the bail members.

In operation, once the selected region of tissue has been acquired by the tissue grasper 30, the obtained tissue may be proximally withdrawn between the bail members, which may act as stabilizers for the tissue. To accommodate large portions of grasped tissue between the bail members, one or both bail members may be articulated or urged to open apart from one another to allow the tissue to enter and become positioned between the bail members. One or both bail members may then be articulated or urged to clamp or squeeze the tissue fold between the bail members to facilitate stabilization of the tissue fold for tissue manipulation and/or anchor deployment and/or any other procedure to be undertaken.

Figure 11A:
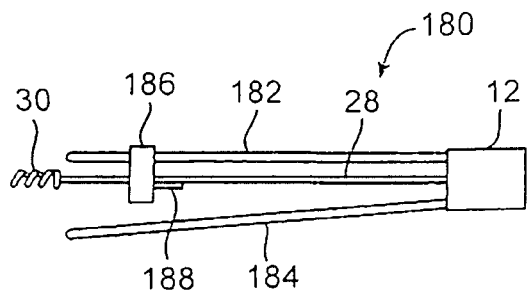
FIGS. 11A and 11B show side views of one variation of the tissue manipulation assembly having cam-actuated extension members.
Figure 11B:
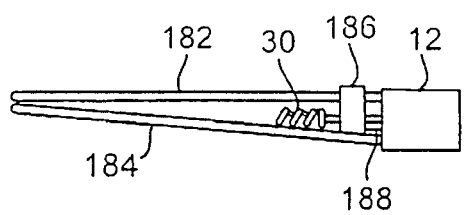

One such articulatable extension assembly may be seen in the side views of FIGS. 11A and 11B. Other features such as the launch tube and tubular body have been omitted merely for the sake of clarity for the following illustrations. As seen in FIG. 11A, upper extension member 182 and lower extension member 184 of active extension assembly 180 may be configured to have an open or spread configuration relative to one another when guide or linear bearing 186 is positioned distally along upper extension member 182. Linear bearing 186 may be configured to slide freely along upper extension member 182 when urged by acquisition member 28 distally or proximally. Rather than having linear bearing 186 slide along upper extension member 182, it may be configured alternatively to slide along lower extension member 184.

Figure 11C:
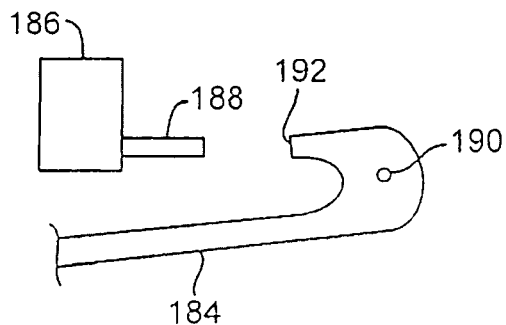
FIGS. 11C and 11D show detail views of the cam-actuation for the assembly of FIGS. 11A and 11B.
Figure 11D:
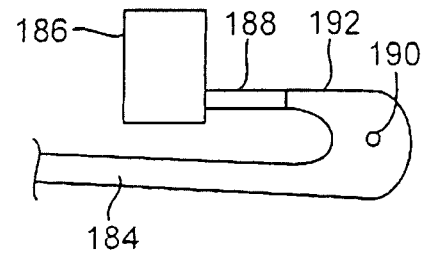

With tissue grasper 30 and acquisition member 28 distally protruding from extension members 182, 184, as shown in FIG. 11A, the desired region of tissue may be acquired by rotating tissue grasper 30 into the tissue. Once tissue has been acquired by tissue grasper 30, the tissue may be pulled between the opened extension members 182, 184 by proximally withdrawing tissue grasper 30 and linear bearing 186 may be forced proximally over upper extension member 182, as shown in the detail view of FIG. 11C. One or more projections or pistons 188 may protrude proximally from linear bearing 186 such that one or more of these projections 188 comes into contact with actuation lever or member 192, as shown in FIG. 11D, which may be located proximally of extension members 182, 184 and connected in a pivoting relationship with lower extension member 184 about pivot 190. As linear bearing 186 is urged proximally and projection 188 presses against actuation lever 192, lower extension member 184 may be rotated about pivot 190 such that lower extension member 184 is urged towards upper extension member 182 to securely clamp onto and retain any tissue positioned between the extension members 182, 184.

Figure 12A:
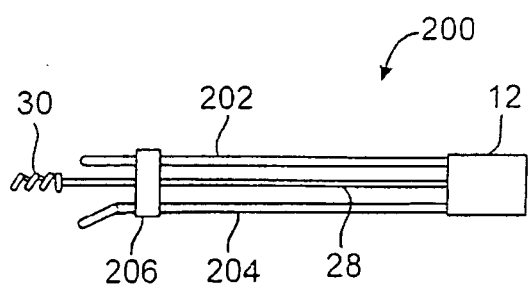
FIGS. 12A and 12B show side views of another variation of extension members which are biased towards one another.
Figure 12B:
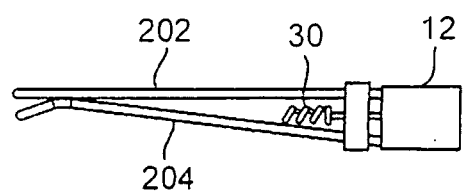

Another articulatable extension assembly may be seen in assembly 200 in the side views of FIGS. 12A and 12B. In this variation, upper extension member 202 may project distally opposite lower extension member 204 which may be biased to close towards upper extension member 202. When tissue grasper 30 is advanced to engage tissue, as shown in FIG. 12A, linear bearing 206 may be urged distally along upper extension member 202 via acquisition member 28 such that lower extension member 204 is forced or wedged away from upper extension member 202. Once the tissue is engaged and withdrawn proximally, linear bearing 206 may be pulled proximally while sliding along lower member 204 and allowing lower member 204 to spring back towards upper member 202 and over any tissue positioned therebetween, as shown in FIG. 12B.

Figure 13A:
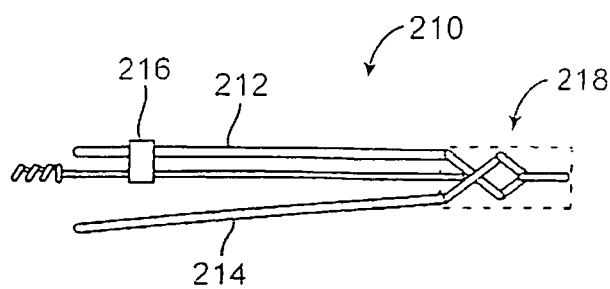
FIGS. 13A and 13B show side views of another variation of extension members which are actuated via a linkage assembly.
Figure 13B:
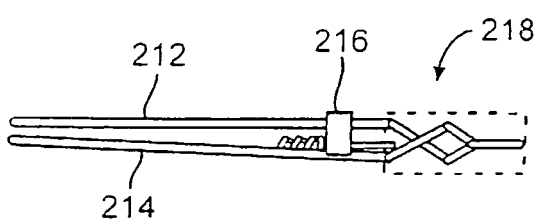

Another articulatable extension assembly is shown in the side views of extension assembly 210 of FIGS. 13A and 13B. In this variation, upper extension member 212 and/or lower extension member 214 may be connected to linkage assembly 218 located proximally of the extension members 212, 214. Linkage assembly 218 may be manipulated via any number of control mechanisms such as control wires to urge extension members 212, 214 between open and closed configurations. Alternatively, linkage assembly 218 may be configured to open or close upon the proximal or distal advancement of linear bearing 216 relative to linkage assembly.

Figure 14A:
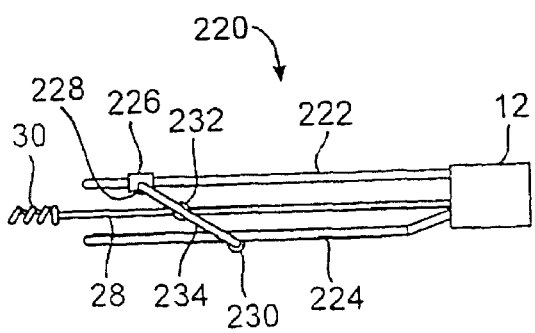
FIGS. 14A to 14C show side views of another variation of extension members which are actuatable via one or more hinged arms interconnecting the extension members.
Figure 14B:
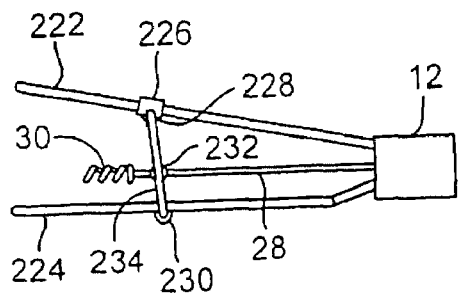
Figure 14C:
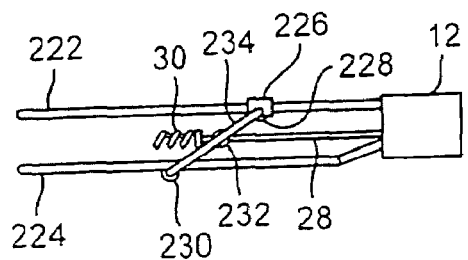

FIGS. 14A to 14C show side views of another variation in extension assembly 220 where upper and lower extension members 222, 224 are articulatable between open and closed configurations via a pivoting arm or member 234 interconnecting the two. In this example, a first end of pivoting arm 234 may be in a pivoting connection at pivot 228 with linear bearing 226, which may slide translationally along upper member 222. A second end of pivoting arm 234 may also be in a pivoting connection with lower extension member 224 at pivot 230, which may remain fixed to lower member 224. Acquisition member 28 may also be in a third pivoting connection with pivoting arm 234 at pivot 232, which may also be configured to allow for the linear translation of acquisition member therethrough.

In operation, when acquisition member 28 and tissue grasper 30 is advanced distally, as shown in FIG. 14A, both upper and lower extension members 222, 224 are in a closed configuration with linear bearing 226 being advanced distally along upper extension member 222. As tissue grasper 30 is withdrawn proximally between extension members 222, 224, pivoting arm 234 may be pivoted about fixed pivot 230 on lower member 224 while upper member 222 is urged into an open configuration as linear bearing 226 is urged proximally over upper member 222, as shown in FIG. 14B. This expanded or open configuration allows for the positioning of large portions of tissue to be drawn between the extension members 222, 224 for stabilization. FIG. 14C shows tissue grasper 30 as having been further withdrawn and linear bearing 226 urged proximally such that upper member 222 is urged back into a closed configuration relative to lower member 224. The closing of extension members 222, 224 allows for the members to further clamp upon any tissue therebetween for further stabilization of the tissue.

Figure 15A:
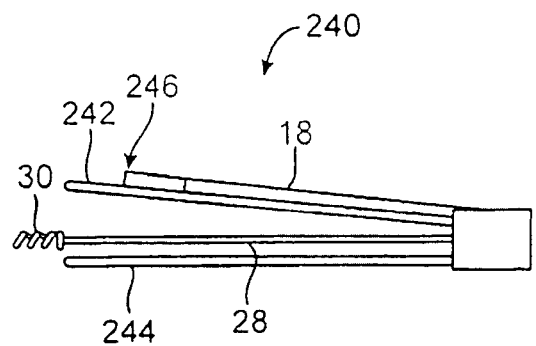
FIGS. 15A and 15B show side views of another variation where one or more extension members are biased away from one another.
Figure 15B:
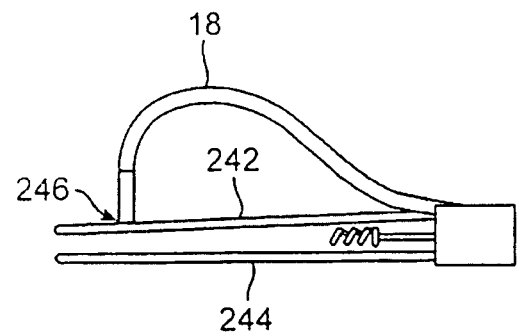

FIGS. 15A and 15B show another alternative in active extension assembly 240. In this variation, upper extension member 242 may be biased to extend away from lower extension member 244. As shown in FIG. 15A, upper extension member 242 may remain in an open configuration relative to lower member 244 for receiving tissue therebetween. In this variation, biased upper member 242 may be urged into a closed configuration by pivoting the launch tube 18 about pivot 246, which may be located along upper member 242. As launch tube 18 is pivoted into an anchor deployment configuration, the pivoting action may urge upper member 242 towards lower member 244 to clamp upon any tissue therebetween.

Figure 16A:
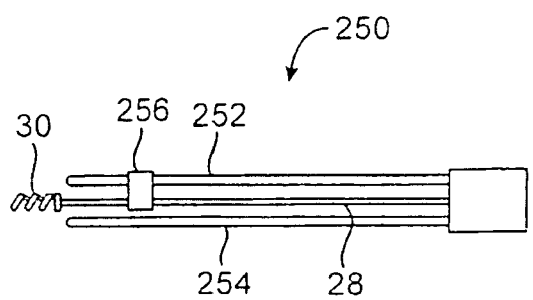
FIGS. 16A and 16B show side views of another variation where one or more extension members are configured to be passively biased.
Figure 16B:
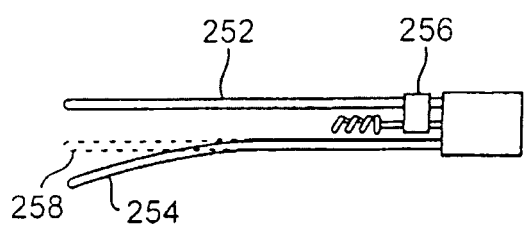

FIGS. 16A and 16B show yet another alternative in assembly 250 where upper extension member 252 and/or lower extension member 254 may be passively urged into an open configuration. In this example, lower extension member 254 is shown as being flexed from a relaxed configuration in FIG. 16A to a flexed configuration in FIG. 16B. As linear bearing 256 is withdrawn proximally, any tissue engaged to tissue grasper 30 may urge lower extension member 254 from its normal position 258 to its flexed and opened position. Accordingly, lower extension member 254 and/or upper extension member 252 may be made from a relatively flexible plastic or metallic material, e.g., Nitinol, spring stainless steel, etc. When tissue is removed from between the extension members 252, 254, lower extension member 254 may return to its normal configuration 258.

Figure 17B:
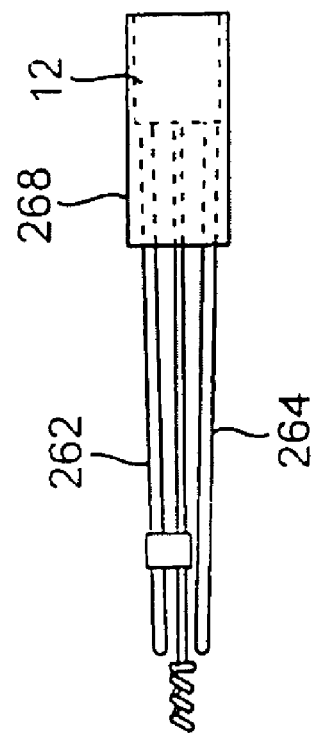
FIGS. 17A and 17B show side views of another variation of extension members which are actuatable via a translatable sleeve.
Figure 17A:
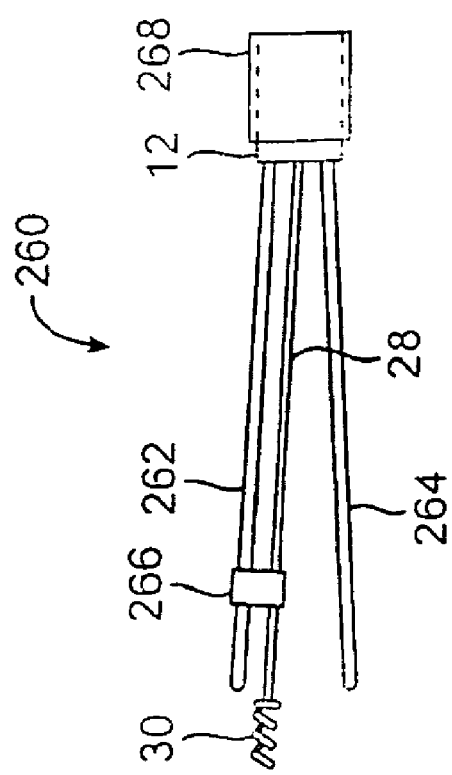

FIGS. 17A and 17B show side views of another assembly 260 in which upper and/or lower extension members 262, 264 may be biased or configured to flex away from one another, as shown in FIG. 17A. Once linear bearing 266 and tissue grasper 30 has been retracted, an outer sleeve 268 slidingly disposed over tubular body 12 may be pushed distally such that sleeve 268 is slid over at least a proximal portion of extension members 262, 264 such that they are urged towards one another into a closed configuration onto tissue which may be present therebetween, as shown in FIG. 17B.

Figure 18:
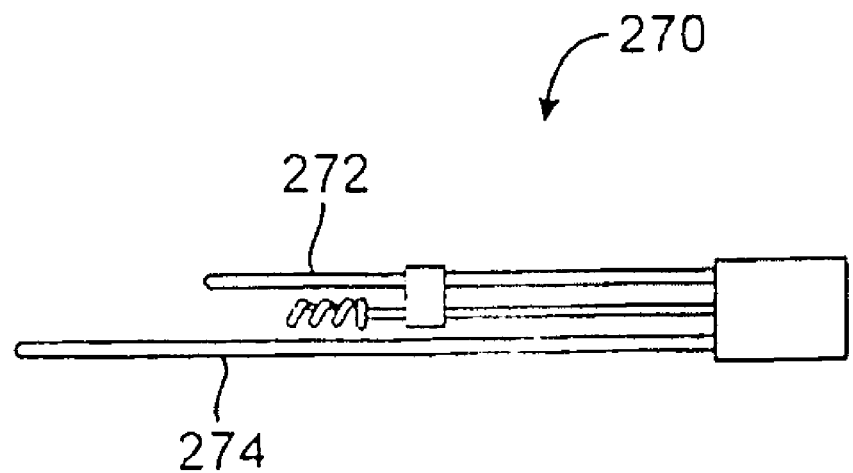
FIG. 18 shows a side view of a tissue manipulation assembly with a lower extension member having a longer length than the upper extension member.

Aside from features such as articulation of the extension members, the extension members themselves may be modified. For instance, FIG. 18 shows a side view of extension assembly 270 where lower extension member 274 may be extended in length relative to upper extension member 272. The length of lower extension member 274 may be varied depending upon the desired result. Alternatively, upper extension member 272 may be shortened relative to lower extension member 274. The lengthening of lower extension member 274 may be utilized to present a more stable platform for tissue approximated between the extension members 262, 264.

Figure 19:
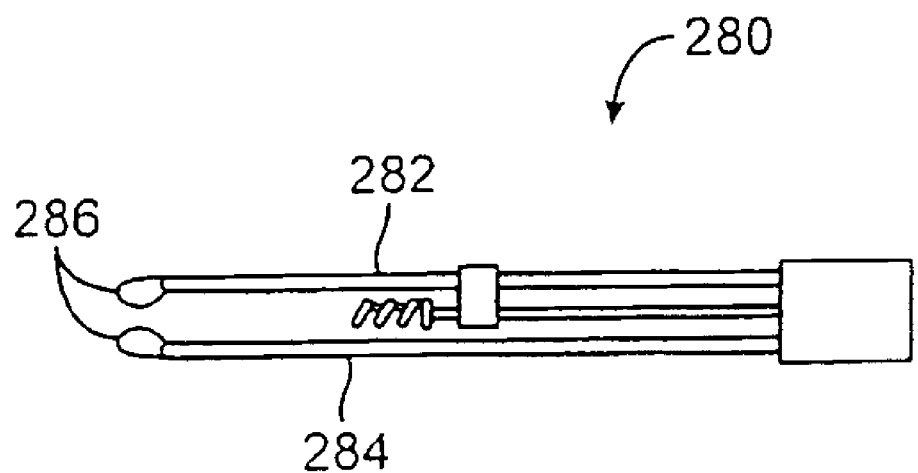
FIG. 19 shows a side view of another variation where one or both extension members may have tips atraumatic to tissue.

Another alternative for modifying the extension members is seen in the side view of FIG. 19 in extension assembly 280. In this example, one or both extension members 282, 284 may be configured to have atraumatic blunted ends 286 which may be further configured to be flexible to allow tissue to slide over the ends. Moreover, atraumatic ends 286 may be configured in a variety of ways provided that an atraumatic surface or feature is presented to the tissue.

In addition to atraumatic features, the lower extension member of the tissue manipulation assembly may be varied as well. For example, as the needle assembly and tissue anchors are deployed from the launch tube, typically from the upper extension member, it is preferable to have sufficient clearance with respect to the lower extension member so that unhindered deployment is facilitated. One method for ensuring unhindered deployment is via a lower extension member having a split opening defined near or at its distal end, as shown in the perspective view of tissue manipulation assembly 290 in FIG. 20A. Such a split may allow for any deployed anchors or suture an opening through which to be released from assembly 290.

Figure 20A:
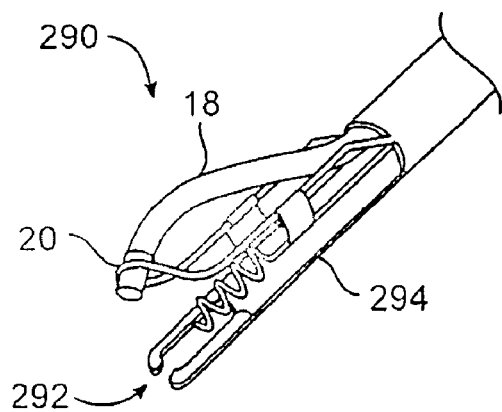
FIGS. 20A and 20B views of a variation of lower extension members which may be configured to be actuatable.
Figure 20B:
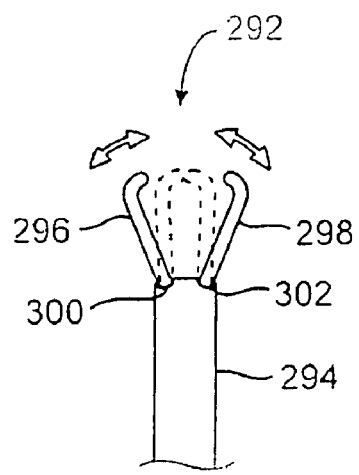

Additionally, the jaws which define the opening may be articulatable as well relative to lower extension member 294. As shown in the bottom view of FIG. 20B, articulatable lower extension assembly 292 may have one or both jaw members 296, 298 articulatable via pivots 300, 302, respectively, relative to lower extension member 294 such that one or both jaw members 296, 298 are able to be moved between a closed configuration, as shown in FIG. 20A, and an open configuration, as shown in FIG. 20B. This variation in assembly 290 may allow for any needle or anchor assemblies to easily clear lower extension member 294.

Figure 20C:
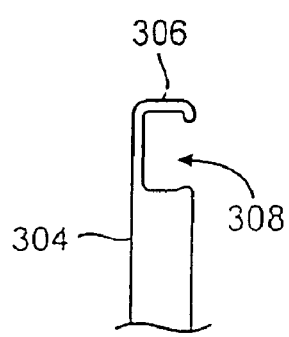
FIG. 20C show a top view of a lower extension member which may be configured into a "C" shape.

Another variation of lower extension member 304 is shown in the bottom view of FIG. 20C. In this variation, an enclosing jaw member 306 may extend from lower extension member 304 such that an opening 308 along either side of extension member 304 is created. Such an opening 308 may create a "C"-shaped lower extension member 304 which may facilitate needle and anchor deployment from the tissue manipulation assembly.

Figure 21A:
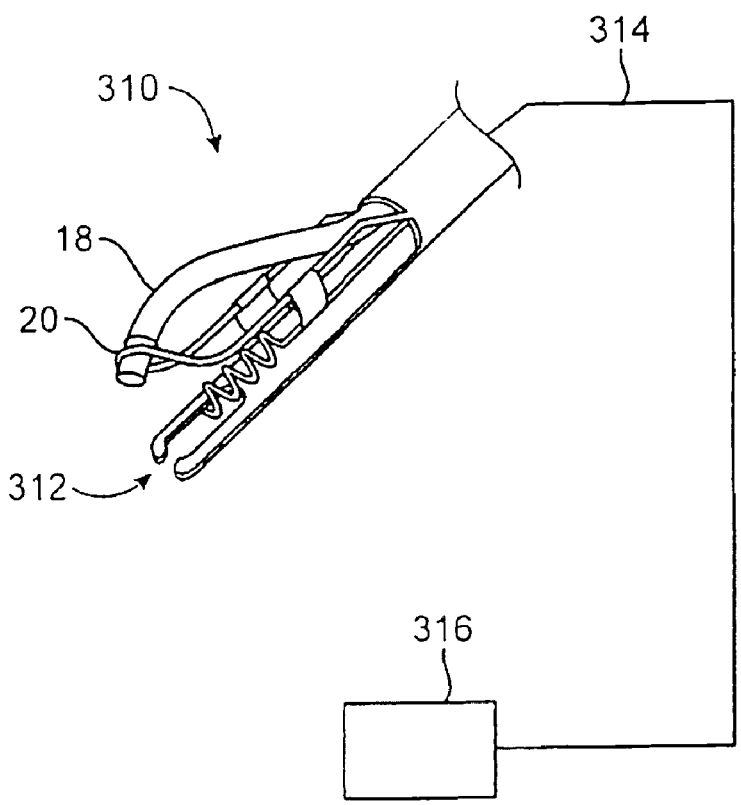
FIGS. 21A and 21B show perspective and top views of a lower extension member having one or more energize-able wires disposed thereon for tissue ablation.
Figure 21B:
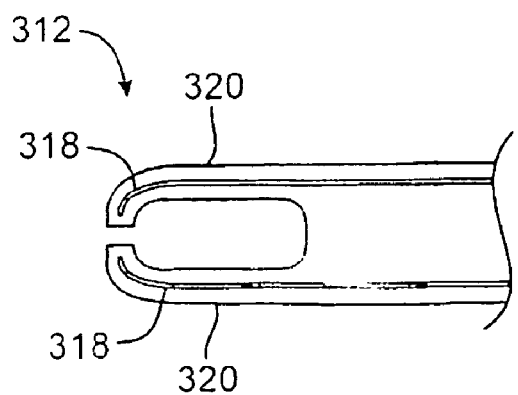

Another variation of a tissue manipulation assembly 310 may be seen in the illustrative partial perspective view of FIG. 21A. In addition to articulation or release features, one or both extension members may be utilized to selectively ablate regions of tissue. Assembly 310 for instance may have a tissue ablation assembly 312 integrated into the lower extension member 320. Such a tissue ablation assembly 312, as seen in the top view of FIG. 21B, may incorporate one or more wires or electrically conductive elements 318 upon lower extension member 320 to create a tissue ablation region. The lower extension member 320 may be fabricated from a non-conductive material upon which wires 318 may be integrated. Alternatively, the entire lower member 320 may be electrically conductive with regions selectively insulated leaving non-insulated areas to create ablation regions 318. The wires or regions 318 may be electrically connected via wires 314 to power source 316, which may provide various forms of energy for tissue ablation, e.g., radio-frequency, microwave, etc.

One example for use of the ablative tissue manipulation assembly may be seen in FIGS. 22A to 22E where tissue approximation assembly 330 may be seen with tissue manipulation assembly 14 advanced through an optional shape-lockable overtube 332. Ablation region 318 is integrated into the lower extension member 320 of the tissue manipulation assembly, as above. Alternatively, region 318 may, for example, comprise an abrasive surface disposed on lower extension member 320. Alternatively, the lower extension member 320 may comprise an ablation electrode for injuring mucosal tissue.

Figure 22A:
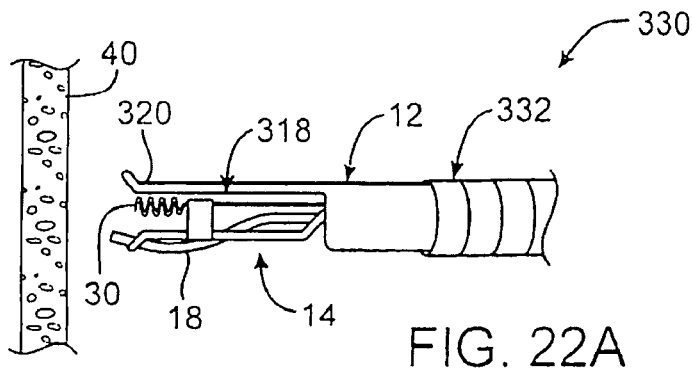
FIG. 22A is a detail side view of an ablative tissue manipulation assembly advanced through a shape-lockable overtube and positioned adjacent to a tissue wall.
Figure 22B:
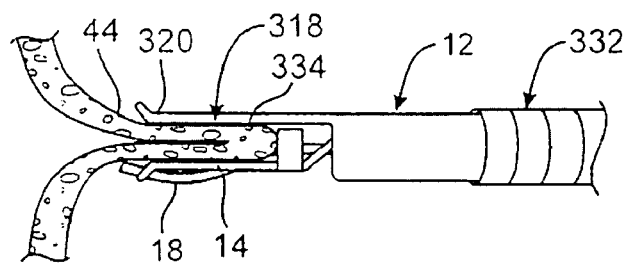
FIG. 22B is detail side view of assembly shown in FIG. 22A forming a tissue fold.
Figure 22C:
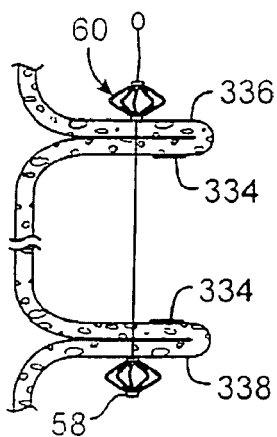
FIG. 22C is a detail side view of additional tissue folds prepared to be approximated together.
Figure 22E:
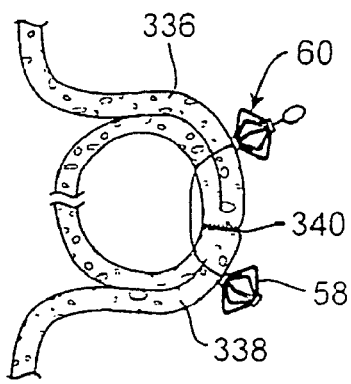
FIG. 22E is a detail side view of the approximated tissue folds shown in FIG. 22D now fused together.
Figure 22D:
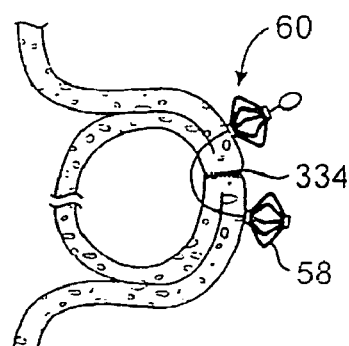
FIG. 22D is detail side view of the tissue folds shown in FIG. 22C now approximated together.

As seen in FIG. 22B, when tissue wall 40 is folded between the extension members of assembly 14, target mucosal tissue 334 contacts lower extension member 320 as well as ablation region 318. Passive or active actuation of ablation region 318 may then injure and/or remove the target mucosal tissue 334. As further seen in FIG. 22C, this procedure may be repeated at one or more additional tissue folds 336, 338 that may then be approximated together, as in FIG. 22D. The contacting injured regions of mucosal tissue promote healing and fusion 340 of the approximated folds, as in FIG. 22E.

Figure 23A:
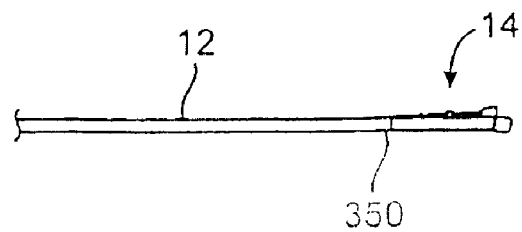
FIGS. 23A to 23C show side views of a tissue manipulation assembly which may be configured to articulate into an angle relative to the tubular body.
Figure 23B:
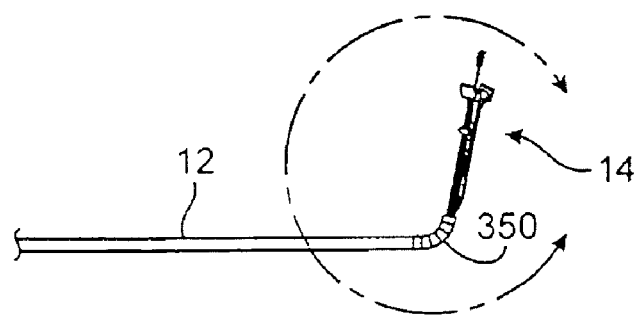
Figure 23C:
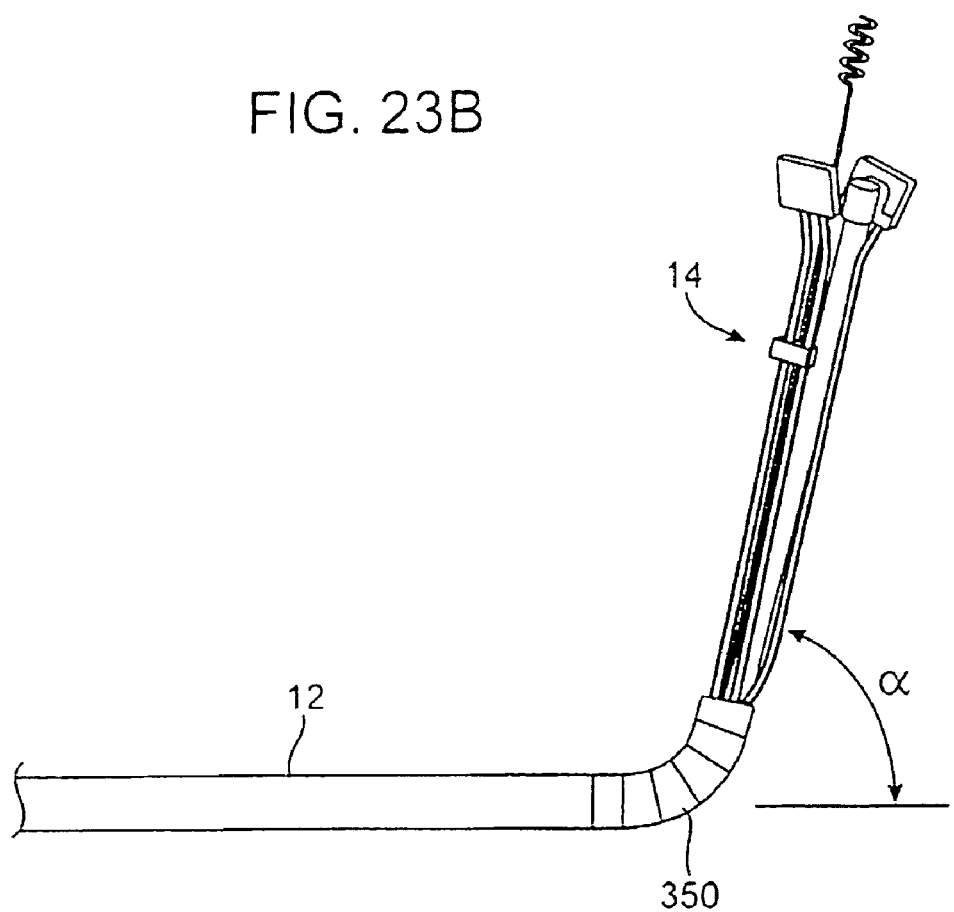

Aside from variations on aspects of the tissue manipulation assembly, the entire assembly may also be modified to adjust the tissue manipulation assembly position relative to the tubular body upon which the assembly is attachable. FIG. 23A shows a distal portion of tubular body 12 and tissue manipulation assembly 14 connected thereto. While tubular body 12 may comprise a rigid or flexible length, tissue manipulation assembly 14 may be further configured to articulate relative to tubular body 12, as shown in FIG. 23B, to further enhance the maneuverability and manipulation capabilities of tissue manipulation assembly 14. In one example, assembly 14 may be connected to tubular body 12 via a hinged or segmented articulatable portion 350, shown in the detail FIG. 23C, which allows assembly 14 to be reconfigured from a low-profile configuration straightened relative to tubular body 12 to an articulated configuration where assembly 14 forms an angle, .alpha., relative to tubular body 12. The angle, .alpha., may range anywhere from 180.degree. to −180.degree. depending upon the desired level of articulation. Articulatable portion 350 may be configured to allow assembly 14 to become articulated in a single plane or it may also be configured to allow a full range of motion unconstrained to a single plane relative to tubular body 12. Articulation of assembly 14 may be accomplished any number of various methods, e.g., control wires.

Any of the variations of the tissue manipulation assemblies or aspects of various features of the tissue manipulation assemblies is intended to be utilized in any number of combinations with other aspects of other variations as practicable. Moreover, any of the variations relating to the tissue manipulation assemblies may also be used in any number of combinations, as practicable, with the helix variations described above, if so desired.

Launch Tube

Figure 24A:
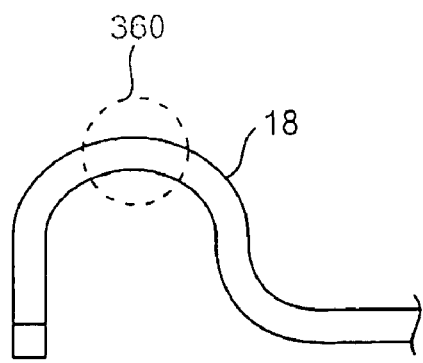
FIGS. 24A and 24B show side and perspective detail views, respectively, of a launch tube specially configured to flex in specified planes.

An illustrative side view of a partial launch tube 18 configured for anchor deployment may be seen in FIG. 24A. Launch tube 18 is typically configured to partially translate relative to the tissue manipulation assembly such that a distal portion of the launch tube 18 may be articulated perpendicularly to the tissue to be pierced. Launch tube 18 may be made from a variety of flexible materials which are flexible yet sufficiently strong to withstand repeated flexing of the tube.

Figure 24B:
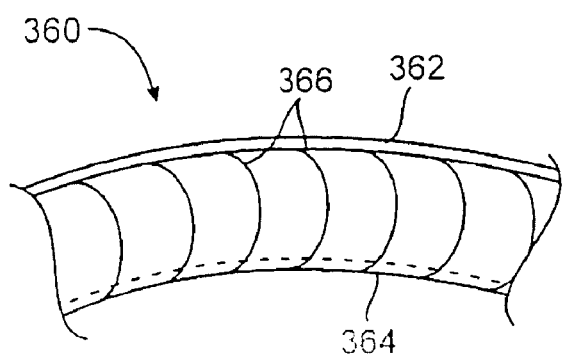

FIG. 24B shows a portion 360 of launch lube 18 which may be fabricated from a metal such as Nitinol, stainless steel, titanium, etc. To facilitate the flexure of tube 18, such a tube may be selectively scored or cut to enhance the directional flexibility of the tube 18. Accordingly, in one variation, a plurality of circumferential cuts or slits 366 may be made in the portion of launch tube 18 which is flexed. Cuts 366 may extend between one or more lengths or spines 362, 364 of uncut tube material which may extend over the length of the flexible portion. These spines 362, 364 in combination with the cuts 366 may facilitate the directional flexibility or bending of launch tube 18 in a singular bending plane. Cuts 366 may be made along the launch tube 18 using any number methods, e.g., mechanical cutting, laser cutting, chemical etching, etc.

Figure 24C:
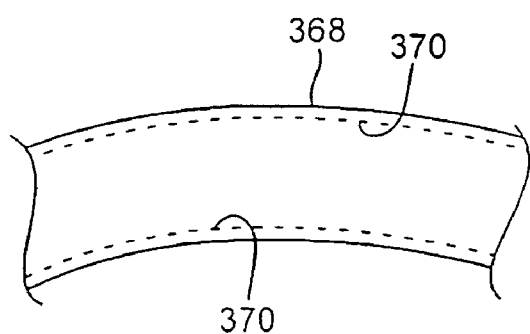
FIGS. 24C and 24D show side views of a portion of the launch tube having one or more coatings or coverings.
Figure 24D:
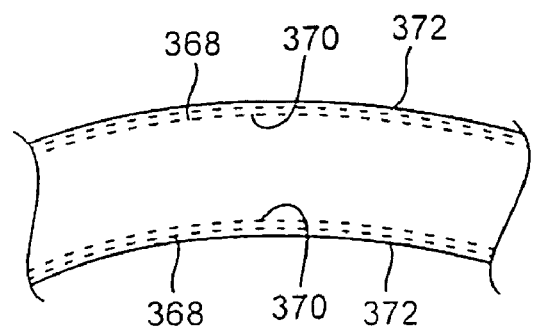

Another variation of launch tube 18 is shown in the partial views of FIGS. 24C and 24D. Launch tube wall 368 may be seen in FIG. 24C with an optional inner covering or coating 370 while FIG. 24D shows another variation of launch tube wall 368 with an optional additional outer coating 372. Inner covering or coating 370 may be comprised of a lubricious material, e.g., PTFE, etc., to facilitate the ease with which the needle assembly may be advanced or withdrawn through launch tube 18. Moreover, outer covering or coating 372 may also comprise a lubricious material to facilitate the translation of launch tube relative to tubular body 12. Either or both coatings 370, 372 may also ensure the structural integrity of launch tube 18 as well.

Figure 25:
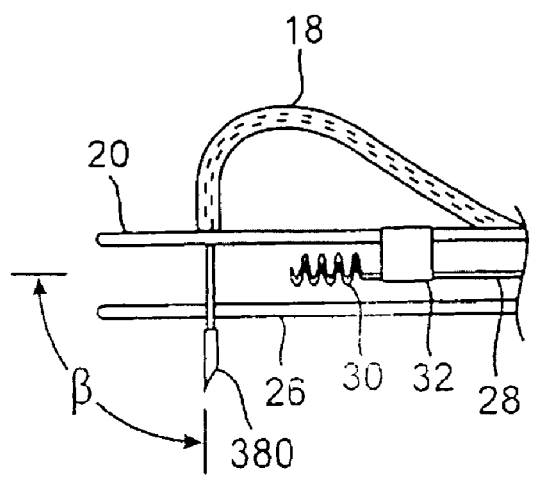
FIG. 25 shows an illustrative side view of the angle formed between the deployed needle assembly and a longitudinal axis of the tissue manipulation assembly.

In advancing launch tube 18 into a configuration where its distal opening is transverse to the tissue to be pierced, launch tube 18 is preferably advanced until the deployed needle body 380 of the needle assembly emerges from launch tube 18 perpendicularly to the tissue drawn between the extension members, and particularly to upper extension member 20. Thus, the distal opening of launch tube 18 may be configured to form an angle, .beta., relative generally to the tissue manipulation assembly, as shown in FIG. 25. Angle, .beta., is preferably close to 90.degree. but it may range widely depending upon the amount of tissue grasped as well as the angle desired; thus, the launch tube 18 may be configured to translate over a specified distance via detents or locks to ensure the formed angle.

Figure 26A:
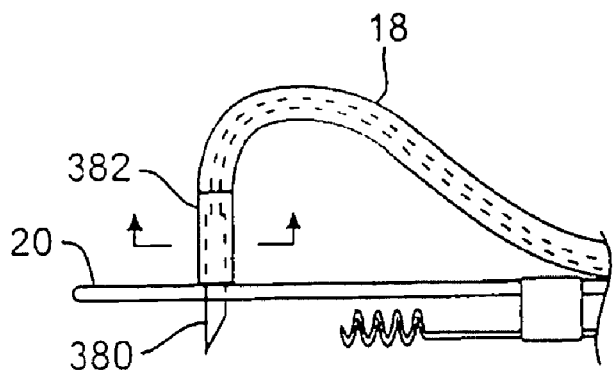
FIG. 26A shows a partial side view of a launch tube variation having an extended launch tube distal portion for aligning the needle body for deployment.

Aside from ensuring the deployment angle, .beta., of launch tube 18, a distal portion of launch tube 18 may be modified to include an extended portion 382 which is configured to remain straight even when launch tube 18 is flexed into its deployment configuration, as shown in FIG. 26A. Extended portion 382 may comprises an uncut portion of launch tube 18 or it may alternatively comprise a strengthened region of the launch tube 18. In either case, the extended portion 382 may provide additional columnar support to needle body 380 during needle deployment from launch tube 18 to help ensure the linear deployment of the needle body 380 into or through the tissue.

Figure 26B:
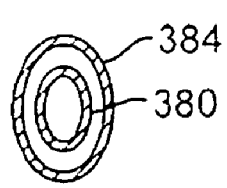
FIGS. 26B and 26C show cross-sectional views of the needle body and launch tube distal portion having various keyed cross-sectional areas.
Figure 26C:
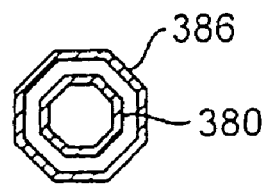

Another variation for needle deployment from launch tube 18 may be seen in the cross-sectional views of FIGS. 26B and 26C, which show the needle body 380 positioned within the distal portion 382 of launch tube 18. To ensure deployment of needle body 380 in a perpendicular or desired trajectory, needle body 380 may define a cross-sectional shape, other than circular, which is keyed to the extended distal portion 382 of launch tube 18. Thus, needle body 380 may define an elliptical cross-sectional shape within a complementary elliptically-shaped distal portion 384, as seen in FIG. 26B. Alternatively, needle body 380 may be configured into a polygonal shape, e.g., octagonal, within an octagonally-shaped distal portion 386, as seen in FIG. 26C. Any number of other cross-sectional shapes may be employed, e.g., rectangles, hexagons, heptagons, octagons, etc.

Figure 27A:
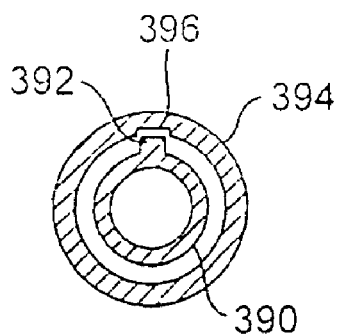
FIG. 27A shows another cross-sectional view where the needle body may be keyed to the launch tube.
Figure 27B:
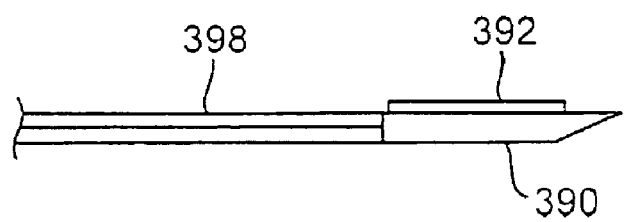
FIG. 27B shows a side view of the keyed needle body of FIG. 27A.

Rather than utilizing various cross-sectional shapes, needle body 390 may instead be keyed to launch tube 394 to ensure a specified deployment trajectory of needle body 390 from keyed launch tube 394, as shown in the cross-sectional view of FIG. 27A. One variation for keying may include attaching or forming a key or projection 392, e.g., a length of wire, along one or more sides of needle body 390, as shown in the side view of needle body 390 and delivery catheter 398. Launch tube 394 may define a groove or channel 396 along an inner surface through which the key 392 on needle body 390 may travel within while maintaining an orientation of needle body 390 relative to launch tube 394.

Figure 28:
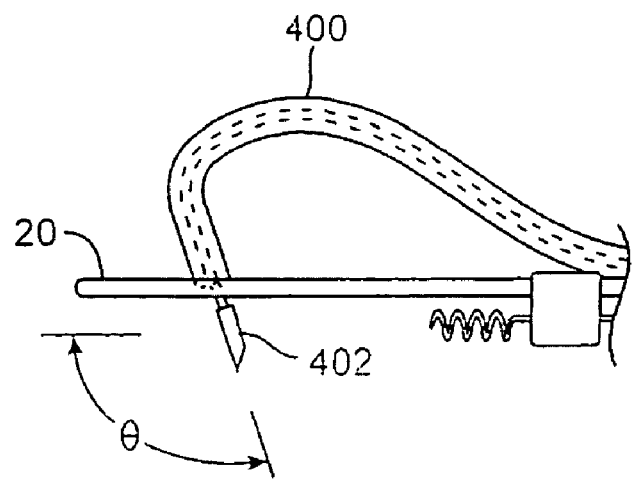
FIG. 28 shows a partial side view of an over-driven launch tube.

Yet another variation for ensuring needle trajectory from the launch tube may be seen in the partial cross-sectional view of FIG. 28. Various features of the tissue manipulation assembly have been omitted merely for clarity. As shown, launch tube 400 may be overdriven relative to the tissue manipulation assembly and upper extension member 20, i.e., the angle, .theta., formed between the deployed needle body 402 and upper extension member 20 is greater than 90.degree. The launch tube 400 and deployed needle body 402 may be overdriven to ensure that the trajectory of needle body 402 is directed towards the assembly rather than away from the assembly.

Any of the launch tube variations described herein is not intended to be limited to the examples described but is intended to be utilized in any number of combinations with other aspects of other variations as practicable. Moreover, any of the variations relating to the launch tube variations may also be used in any number of combinations, as practicable, with variations of other features as described above, if so desired.

Needle Body

Figure 29A:
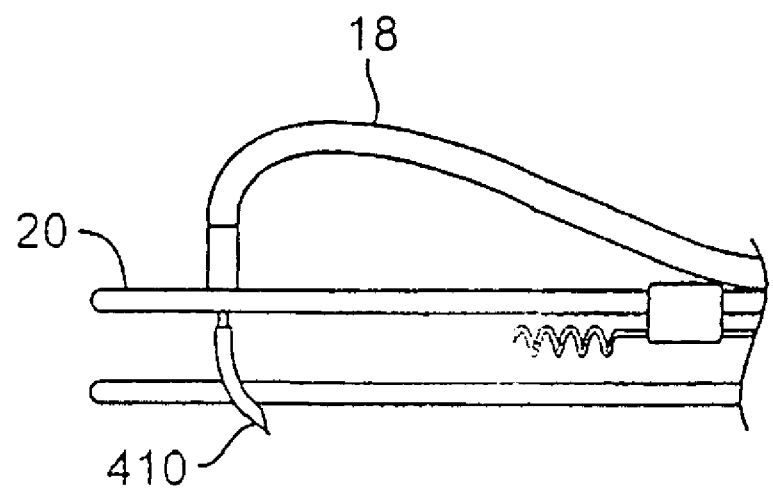
FIGS. 29A and 29B show partial side views of an assembly having curved deployable needle assemblies.

Generally, the launch tube needle is preferably a hollow tapered needle body which is configured to pierce into and through tissue. The needle body may have a variety of tapered piercing ends to facilitate its entry into tissue. One variation which may be utilized to ensure the needle trajectory through the tissue may be seen in FIG. 29A, which shows curved or curvable needle body 410 deployed from launch tube 18.

Figure 29B:
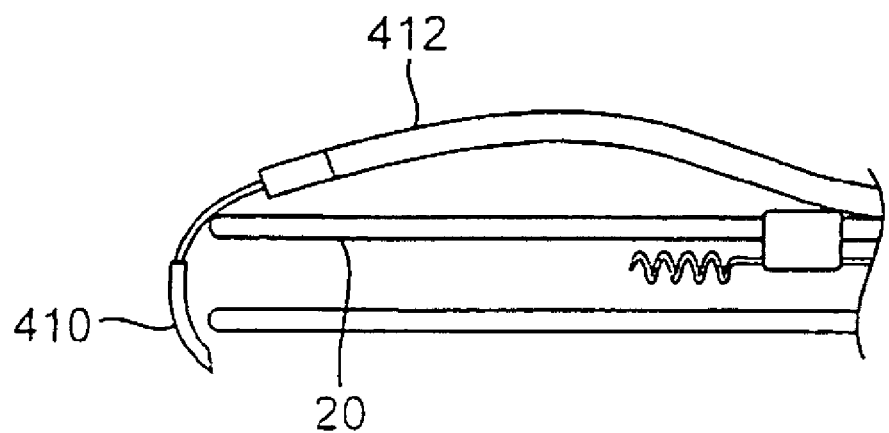

In this variation, needle body 410 may be constrained into a straightened configuration when positioned within launch tube 18. However, once deployed from launch tube 18, needle body 410 may be adapted to reconfigure itself into a curved configuration directed towards the tissue manipulation assembly. Thus, curved needle body 410 may be made from a super elastic alloy or shape memory alloy such as Nitinol. FIG. 29B shows another variation in which curved needle body 410 may be launched from an under-deployed launch tube 412.

Figure 30:
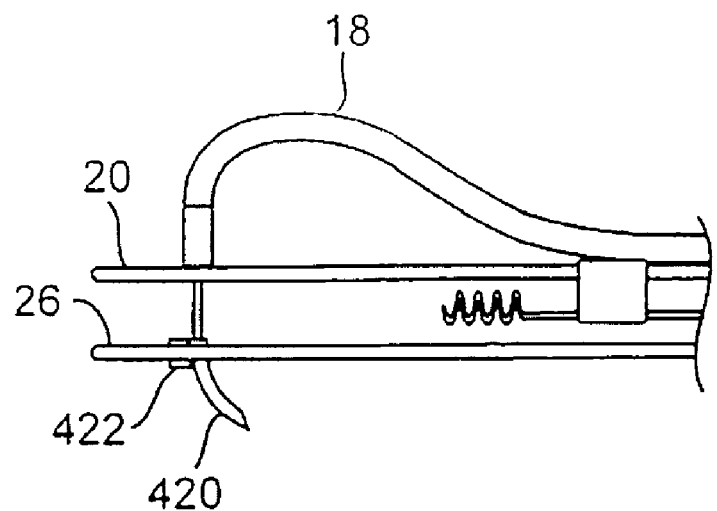
FIG. 30 shows a variation where the needle body may be curved via an anvil.

Another variation for curving the needle body is illustrated in the side view of FIG. 30. In this variation, needle body 420 may be curved via an anvil 422 configured to receive and deflect the travel of needle body 420 into a curved needle body. Needle body 420 may be comprised of a super elastic alloy such as Nitinol. Anvil 422 may be mounted on either lower extension member 26, as shown in the figure, or upper extension member 20, depending upon the desired results.

Figure 31:
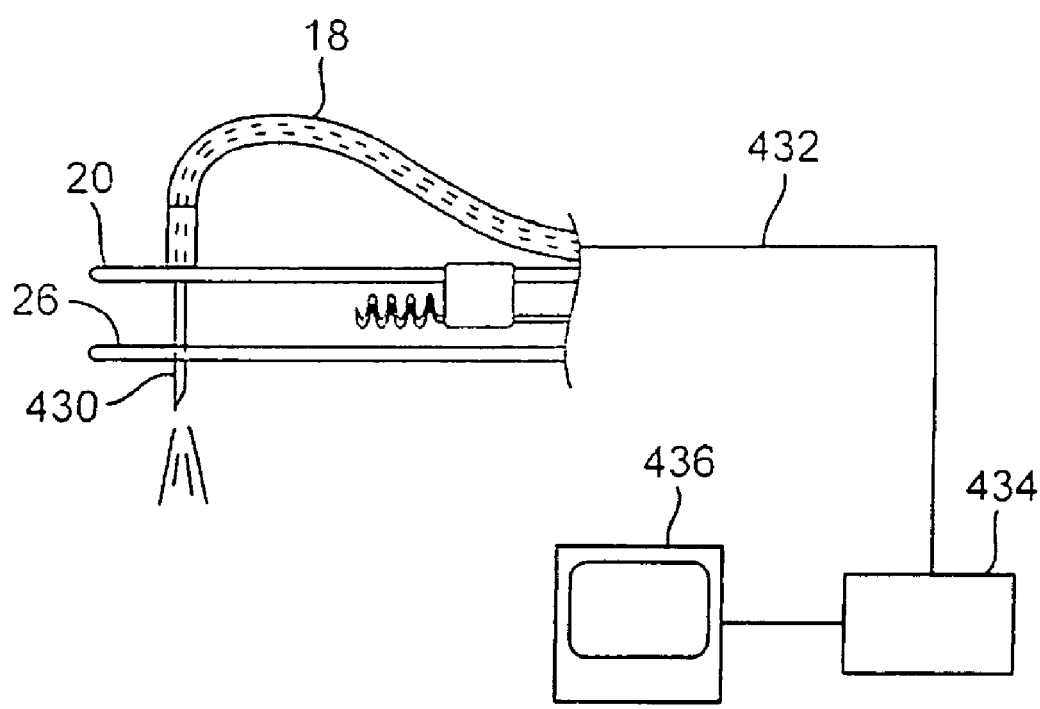
FIG. 31 shows another variation in which an optical fiber or an optical fiber configured as a needle body may be advanced through a launch tube to provide visualization.

Yet another variation of the needle body may be seen in the illustrative side view of FIG. 31 where the needle body may be replaced with a fiber optic needle 430. Such a needle 430 may be deployed through the launch tube 18 to provide visualization of the tissue region prior to, during, or after anchor deployment. Alternatively, fiber optic needle 430 may be advanced directly into or through the tissue region for visualization of the tissue. As shown, fiber optic needle 430 may be in communication via fiber optic wire or wires 432 to a processor 434 and an optional monitor 436 for viewing the tissue region from outside the patient's body.

Figure 32:
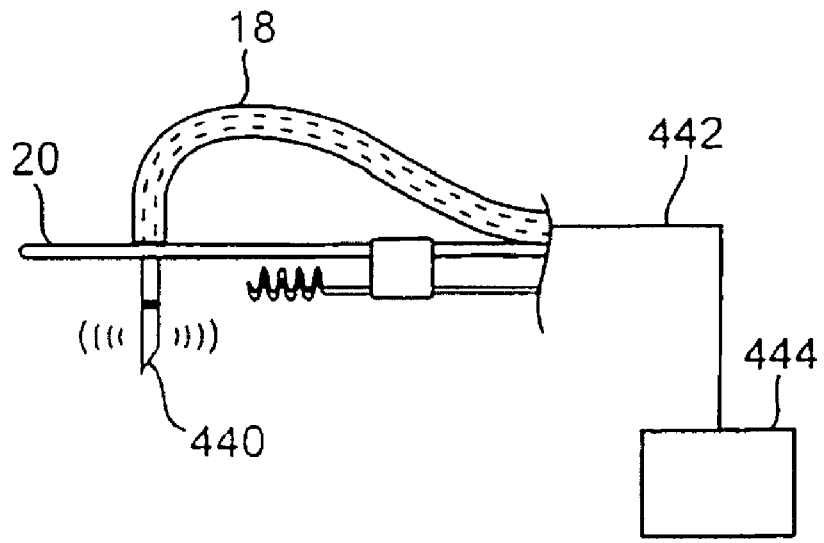
FIG. 32 shows a variation of the needle body which may be ultrasonically actuated.

In another alternative, advancement of the needle body into and/or through the tissue may be facilitated via an ultrasonic vibrating needle body 440, as shown in FIG. 32. Vibrating needle body 440 may be electrically connected via wires 442 to power source 444 for driving the needle body, e.g., using a piezoelectric transducer to supply the vibratory motion.

Figure 33:
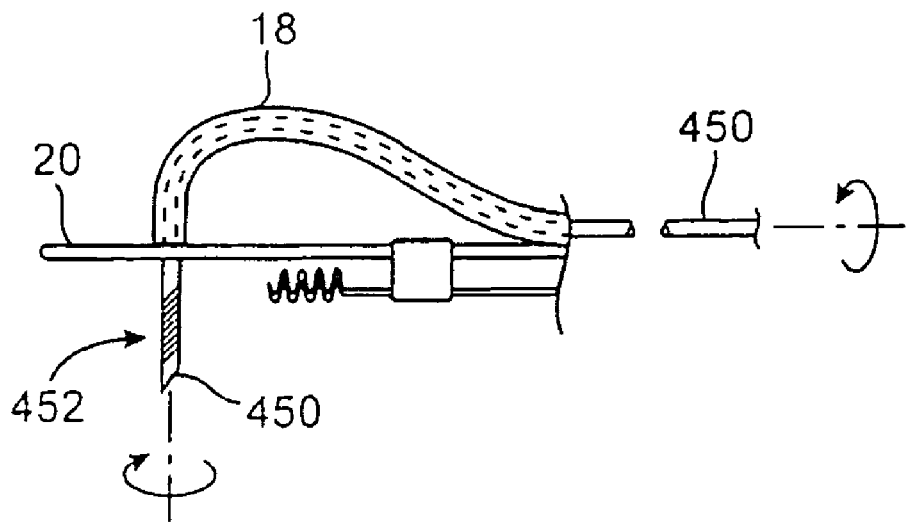
FIG. 33 shows a torqueable variation of the needle body.

FIG. 33 illustrates yet another alternative where rather than utilizing a vibrating needle body, a torqueable needle body 450, which may be torqued about its proximal end, may be utilized to facilitate entry into the tissue. The torqueable needle body 450 may be connected via a catheter length having high-torque characteristics, e.g., via braiding along the catheter shaft. Moreover, needle body 450 may further define threading 452 over its outer surface to facilitate entry of the needle body 450 into the tissue. To remove the needle body 450 from the tissue, the direction of torque may simply be reversed while pulling proximally on needle body 450.

Figure 34A:
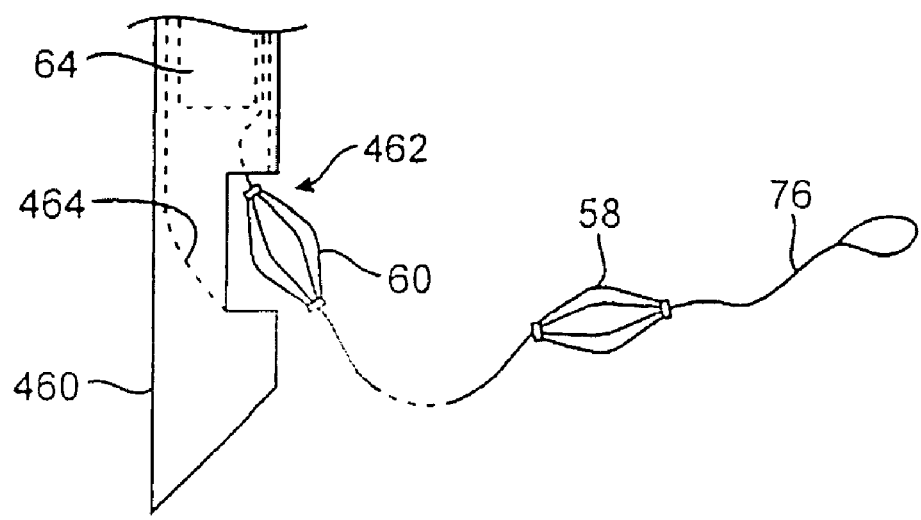
FIGS. 34A and 34B show needle body variations which may be configured to deploy tissue anchors via a side opening.
Figure 34B:
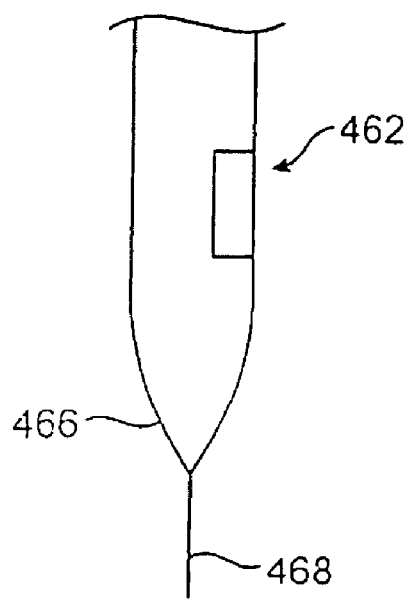

Rather than deploying anchors from the needle assembly via a distal opening in the needle body, the tissue anchor may alternatively be deployed through one or more side openings defined proximally of the distal tip of the needle body. As seen in the detail view of alternative needle body 460 in FIG. 34A, tissue anchor 60 may be deployed from needle body 460 through side opening 462. A ramp or taper 464 may be defined within needle body 460 leading to side opening 462 to facilitate the ejection of the tissue anchors from needle body 460. FIG. 34B shows another alternative needle body 466 having a side opening 462. This variation, however, includes a tapered needle body with needle knife 468 projecting distally from needle body 466. Needle knife 468 may be utilized to facilitate the initial entry into the tissue while tapered needle body 466 may be used to dilate the opening created by needle knife 468 and facilitate the entry of needle body 466 into and/or through the tissue.

Another variation on the needle body and launch tube is shown in FIGS. 35A to 36C. FIG. 35A shows an end view looking directly along tubular body 12 towards the tissue manipulation assembly with the launch tube 470 flexed into its deployment configuration. FIGS. 35B and 35C show the end view of FIG. 35A where the assembly is angled relatively to the left and to the right, respectively. The terms "left" and "right" are intended to refer only to the orientation of the assembly as shown in the figures and are used for illustrative purposes. FIG. 36A shows a top view of the assembly corresponding to FIG. 35A while FIGS. 36B and 36C also show top views corresponding to FIGS. 35B and 35C, respectively. When the tissue assembly is visualized within the patient's body via a laparoscope or endoscope, determining the orientation of the assembly with respect to the tissue may at times be difficult typically due to the lack of depth perception. Thus, to aid with orientation of the assembly when oriented at some angle, .omega., as shown in FIGS. 35B, 35C, 36B and 36C, portions of the assembly, such as launch tube 470 or the needle assembly, may be coated or covered with a color, e.g., red, orange, yellow, green, blue, indigo, violet, silver, black, or combinations thereof. The aid of coloring portions of the assembly may help with gaining orientation of the device.

Aside from coloring the tissue manipulation assembly, portions of the needle assembly may also be colored as well. FIG. 37A shows a needle body 480 which may be colored with any of the colors described above to facilitate orientation of the needle body 480 when deployed from the launch tube. In another alternative, needle body 482 may have gradations or indicators 484 along its surface, as shown in FIG. 37B, to provide a visual indication to the surgeon or physician of the position of needle body 482 when advanced into or through the tissue or when deployed from the launch tube. Each of the gradations 484 may be separated by a uniform distance or various positions along the needle body 482 may be marked to indicate specified locations.

Figure 37C:
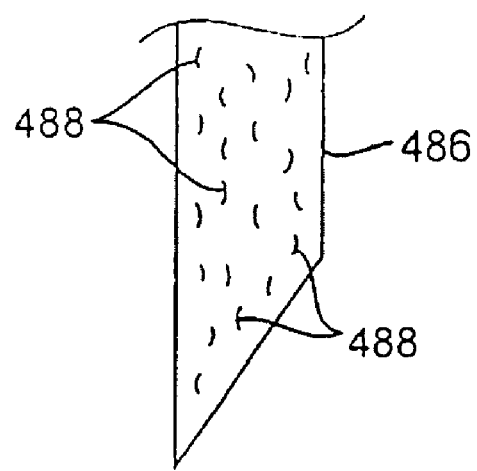

FIG. 37C shows yet another variation in which the outer surface of needle body 486 may be dimpled 488. The presence of dimples 488 may be used to enhance the visualization of needle body 486 within the patient body. Moreover, dimples 488 may also enhance the visualization of needle body 486 under ultrasound imaging, if utilized, either for imaging the position of needle body 486 or for locating needle body 486 within the patient's body if the needle body 486 were to inadvertently break off.

Figure 37D:
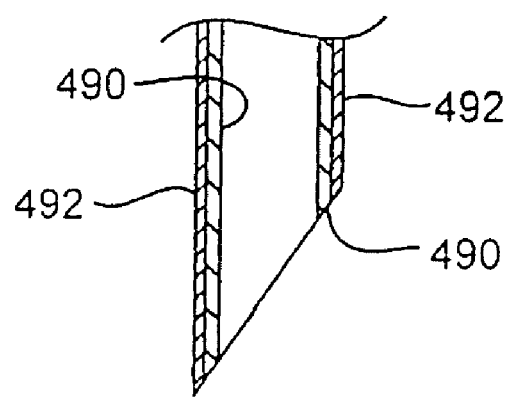

Yet another variation is shown in the cross-sectional view of needle body 490 in FIG. 37D. The outer surface of needle body 490 may be coated or covered with a radio-opaque material 492 to further enhance visualization of the needle body 490, for example, if x-ray or fluoroscopic imaging were utilized. The radio-opaque coating 492, e.g., platinum, nickel, etc., may also be further coated with a lubricious material to facilitate needle insertion into and/or through the tissue.

Any of the needle body and needle assembly variations described herein is not intended to be limited to the examples described but is intended to be utilized in any number of combinations with other aspects of other variations as practicable. Moreover, any of the variations relating to the needle body variations may also be used in any number of combinations, as practicable, with variations of other features as described above, if so desired.

Handle Assembly

The tissue manipulation assembly may be manipulated and articulated through various mechanisms. One such assembly which integrates each of the functions into a singular unit may be seen in the handle assembly which is connected via tubular body 12 to the tissue manipulation assembly. Such a handle assembly may be configured to separate from tubular body 12, thus allowing for reusability of the handle. Moreover, such a handle may be fabricated from a variety of materials such as metals or plastics, provided that the materials are preferably biocompatible. Examples of suitable materials may include stainless steel, PTFE, Delrin®, etc.

Figure 38A:
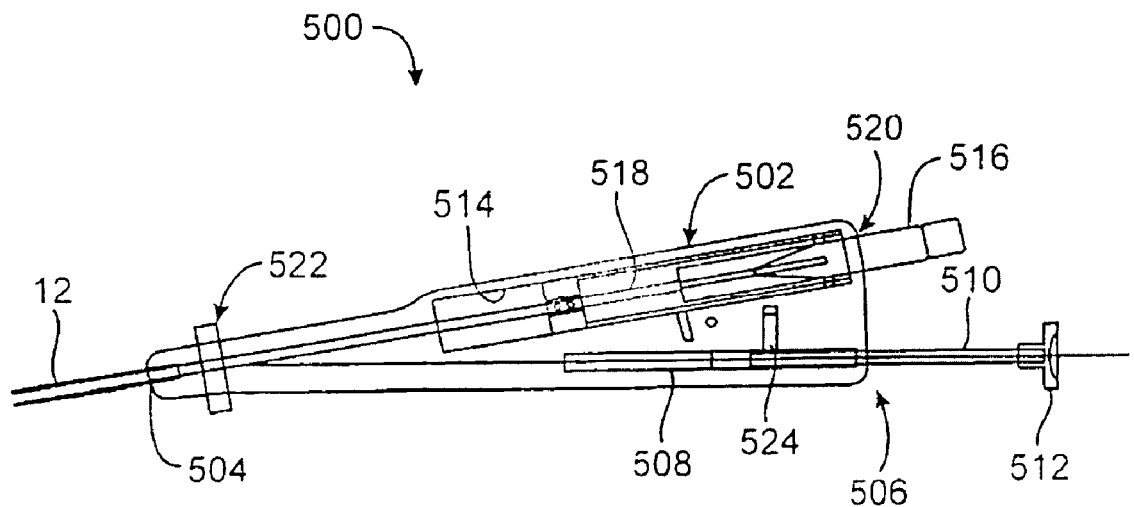
FIGS. 38A to 38C show partial side views of variations of a handle for controlling and articulating the tissue manipulation assembly.

One variation of a handle assembly is shown in the illustrative side view of handle 500 in FIG. 38A with half of handle enclosure 502 removed for clarity for discussion purposes. As shown, handle enclosure 502 may connect with tubular body 12 at its distal end at tubular interface 504. The proximal end of handle 500 may define acquisition member opening 506 which opens to acquisition member receiving channel 508 defined through enclosure 502 from opening 506 to tubular interface 504. The acquisition member 28 may be routed through receiving channel 508 with the proximal end 510 of acquisition member 28 extending proximally of enclosure 502 for manipulation by the user. Acquisition member proximal end 510 may further have an acquisition member rotational control 512 that the user may grasp to manipulate acquisition member 28.

Acquisition member receiving channel 508 preferably has a diameter which is sufficiently large enough to allow for the translational and rotational movement of acquisition member through the receiving channel 508 during tissue manipulation. Acquisition member lock 524, e.g., a screw or protrusion, may also extend at least partially into acquisition member receiving channel 508 such that lock 524 may be urged selectively against acquisition member 28 to freeze a position of acquisition member 28, if so desired. The terminal end of receiving channel 508 may extend to tubular interface 504 such that receiving channel 508 and tubular body 12 are in communication to provide for the passage of acquisition member 28 therethrough.

In addition to the acquisition member controls, the handle enclosure 502 may also provide a needle assembly receiving channel 514 through which needle assembly control 516 and needle assembly catheter 518 may be translated through. Needle assembly receiving channel 514 may extend from needle assembly opening 520 also to tubular interface 504. Needle assembly receiving channel 514 extends to tubular interface 504 such that needle assembly receiving channel 514 and tubular body 12 are also in communication to provide for the passage of needle assembly catheter 518 therethrough.

Figure 38B:
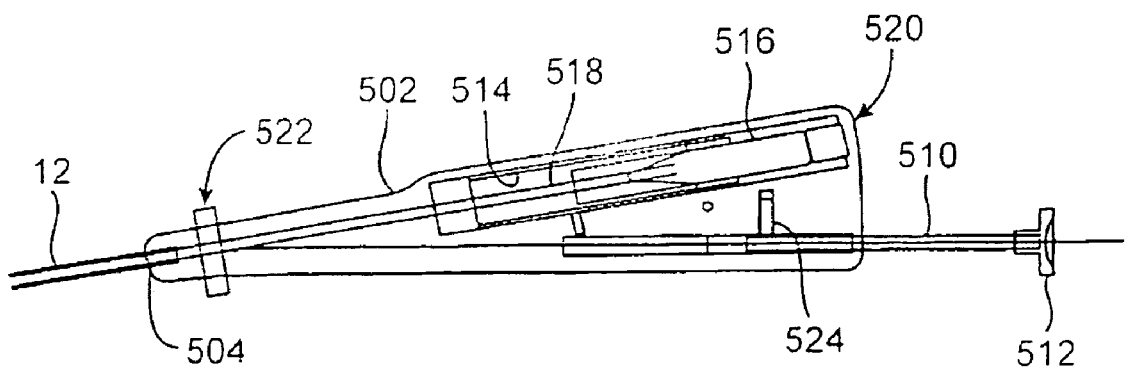

In operation, once the tissue to be plicated has been acquired and drawn between the lower and upper extension members by acquisition member 28, as described above, the launch tube 18 may be advanced distally and rotated into its deployment configuration. Once positioned for deployment, the needle assembly may be advanced into and/or through the tissue by urging needle assembly control 516 and needle assembly catheter 518 distally into needle assembly receiving channel 514, as shown by the advancement of control 516 in FIG. 38B. The tissue anchors may then be deployed from the needle assembly catheter 518 via the needle assembly control 516, as further described below. Withdrawal of the needle assembly from the tissue may be accomplished by the proximal withdrawal of needle assembly control 516 and assembly catheter 518.

Tissue manipulation articulation control 522 may also be positioned on handle 500 to provide for selective articulation of the tissue manipulation assembly, as shown above in FIGS. 23A to 23C. This variation shows articulation control 522 rotatably positioned on handle enclosure 502 such that articulation control 522 may be rotated relative to handle 500 to selectively control the movement of the tissue manipulation assembly. Articulation control 522 may be operably connected via one or several control wires attached between articulation control 522 and the tissue manipulation assembly. The control wires may be routed through tubular interface 504 and extend through tubular body 12.

Figure 38C:
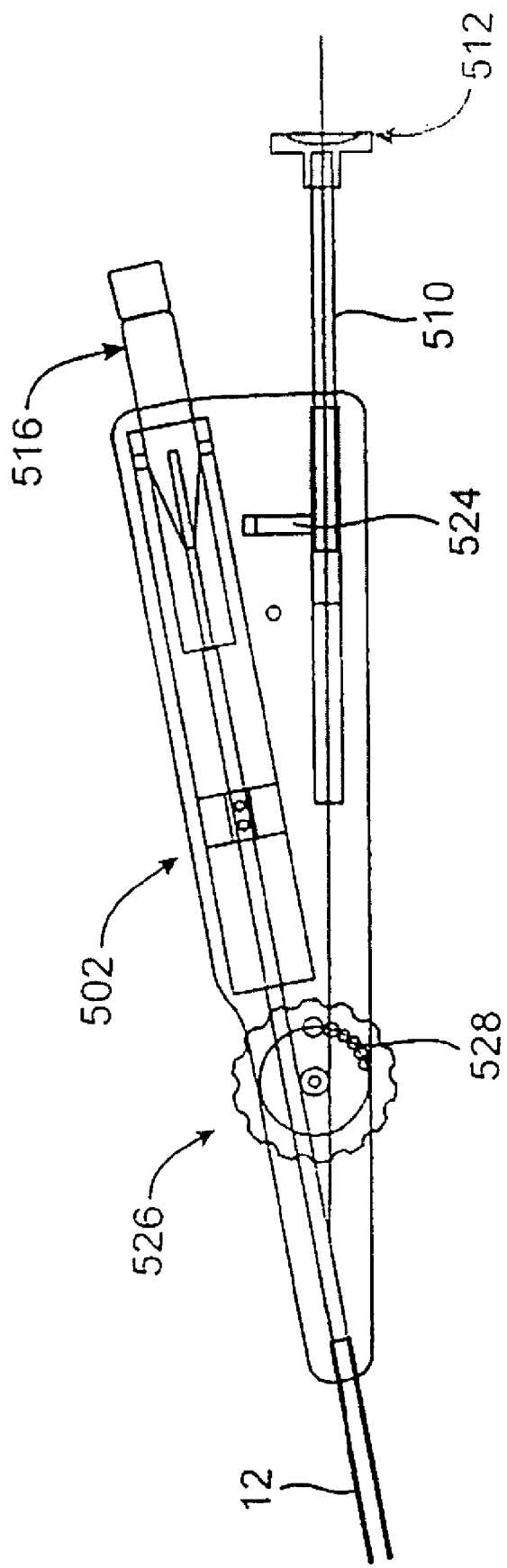

FIG. 38C shows another variation of handle enclosure 502 where the tissue manipulation articulation control 526 may be positioned on a side surface of handle enclosure 502. Articulation control 526 may include a ratcheting mechanism 528 within enclosure 502 to provide for controlled articulation of the tissue manipulation assembly.

Figure 39A:
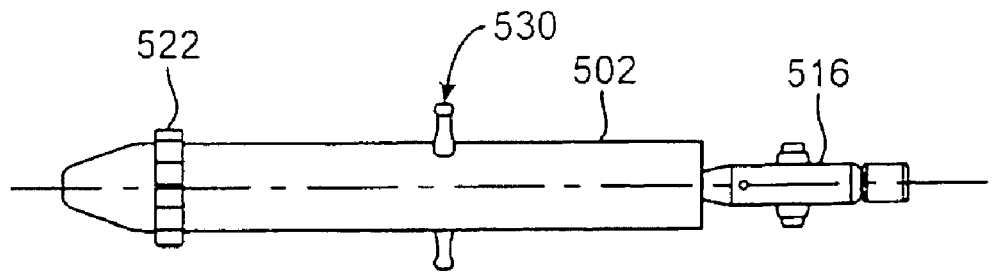
FIGS. 39A to 39C show top, side, and cross-sectional views, respectively, of another variation of a handle having a multi-position locking and needle assembly advancement system.
Figure 39B:
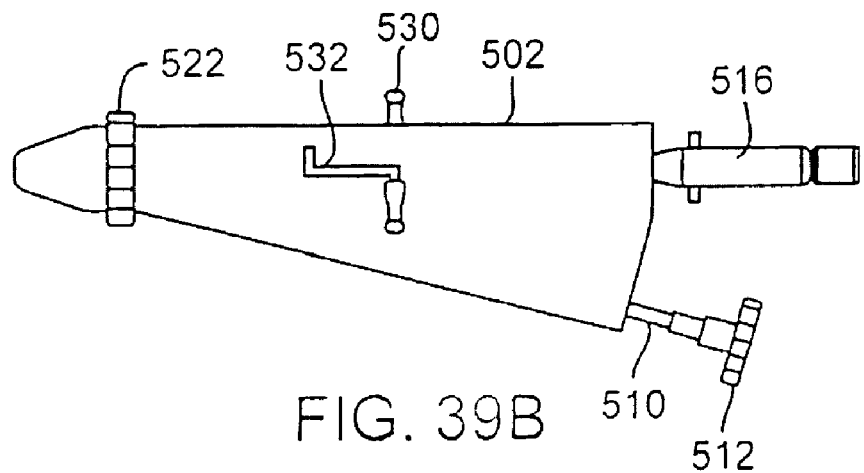
Figure 39C:
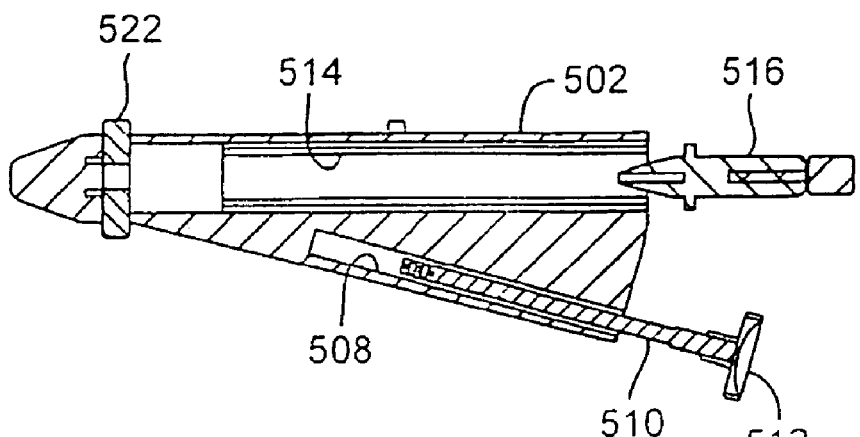

FIGS. 39A to 39C show top, side, and cross-sectional views, respectively, of another variation on the handle assembly. As seen in FIGS. 39A and 39B, an advancement control 530 may be adapted to selectively slide translationally and rotationally through a defined advancement channel or groove 532 defined within handle enclosure 502. Advancement control 530 may be used to control the deployment and advancement of needle assembly control 516 as well as deployment of the launch tube, as described in further detail below.

Figure 39D:
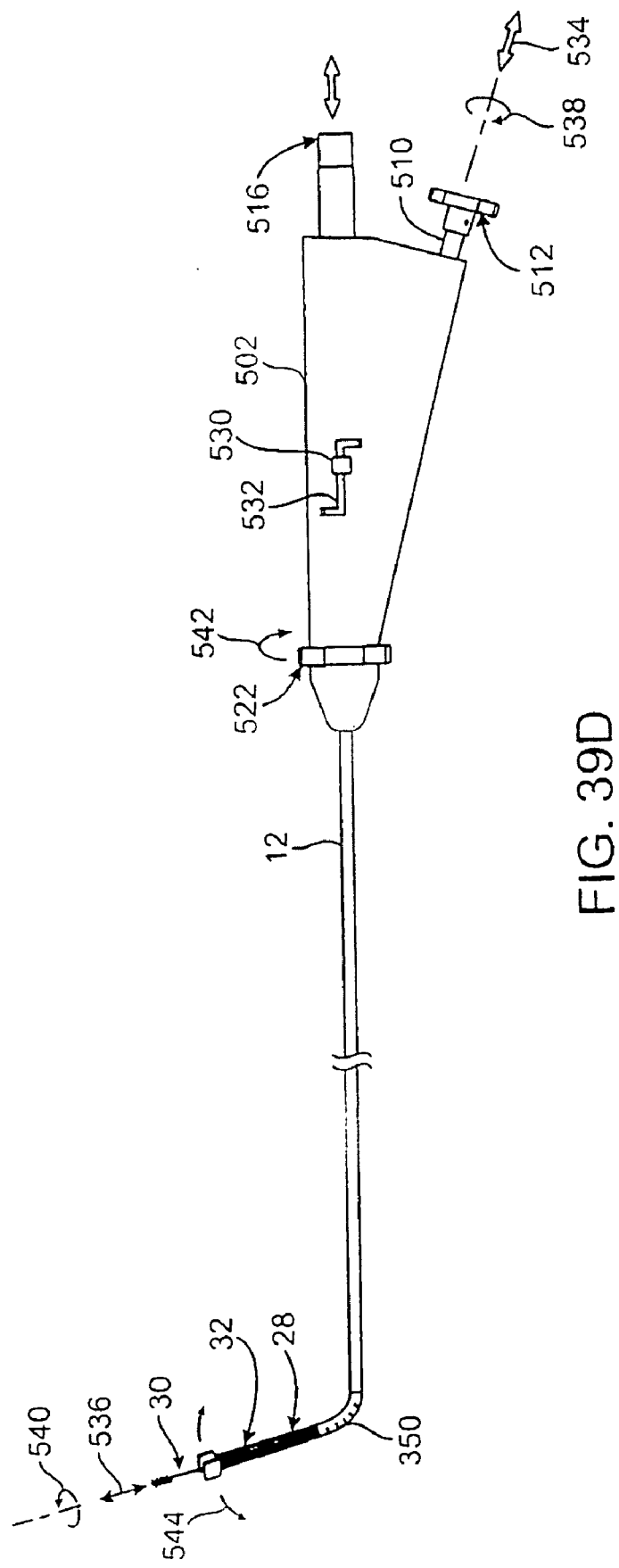
FIG. 39D shows an assembly view of the handle of FIG. 39A connected to the tissue manipulation assembly via a rigid or flexible tubular body or shaft.

FIG. 39D shows an assembly side view of the handle assembly, tubular body 12, and tissue manipulation assembly and the corresponding motion of the assembly when manipulated by the handle. As described above, tissue acquisition member proximal end 510 and acquisition member control 512 may be advanced or withdrawn from the handle enclosure 502 in the direction of arrow 534 to transmit the corresponding translational motion through tubular body 12 to tissue acquisition member 28 and tissue grasper 30, as indicated by the direction of corresponding arrow 536. Likewise, when acquisition member control 512 is rotated relative to handle enclosure 502, as indicated by rotational arrow 538, the corresponding rotational motion is transmitted through tubular body 12 to tissue grasper 30 for screwing into or unscrewing from tissue, as indicated by corresponding rotational arrow 540. As mentioned above, tubular body 12 may be rigid or flexible depending upon the application utilized for the device.

Likewise, longitudinal translation of needle assembly control 516 relative to enclosure 502, as indicated by the arrow may transmit the corresponding longitudinal motion to the needle assembly through the launch tube when reconfigured for deployment. The tissue manipulation assembly articulation control 522 may also be seen in this handle variation as being rotatable in the direction of arrow 542 relative to handle enclosure 502. Depending upon the direction of articulation, control 522 may be manipulated to elicit a corresponding motion from the tissue manipulation assembly about hinge or articulatable section 350 in the direction of arrows 544.

Figure 40A:
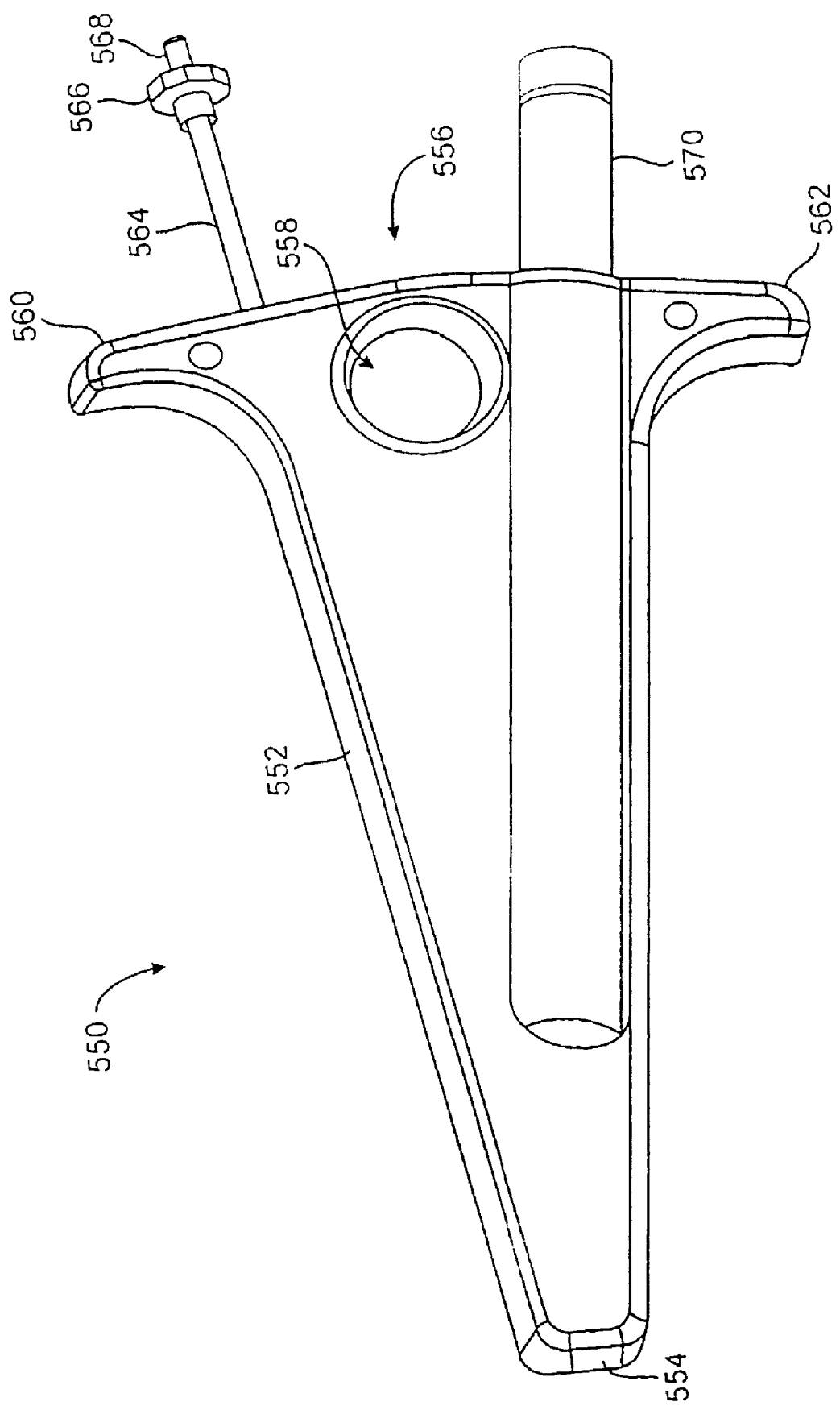
FIGS. 40A and 40B show perspective and cross-sectional views, respectively, of another variation of a handle having a reversible configuration.

Another handle variation may be seen in the perspective view of handle assembly 550, as shown in FIG. 40A. This particular variation may have handle enclosure 552 formed in a tapered configuration which allows for the assembly 550 to be generally symmetrically-shaped about a longitudinal axis extending from its distal end 554 to its proximal end 556. The symmetric feature of handle assembly 550 may allow for the handle to be easily manipulated by the user regardless of the orientation of the handle enclosure 552 during a tissue manipulation procedure. An additional feature which may further facilitate the ergonomic usability of handle assembly 550 may further include at least one opening 558 defined through the enclosure 552 to allow the user to more easily grip and control the handle 550. Another feature may include grips 560, 562 which may extend from either side of enclosure 552.

As seen in the figure, acquisition member 564 may include additional features to facilitate control of the tissue. For instance, in this variation, in addition to the rotational control 566, an additional rotational control 568 may extend proximally from control 566 and have a diameter smaller than that of control 566 for controlling fine rotational motion of acquisition member 564.

Figure 40B:
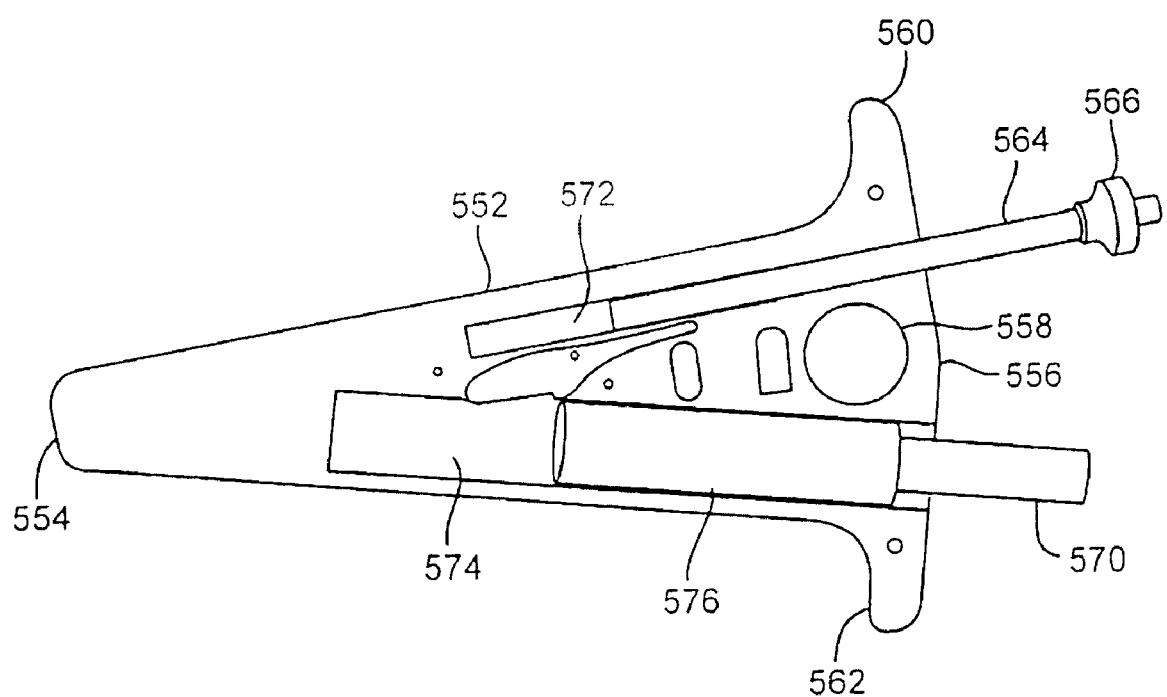

FIG. 40B shows a side view of the handle assembly 550 of FIG. 40A with the enclosure 552 partially removed for clarity. As shown, needle assembly control 570 may be seen inserted within an additional needle deployment mechanism 576, as described below in further detail, within needle assembly receiving channel 574. Acquisition member 564 may also be seen positioned within acquisition member receiving channel 572.

Figure 41A:
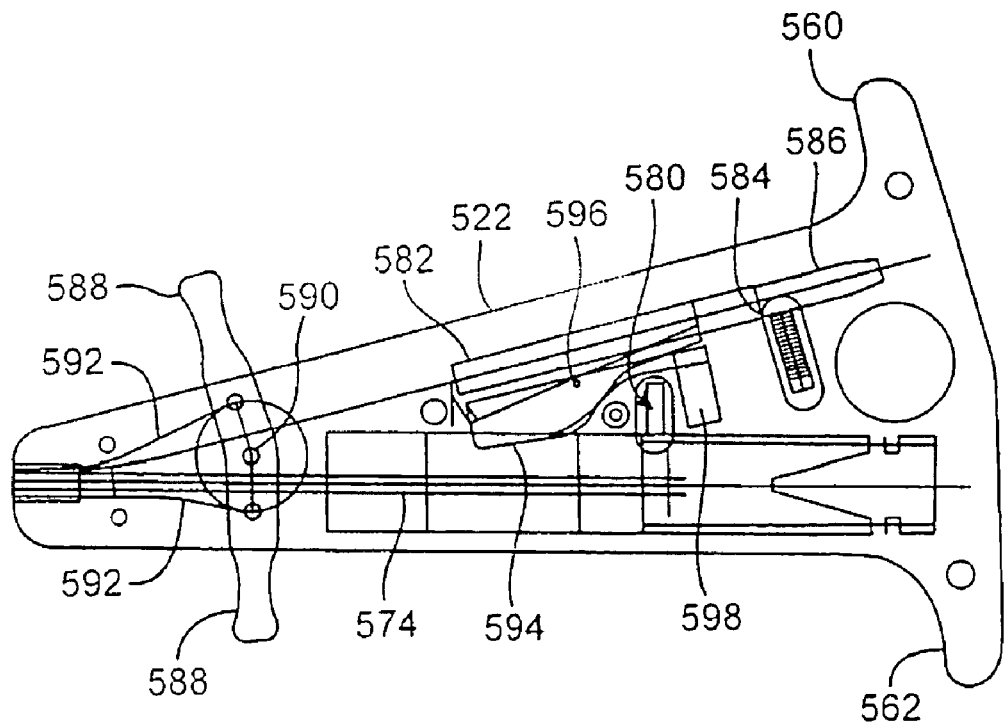
FIGS. 41A and 41B show partial cross-sectional side and detail views, respectively, of another variation of a handle having a pivotable articulation control.

Yet another variation of the handle assembly may be seen in the side view of the handle assembly of FIG. 41A where the handle enclosure 522 is partially removed for clarity. In this variation, needle deployment mechanism lock 580, e.g., a screw or protrusion, may be configured to operably extend at least partially into needle assembly receiving channel 574 to selectively lock the launch tube and/or needle assembly control within receiving channel 574. Also shown is acquisition member receiving channel 582 through which the acquisition member may be translated and/or rotated. Acquisition member lock 584 may also be seen to extend at least partially into the acquisition member receiving channel 582 to selectively lock the acquisition member position, if so desired. The acquisition member receiving channel 582 may be optionally threaded 586 such that the acquisition member may be advanced or withdrawn using a screw-like mechanism.

An additional needle deployment mechanism lock 594 may also be seen pivotally mounted about pivot 596 within enclosure 522. Mechanism 594 may be biased via deployment mechanism biasing element 598, e.g., a spring, to maintain a biasing force against mechanism 594 such that the needle assembly control may automatically become locked during advancement within enclosure 522 to allow for a more controlled anchor deployment and needle assembly advancement.

Figure 41B:
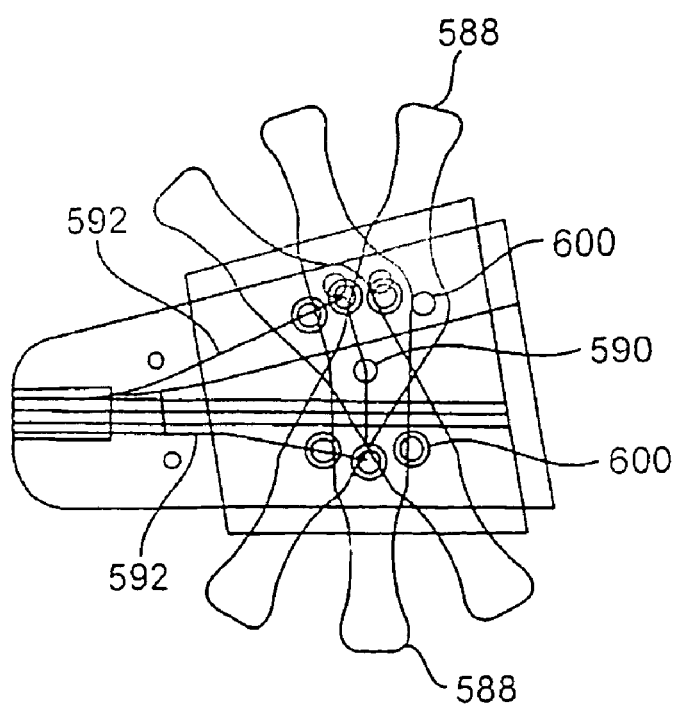

Moreover, one or more pivotable tissue manipulation assembly controls 588 may be mounted to enclosure 522 and extend from one or both sides of enclosure 522 to provide for articulation control of the tissue manipulation assembly, as described above. As presently shown in FIG. 41B in the detail side view from the handle assembly of FIG. 41A, one or more control wires 592 may be connected to control 588 at control wire attachment points 600. Control 588 may pivot about tissue acquisition pivot 590 located within handle enclosure 522. As control 588 is pivoted, the articulation of control wires 592 may articulate a position of the tissue manipulation assembly, as discussed above. FIG. 41B shows an example of the range of motion which may be possible for control 588 as it is rotated about pivot 590.

Figure 42A:
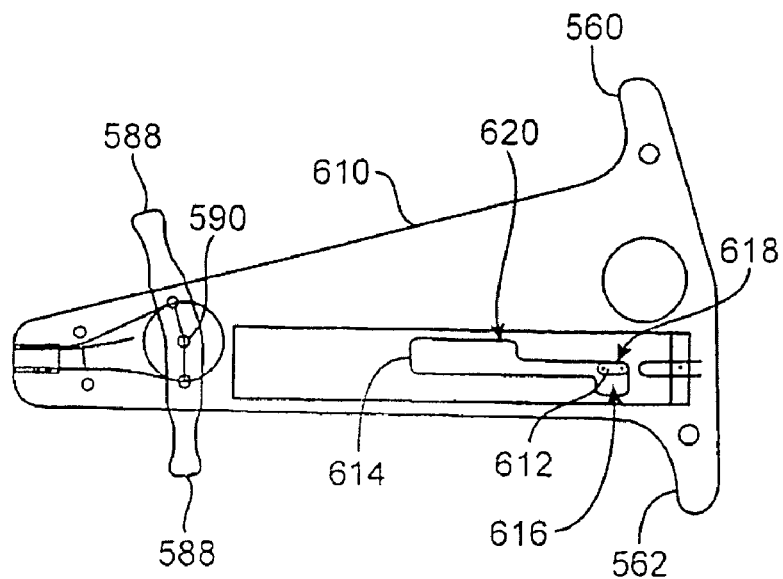
FIG. 42A shows a side view of the handle of FIG. 41A having the multi-position locking and needle assembly advancement system.
Figure 42B:
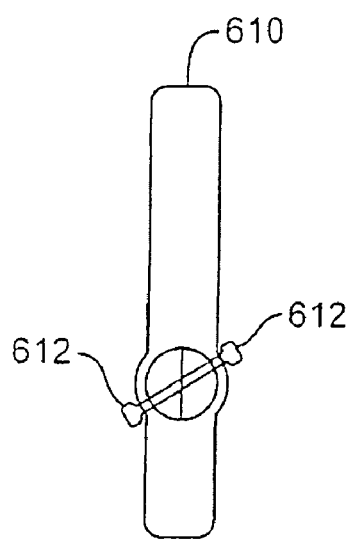
FIGS. 42B to 42D show end views of the handle of FIG. 42A and the various positions of the multi-position locking and needle assembly advancement system.
Figure 42C:
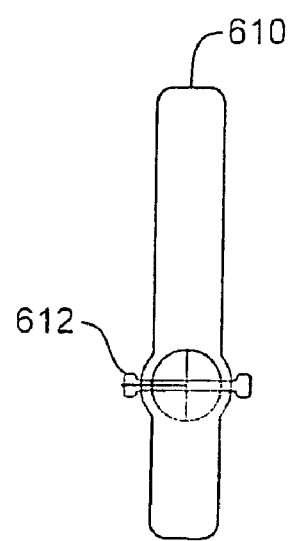

FIG. 42A shows a side view of another variation of handle enclosure 610 which incorporates a needle deployment locking and advancement control 612 which is adapted to be advanced and rotated within needle deployment travel 614 into various positions corresponding to various actions. Locking control 612 may be utilized in this variation to selectively control access of the needle assembly within handle enclosure 610 as well as deployment of the needle assembly and launch tube advancement with a single mechanism. A needle assembly, such as needle assembly 570, may be advanced into handle enclosure 610 with locking control 612 initially moved into needle assembly receiving position 616, shown also in the end view of FIG. 42B. Once the needle assembly has been initially introduced into enclosure 610, the needle assembly may be locked within enclosure 610 by rotating locking control 612 into its needle assembly locking position 618, clockwise rotation as shown in the end view of FIG. 42C. The needle assembly may be locked within enclosure 610 to prevent the accidental withdrawal of the needle assembly from the enclosure 610 or inadvertent advancement of the needle assembly into the tissue.

With locking control 612 in the needle assembly locking position 618, the needle deployment mechanism within enclosure 610 may also be longitudinally translated in a distal direction by urging locking control 612 distally within needle deployment travel 614. Urging locking control 612 distally translates not only the needle deployment mechanism within enclosure 610, but may also translate the launch tube distally such that the launch tube distal portion is pivoted into its deployment configuration, as described above. As the needle deployment mechanism is distally translated within enclosure 610, the needle assembly may also be urged distally with the deployment mechanism such that needle assembly becomes positioned within the launch tube for advancing the needle body into the tissue.

Figure 42D:
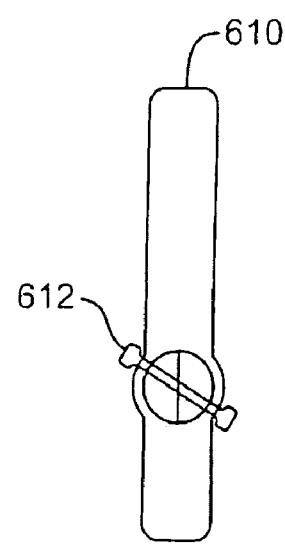

Once locking control 612 has been advanced distally, locking control 612 may again be rotated into the needle assembly release position 620, clockwise rotation as shown in the end view of FIG. 42D. Once in the release position 620, the needle assembly may be free to be translated distally within enclosure 610 for advancing the needle assembly and needle body relative to the launch tube and enclosure 610. To remove the needle assembly from enclosure 610, the steps may be reversed by moving locking control 612 proximally back to its initial needle assembly receiving position 616 so that the needle assembly is unlocked from within enclosure 610. A new needle assembly may then be introduced into enclosure 610 and the process repeated as many times as desired.

Figure 43A:
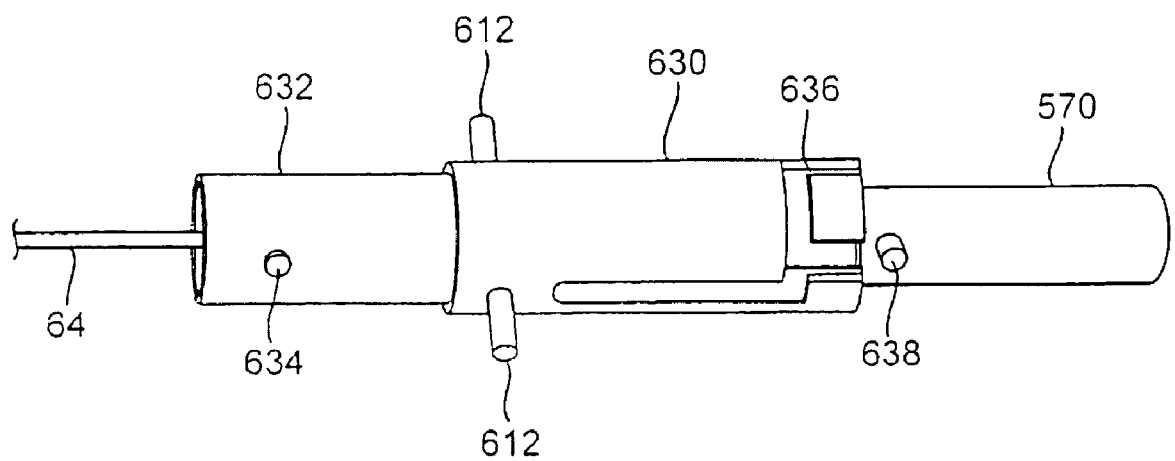
FIG. 43A shows a perspective view of one variation of the multi-position locking and needle assembly advancement system.

Details of one variation of the locking mechanism disposed within the handle enclosure 610 are shown in the perspective view of FIG. 43A. The other elements of the handle assembly have been omitted from this illustration for clarity. The locking mechanism may generally be comprised of outer sleeve 630 disposed about inner sleeve 632. Outer sleeve 630 preferably has a diameter which allows for its unhindered rotational and longitudinal movement relative to inner sleeve 632. Needle deployment locking control 612 may extend radially from outer sleeve 630 and protrude externally from enclosure 610, as described above, for manipulation by the user. Outer sleeve 630 may also define needle assembly travel path 636 along its length. Travel path 636 may define the path through which needle assembly 570 may traverse in order to be deployed. Needle assembly 570 may define one or more guides 638 protruding from the surface of assembly 570 which may be configured to traverse within travel path 636. Inner sleeve 634 may also define guides 634 protruding from the surface of inner sleeve 634 for traversal within grooves defined in handle enclosure 610. Moreover, outer sleeve 630 is preferably disposed rotatably about inner sleeve 632 such that outer sleeve 630 and inner sleeve 632 are configured to selectively interlock with one another in a corresponding manner when locking control 612 is manipulated into specified positions.

Figure 43B:
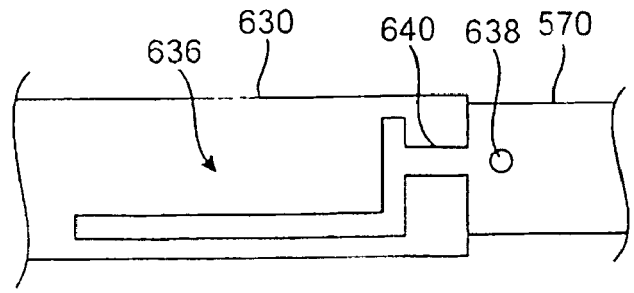
FIGS. 43B to 43E show illustrative side views of the system of FIG. 43A configured in various locking and advancement positions.
Figure 43C:
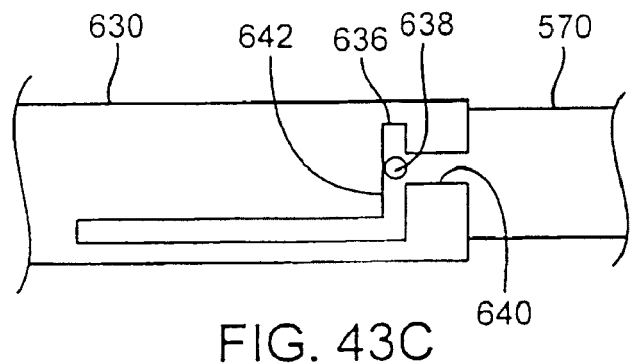
Figure 43D:
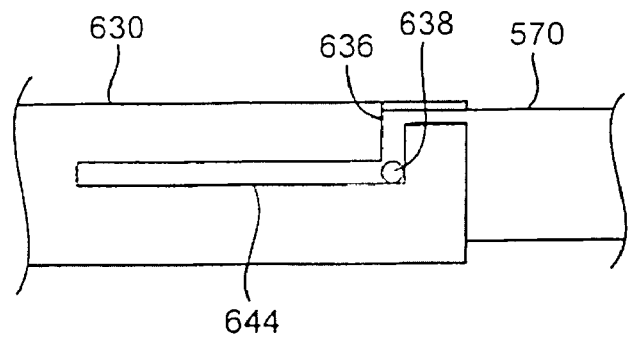
Figure 43E:
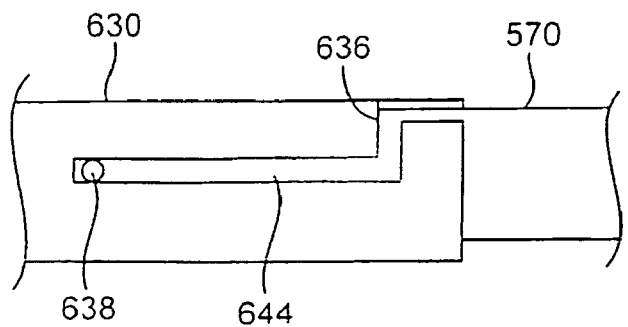

Turning to FIGS. 43B to 43E, the operation of the locking mechanism of FIG. 43A is described in further detail. As needle assembly 570 is initially introduced into handle enclosure 610 and the locking mechanism, needle assembly 570 may be rotated until guides 638 are able to slide into longitudinal receiving channel 640 of travel path 636 defined in outer sleeve 630, as shown in FIGS. 43B and 43C. Locking control 612 may be partially rotated, as described above in FIGS. 42B and 42C, such that outer sleeve is rotated with respect to needle assembly 570 and guides 638 slide through transverse loading channel 642, as shown in FIG. 43D. In this position, the locking mechanism may be advanced distally to deploy the launch tube and to also advance needle assembly 570 distally in preparation for needle assembly 570 deployment. Once the launch tube has been desirably advanced, locking control 612 may again be partially rotated, as shown in FIG. 42D, such that guides 638 on needle assembly 570 are free to then be advanced within longitudinal needle assembly channel 644 relative to the handle enclosure 610 for deploying the needle assembly 570 from the launch tube and into or through the tissue. As mentioned above, the needle assembly 570 may be removed from enclosure 610 and the locking mechanism by reversing the above procedure.

As above, any of the handle assembly variations described herein is not intended to be limited to the examples described but is intended to be utilized in any number of combinations with other aspects of other variations as practicable. Moreover, any of the variations relating to the handle assembly variations may also be used in any number of combinations, as practicable, with variations of other features as described above, if so desired.

Needle Deployment Assembly

Figure 44:
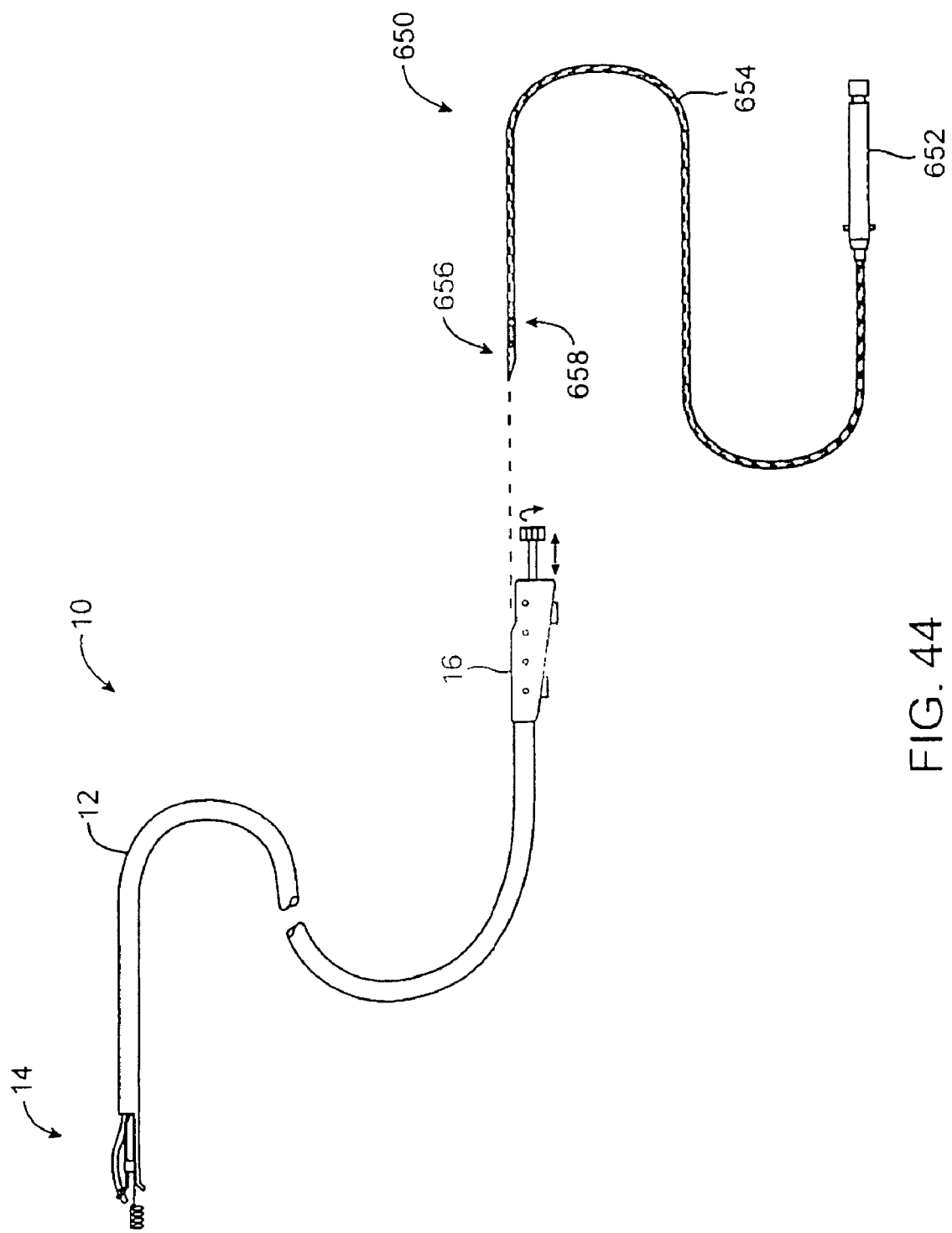
FIG. 44 illustrates a side view of a needle deployment assembly which may be loaded or advanced into an approximation assembly.

As described above, needle deployment assembly 650 may be deployed through approximation assembly 10 by introducing needle deployment assembly 650 into the handle 16 and through tubular body 12, as shown in the assembly view of FIG. 44, such that the needle assembly 656 is advanced from the launch tube and into or through approximated tissue. Once the needle assembly 656 has been advanced through the tissue, the anchor assembly 658 may be deployed or ejected. Anchor assembly 658 is normally positioned within the distal portion of tubular sheath 654 which extends from needle assembly control or housing 652. Once the anchor assembly 658 has been fully deployed from sheath 654, the spent needle deployment assembly 650 may be removed from approximation assembly 10, as described above, and another needle deployment assembly may be introduced without having to remove assembly 10 from the patient. The length of sheath 654 is such that it may be passed entirely through the length of tubular body 12 to enable the deployment of needle assembly 656 into and/or through the tissue.

Figure 45A:
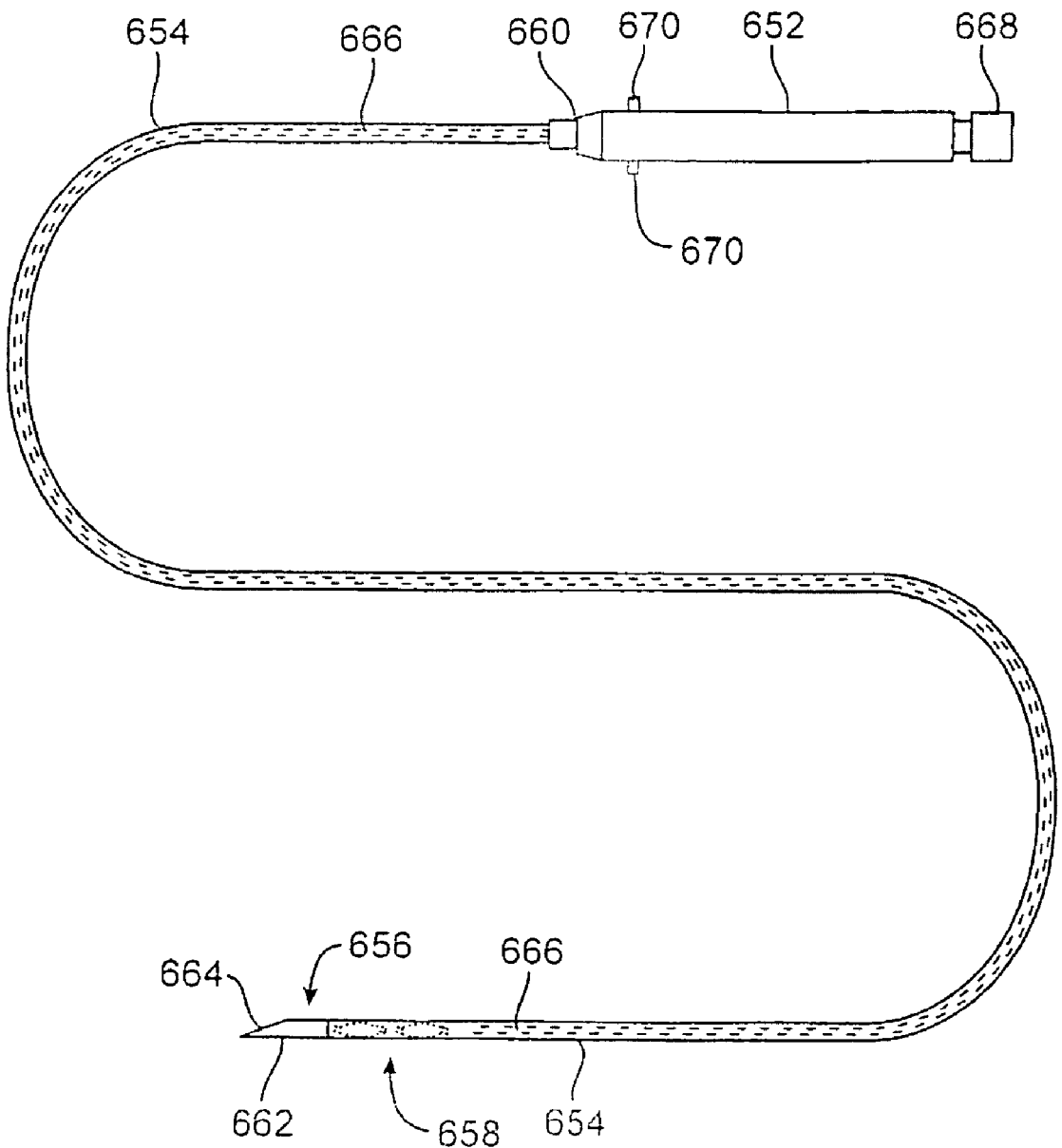
FIG. 45A shows a side view of one variation of a needle deployment assembly.

FIG. 45A shows a detailed assembly view of the needle deployment assembly 650 from FIG. 44. In this variation, elongate and flexible sheath or catheter 654 may extend removably from needle assembly control or housing 652. Sheath or catheter 654 and housing 652 may be interconnected via interlock 660 which may be adapted to allow for the securement as well as the rapid release of sheath 654 from housing 652 through any number of fastening methods, e.g., threaded connection, press-fit, releasable pin, etc. Needle body 662, which may be configured into any one of the variations described above, may extend from the distal end of sheath 654 while maintaining communication between the lumen of sheath 654 and needle opening 664.

Figure 45B:
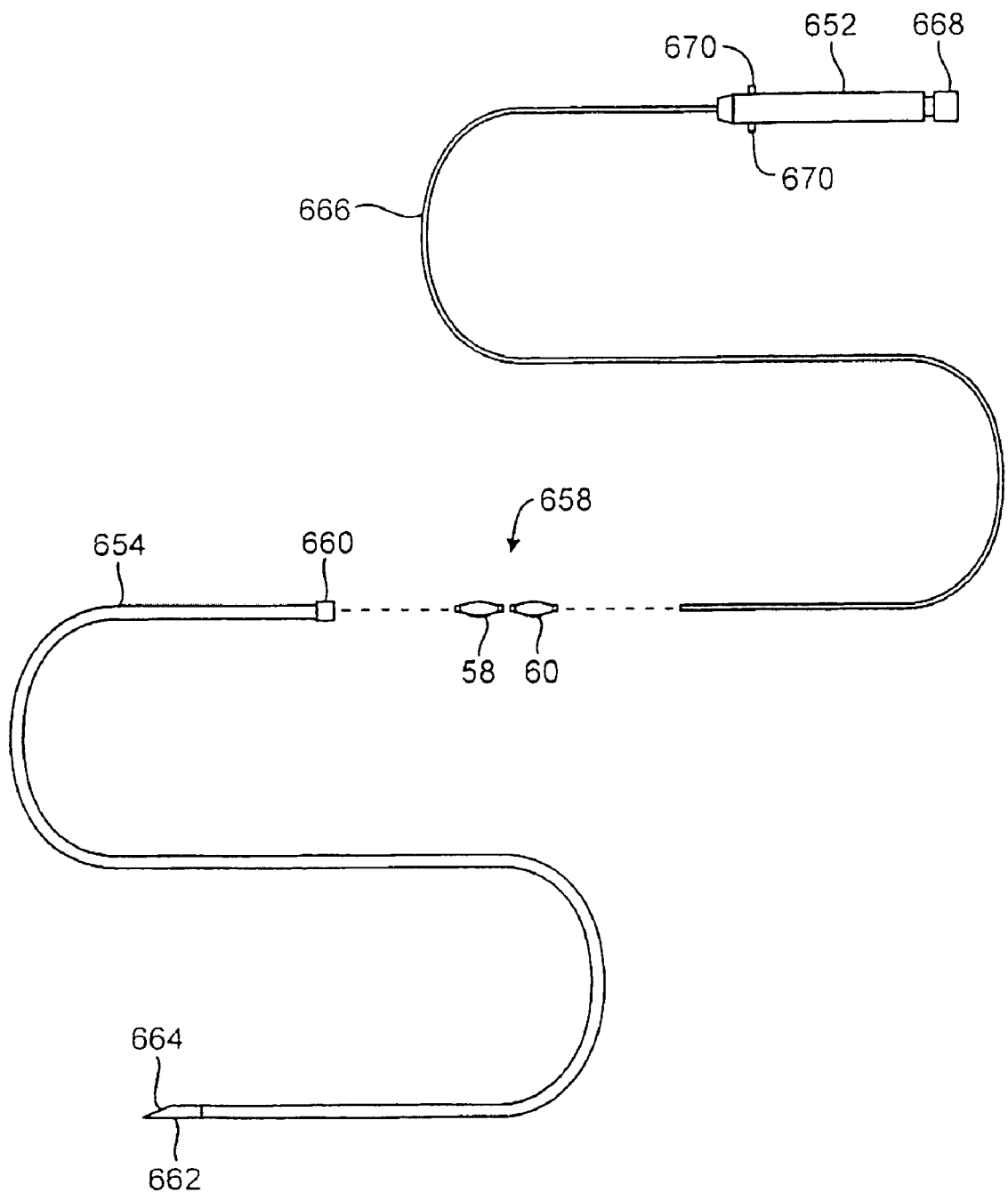
FIG. 45B shows an exploded assembly of FIG. 45A in which the tubular sheath is removed to reveal the anchor assembly and elongate pusher element.

Elongate pusher 666 may comprise a flexible wire or hypotube which is translationally disposed within sheath 654 and movably connected within housing 652. A proximally-located actuation member 668 may be rotatably or otherwise connected to housing 652 to selectively actuate the translational movement of elongate pusher 666 relative to sheath 654 for deploying the anchors from needle opening 664. Anchor assembly 658 may be seen positioned distally of elongate pusher 666 within sheath 654 for deployment from sheath 654. Needle assembly guides 670 may also be seen protruding from housing 652 for guidance through the locking mechanism described above. FIG. 45B shows an exploded assembly view of the needle deployment assembly 650 from FIG. 45A. As seen, sheath 654 may be disconnected from housing 652 via interlock 660 to reveal the elongate pusher 666 connected to housing 652 and the distal and proximal anchors 58, 60, respectively, of anchor assembly 658.

Figure 46A:
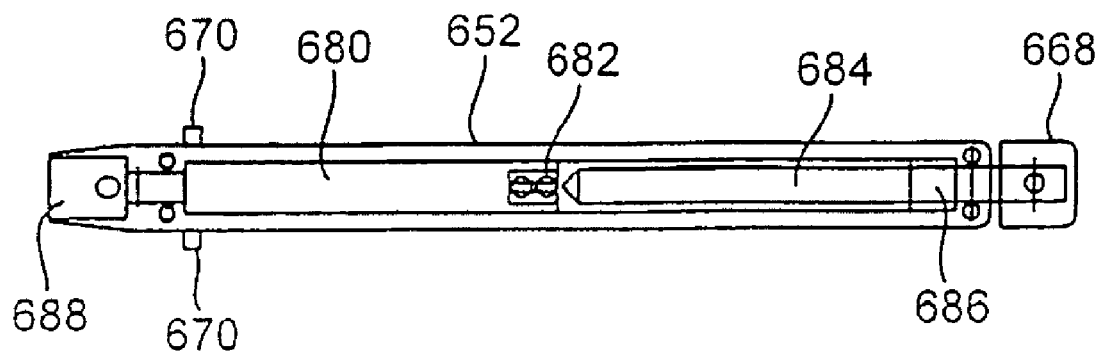
FIGS. 46A and 46B show partial cross-sectional side views of a shuttle element advanced within the needle assembly housing.
Figure 46B:
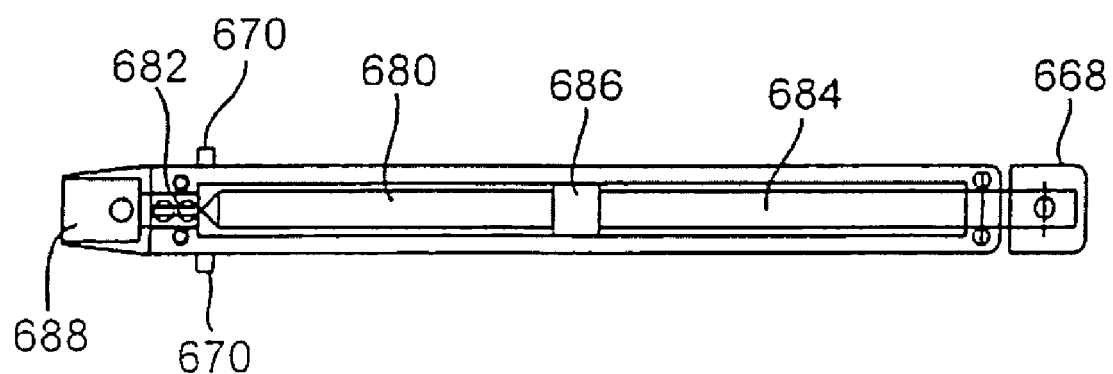

FIGS. 46A and 46B show partial cross-sectional views of one variation of housing 652. As shown in FIG. 46A, elongate pusher 666 may be attached to shuttle 682, which in turn may be connected to threaded interface element 686. As actuation member 668 is manipulated, e.g., by rotating it clockwise, lead screw 684 may be rotated about its longitudinal axis to advance threaded interface element 686 over lead screw 684 distally through shuttle channel 680, as shown in FIG. 46B, where shuttle 682 has been advanced entirely through shuttle channel 680. Tubular sheath interlock 688 may be seen at the distal portion of housing 652 through which the elongate pusher 666 may be advanced. To reverse the direction of elongate pusher 666 and shuttle 682, actuation member 668 may be reversed in the opposite direction.

Figure 47A:
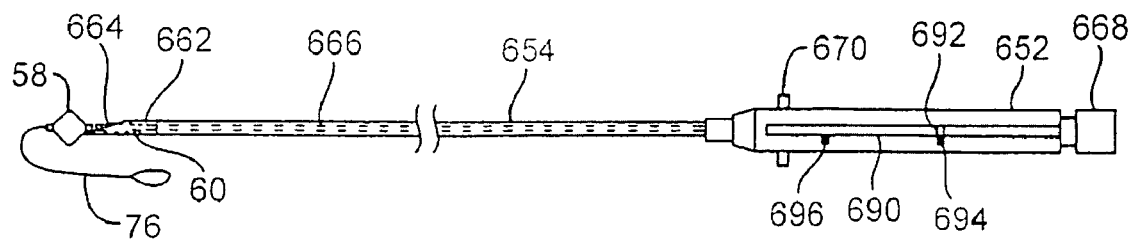
FIGS. 47A and 47B illustrate one variation of deploying the anchors using the needle assembly.
Figure 47B:
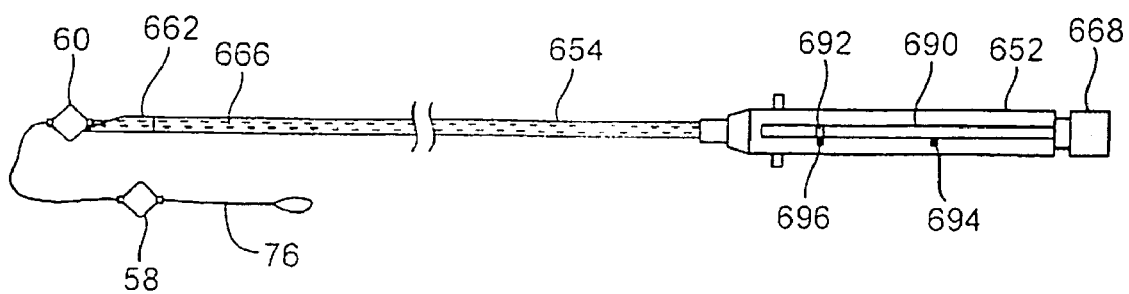

Another variation of the needle deployment assembly may be seen in FIGS. 47A and 47B which show assembly side views. In this variation, housing 652 may define an indicator window 690 along the length of housing 652 to enable viewing of a visual indicator 692 which may be utilized to indicate the position of the elongate pusher 666 within the sheath 654. In the illustration of FIG. 47A, as actuation member 668 is manipulated to advance pusher 666 distally, indicator 692 may move correspondingly within window 690. Positional indicators may also be marked along window 690 to indicate to the user when specified limits have been reached. For instance, positional indicator 694 may be marked such that alignment of indicator 692 with positional indicator 694 is indicative to the user that distal anchor 58 has been deployed from sheath 654.

Likewise, an additional positional indicator 696 may be marked such that alignment of indicator 692 with positional indicator 694 is indicative to the user that the proximal anchor 60 has also been deployed from sheath 654, as shown in FIG. 47B. Any number of positional indicators or methods for visually marking may be utilized as the above examples are merely intended to be illustrative and not limiting. Moreover, to further facilitate the visualization of anchor positioning within sheath 654, the sheath itself may be fabricated from a transparent material, such as plastics, so that the user may visually locate a position of one or both anchors during anchor deployment into or through the tissue.

Figure 47C:
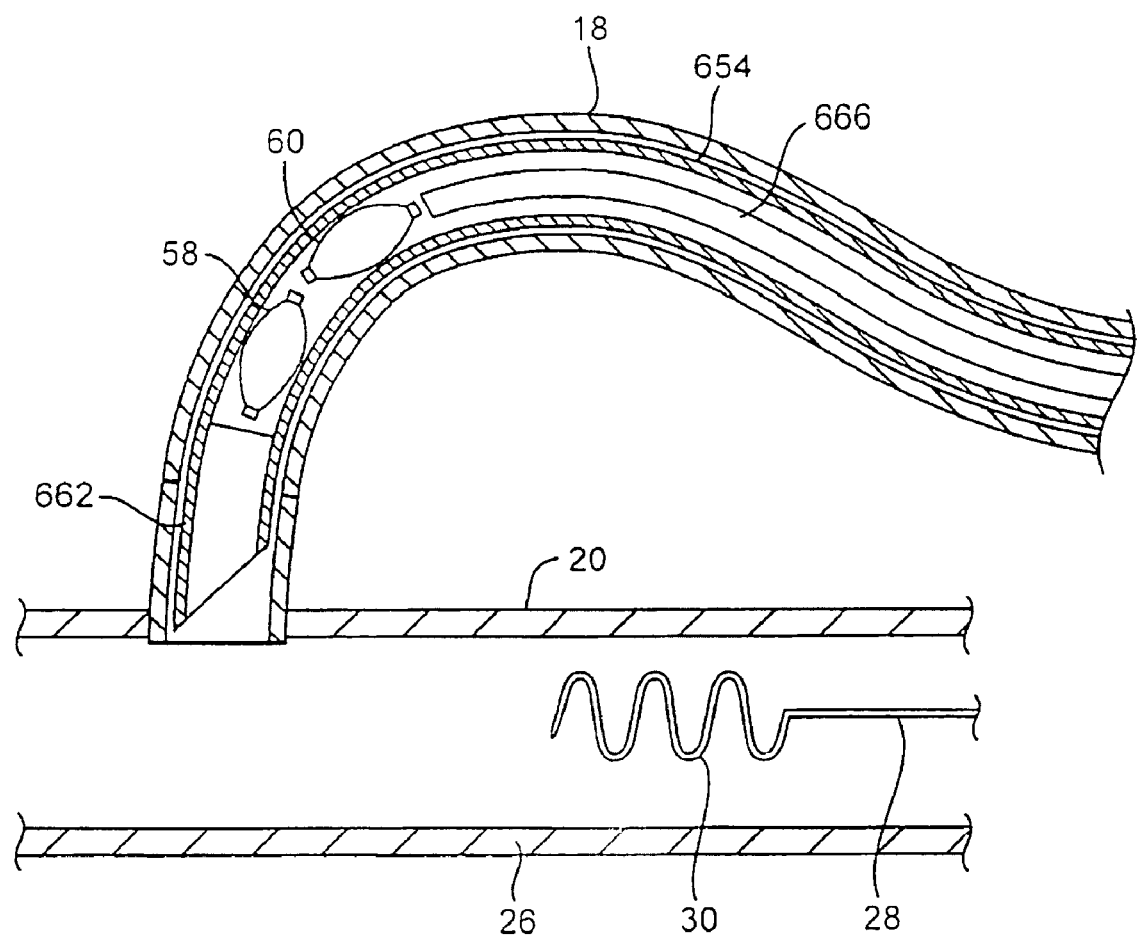
FIG. 47C illustrates a partial cross-sectional view of one variation of the needle and anchor assemblies positioned within the launch tube.

FIG. 47C shows an illustrative cross-sectional view of the launch tube 18 in its deployment configuration. Tubular sheath 654 and needle body 662 may be seen positioned within the distal portion of launch tube 18 ready for deployment into any tissue (not shown for clarity) which may be positioned between upper and lower extension members 20, 26. Also shown are distal and proximal anchors 58, 60, respectively (suture is not shown for clarity), positioned within sheath 654 distally of elongate pusher 666.

Figure 48:
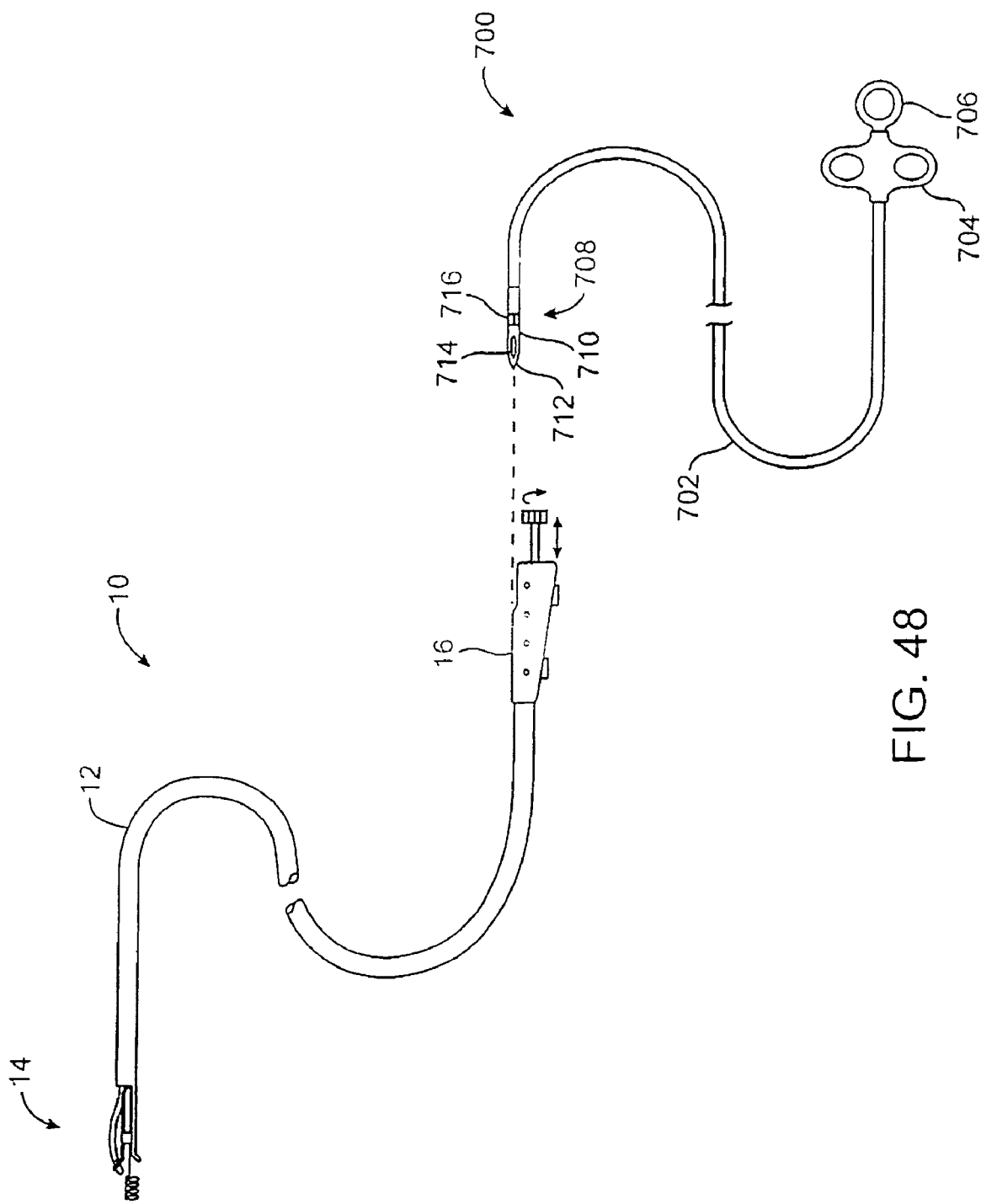
FIG. 48 shows a side view of another variation in which a manipulatable grasping needle assembly may be loaded into the approximation assembly.

FIG. 48 shows an assembly view of yet another variation in which manipulatable needle assembly 700 may be utilized with approximation assembly 10. Similar to the assembly above, manipulatable needle assembly 700 may be deployed through approximation assembly 10 by introducing needle assembly 700 into the handle 16 and through tubular body 12. Once the needle assembly has been advanced through the tissue, an anchor assembly may be deployed or ejected and/or the tissue or suture may be manipulated via the assembly 700. A further detailed description of manipulatable needle assembly 700 is disclosed in co-pending U.S. patent application Ser. No. 10/898,684, filed Jul. 23, 2004 and entitled "Manipulatable Grasping Needle", which is incorporated herein by reference in its entirety.

As shown in FIG. 48, an elongate flexible member 702 may be tubular such that at least one lumen is defined through the length of flexible member 702. Handle 704 may be positioned at a proximal end of flexible member 702 and control handle 706 may be likewise positioned. Control handle 706 may be configured to enable the articulation of piercing and grasping assembly 708 into an open or closed configuration, as described in further detail below. Control handle 708, as well as handle 704, which is positioned at a distal end of flexible member 702, may be operably connected to piercing and grasping assembly 708, e.g., via control wires, which may run through the length of flexible member 702.

Flexible member 702 may be made from a variety of flexible materials such as polymers. If made from a polymeric material, flexible member 702 may be reinforced along its length as necessary using various methods such as interspersing metallic braids, weaves, reinforcing wires, etc., throughout the length of the flexible member 702. Alternatively, metallic materials, e.g., stainless steel, platinum, etc., and particularly superelastic metals and alloys, e.g., Nitinol, etc., may be utilized in constructing flexible member 702 provided that the material is sufficiently adapted to flex when manipulated. In the case of stainless steel or like metals, the length of flexible member 702 may be scored or perforated to allow for additional flexibility. Moreover, the diameter of flexible member 702 may be varied to suit the application in which assembly 700 may be employed. For example, if assembly 700 were advanced, e.g., through a conventional endoscope for use in a patient's stomach, flexible member may range anywhere in diameter from 2-3 mm and may have a length greater than or less than 100 cm. These dimensions are merely intended to be illustrative and are not intended to limit the size or scope of the assembly 700.

Figure 49A:
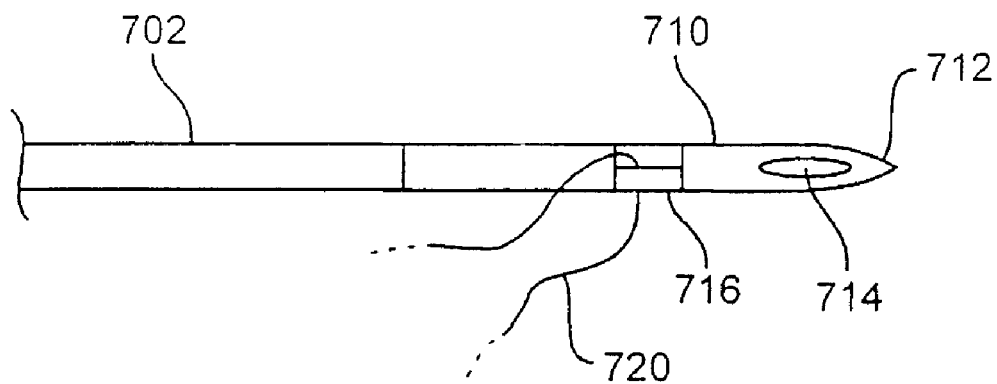
FIGS. 49A and 49B show detail side views of a variation of the manipulatable grasping needle of FIG. 48.

As generally shown, piercing and grasping assembly 708 may be comprised of needle body 710, which has a tapered or sharpened tip 712 for piercing into or through tissue. Needle body 710 may also define an opening or lumen 714 therethrough for retaining and passing a tissue anchor, as described further below. As seen in the detail side view of FIG. 49A, piercing and grasping assembly 708 may be configured into a low-profile closed configuration for advancement into the body and for piercing into or through tissue. As piercing and grasping assembly 708 is advanced into or through tissue, a length of suture 720 may be releasably retained by assembly 708 between needle body 710 and grasping arm 716, which may be positioned proximally of tip 712 and/or needle body 710.

Figure 49B:
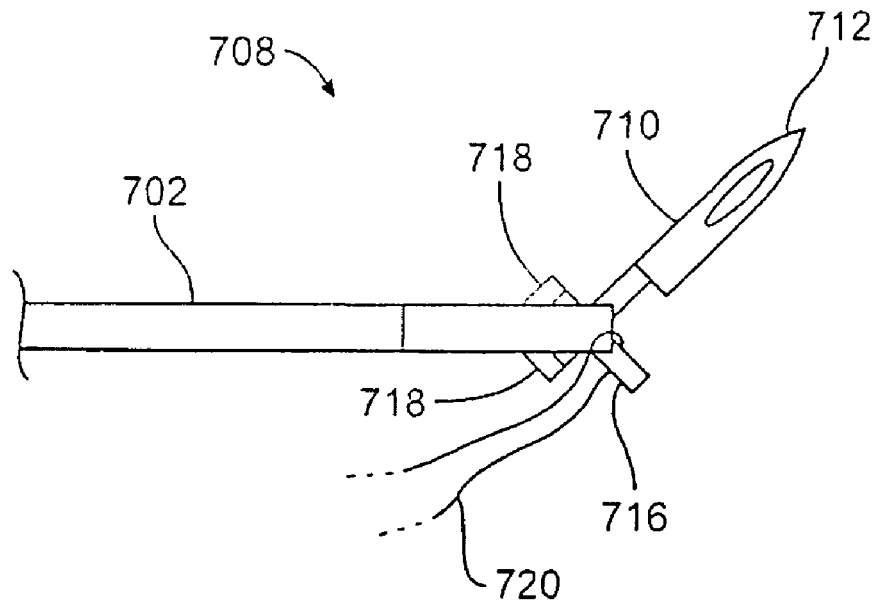

Once piercing and grasping assembly 708 has been desirably advanced into or through tissue, assembly 708 may be actuated into an open configuration where grasping arm 716 may project from needle body 710, as shown in FIG. 49B. In the open configuration, grasping arm 716 may be open relative to needle body 710 such that suture 720 may be released from piercing and grasping assembly 708. Alternatively, piercing and grasping assembly 708 may be manipulated to grasp a free length of suture. Linkage assembly 718, which may be actuated via a push and/or pull wire (not shown) contained within tubular member 702, may be used to open and close needle body 710 and grasping arm 716. As shown, both needle body 710 and grasping arm 716 may each be actuated into an opened configuration relative to tubular member 702; alternatively, linkage assembly 718 may be utilized to actuate a single member, i.e., needle body 710 or grasping arm 716, into an opened configuration for suture manipulation or release.

Elongate tubular member 702 may be flexible or it may also be constructed as a rigid shaft. In either case, one or several portions of elongate member 702 may comprise an articulatable section 30 along a length of elongate member 702. A section of member 702 just proximal of piercing and grasping assembly 708 may be configured to be articulatable such that assembly 708 may be articulated via handle 704. One or several control wires may be routed through elongate member 702 in any number of ways to enable articulatable section 30 to conform to a desired shape. An elongate member 702 having one or several articulatable sections 30 may enable assembly 708 to be manipulated about or around tissue such that suture manipulation is facilitated.

Figure 50A:
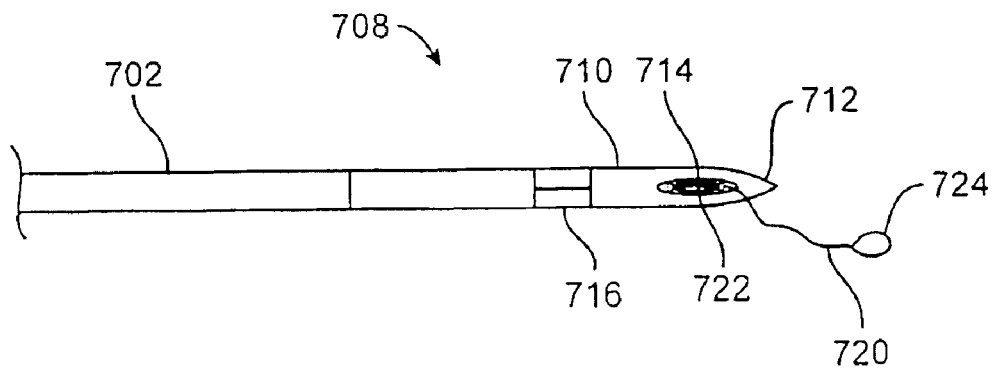
FIGS. 50A and 50B show detail side views of another variation of the manipulatable grasping needle which may be utilized to deploy anchors.
Figure 50B:
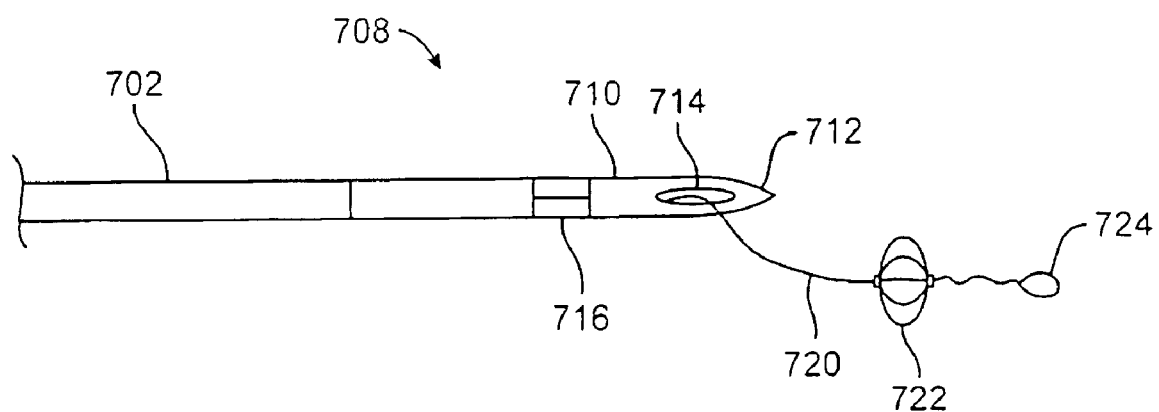

The piercing and grasping assembly 708 may be utilized in a variety of different procedures. In one instance, assembly 708 may be advanced into a hollow body organ, e.g., a stomach, and used to pierce through created tissue plications and deposit soft tissue anchors for securing the tissue plications. Examples of methods and devices for creating tissue plications may be seen in further detail in U.S. patent application Ser. No. 10/735,030 which has been incorporated by reference, above. As shown in FIG. 50A, an expandable tissue anchor 722 may be seen positioned within opening 714 of needle body 710 for delivery. Suture 720 ending in terminal loop 724 may be seen passing through and from tissue anchor 722. Once assembly 708 has been desirably passed through tissue and appropriately positioned, tissue anchor 722 may be ejected from needle body 710, e.g., using a pusher mechanism. Once free from the constraints of needle body 710, tissue anchor 722 may be free to expand for anchoring against a tissue surface, as seen in FIG. 50B. Further details relating to tissue anchors and mechanisms which may be utilized for ejecting and positioning such anchors are disclosed in further detail in U.S. patent application Ser. No. 10/840,950 filed May 7, 2004, which has been incorporated herein by reference above in its entirety.

As above, any of the needle assembly variations described herein is not intended to be limited to the examples described but is intended to be utilized in any number of combinations with other aspects of other variations as practicable. Moreover, any of the variations relating to the needle assembly variations may also be used in any number of combinations, as practicable, with variations of other features as described above, if so desired.

Anchor Deployment

In deploying the anchors into or through the tissue, one or more anchors may be positioned within the launch tube for deployment. As described above, deployment of the anchors may be accomplished in one method by pushing the anchors via the elongate pusher element until the anchor is ejected from the needle body opening. Once the anchor is free from the constraints of the needle catheter, it may reconfigure into an expanded configuration for placement against the tissue surface.

To ensure that the anchor is not prematurely ejected from the needle assembly, various interlocking features or spacing elements may be employed. As shown in the partial cross-sectional view of FIG. 51A, the collar of proximal anchor 60 and the distal end of elongate pusher may be interlocked with one another via a temporary interlocking feature 730. Likewise, the adjacent collars of distal and proximal anchors 58, 60, respectively, may be optionally interlocked with one another via a temporary interlocking feature 732 as well. Such an interlocking feature may enable the anchor assembly to be advanced distally as well as withdrawn proximally through sheath 654 and needle body 662 in a controlled manner without the risk of inadvertently pushing one or more anchors out of needle body 662.

Figure 51A:
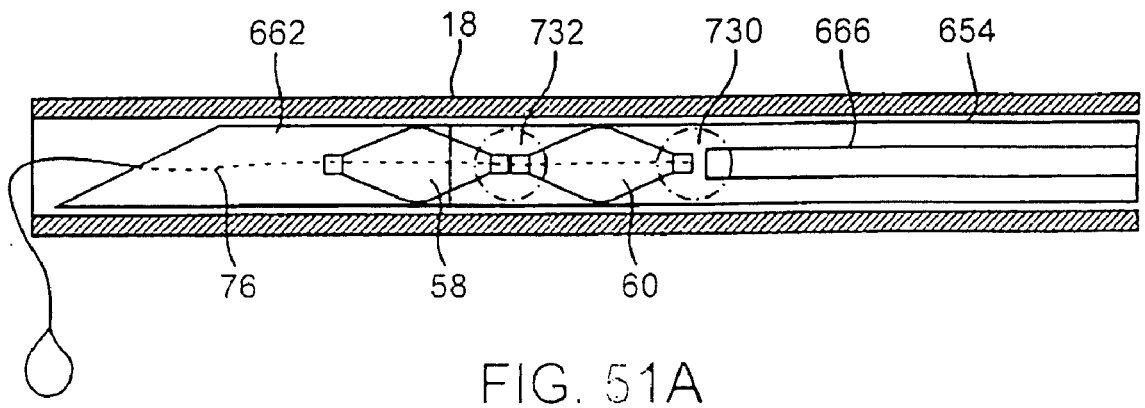
FIGS. 51A and 51B show partial cross-sectional views of various methods for aligning a suture through the anchor assembly within the needle assembly.
Figure 51B:
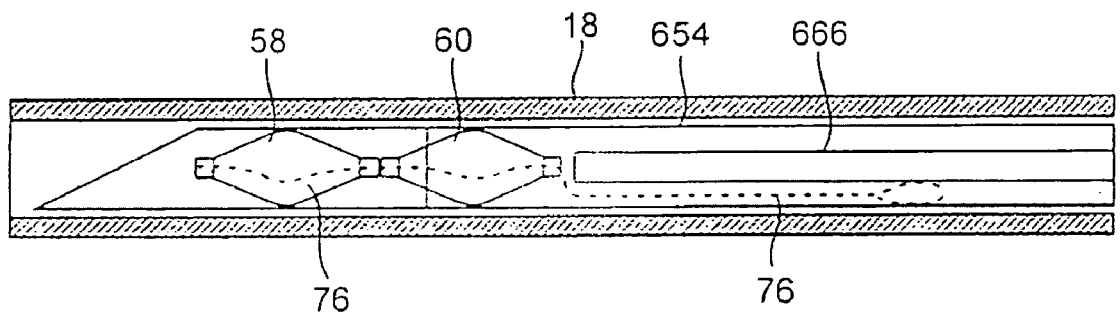
Figure 51C:
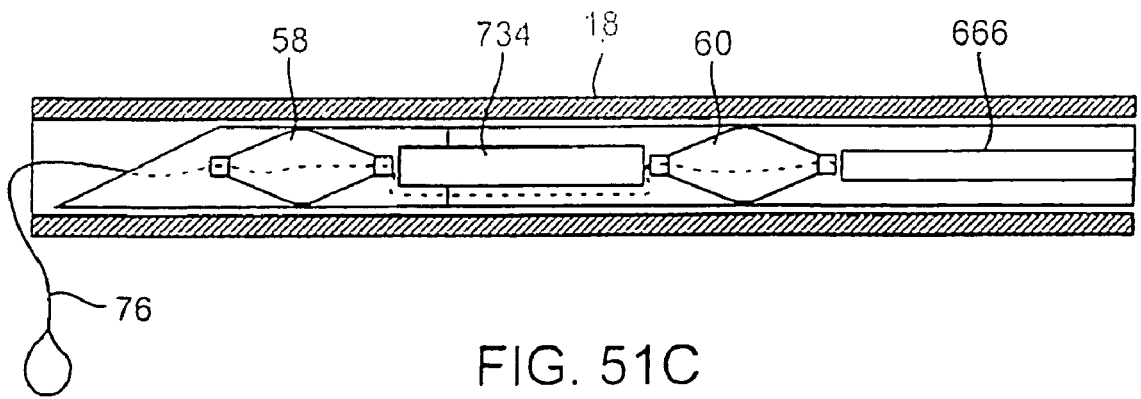
FIG. 51C shows a partial cross-sectional view of an anchor assembly variation utilizing a spacer between adjacent anchors within the needle assembly.

Aside from the use of interlocking features, one or more spacing elements 734 may also be placed between adjacent anchors within sheath 654 in another variation as shown in FIG. 51C. In use, as distal anchor 58 is initially deployed, spacer 734 may provide additional distance between the adjacent anchors so that proximal anchor 60 is not inadvertently deployed along with distal anchor 58. Spacer element 734 may optionally include interlocking features to temporarily interlock with the adjacent anchors. Moreover, when proximal anchor 60 is deployed, spacer element 734 may be ejected into the patient's body, e.g., the stomach, to simply degrade or pass naturally from the patient. Accordingly, such a spacer 734 is preferably made from any number of biocompatible and/or biodegradable materials.

Aside from the interlocking anchor features, the suture 76 which may be routed through anchors 58, 60 to interconnect them may also be varied in placement with respect to the anchors. As shown in FIG. 51A, suture 76 may be optionally routed such that its terminal end is deployed initially with distal anchor 58. Alternatively, suture 76 may be routed such that its terminal end is deployed lastly along with proximal anchor 60. Other variations for routing the suture 76 may be employed as practicable as the foregoing examples are described merely as examples and are not intended to be limiting in their description.

Figure 52A:
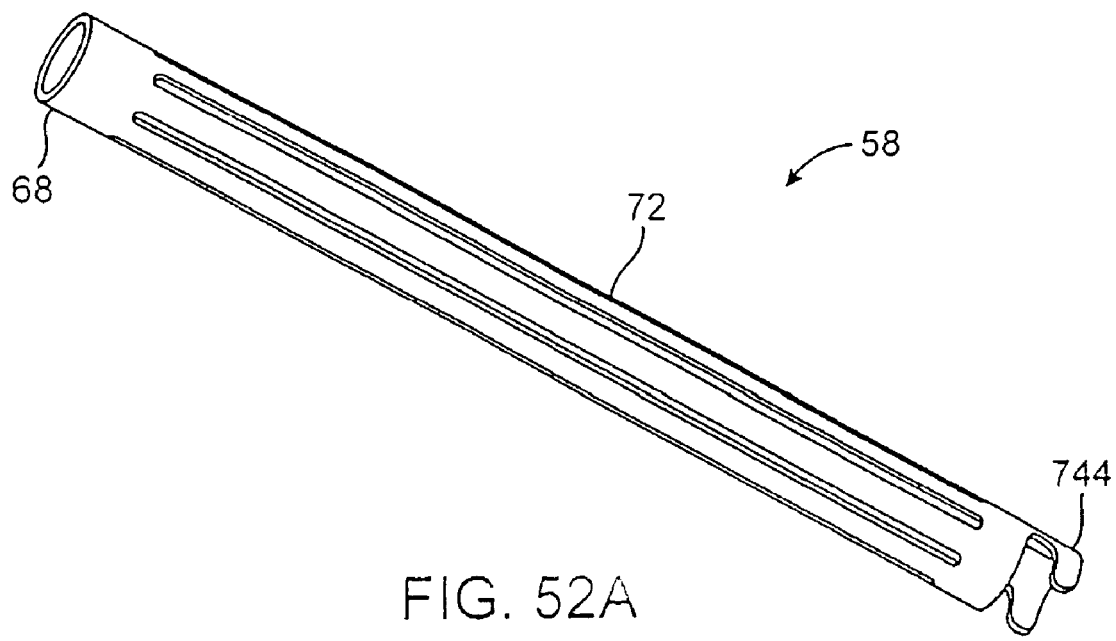
FIGS. 52A and 52B show perspective detail views of unexpanded anchors having interlocking features on one or more of the collars for temporarily interlocking the anchors and/or elongate pusher to one another.
Figure 52B:
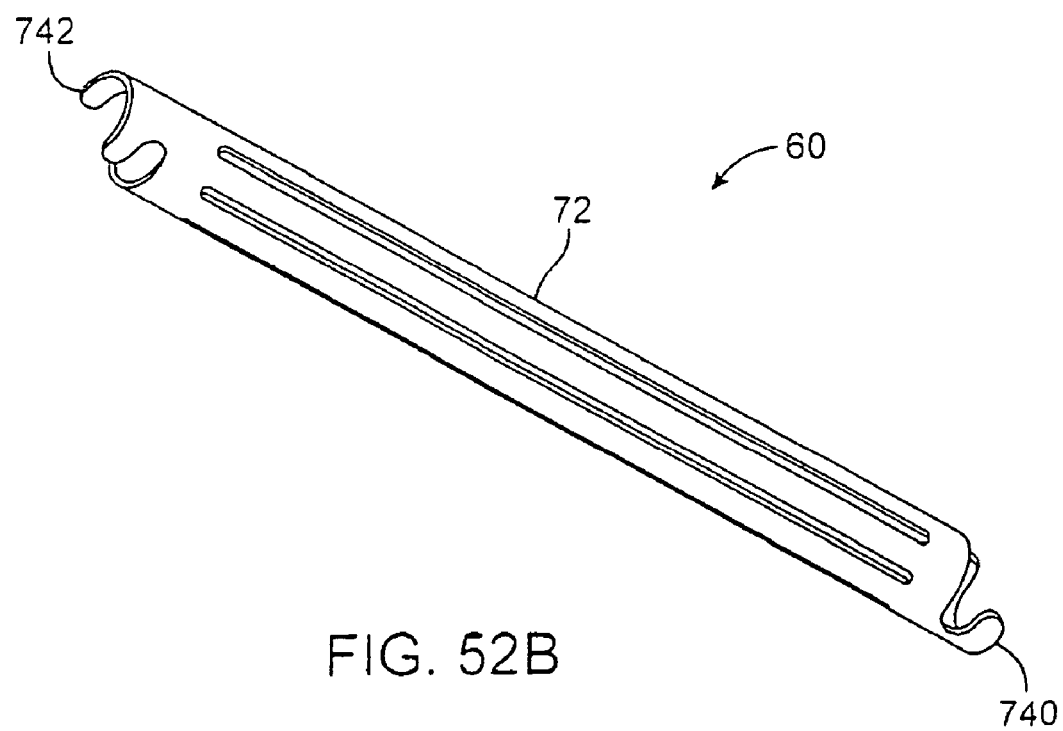
Figure 52C:
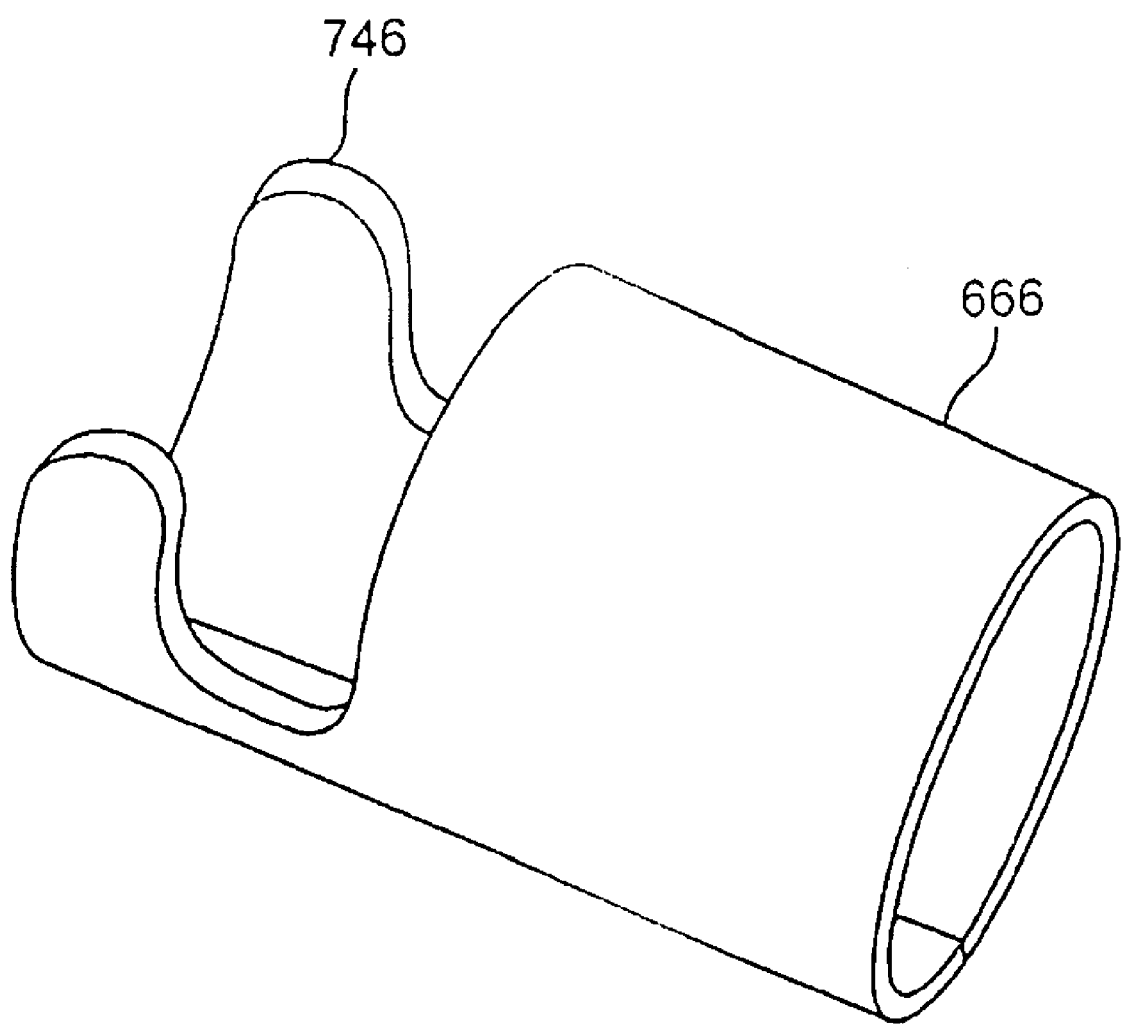
FIG. 52C shows a detail perspective view of a curved interlocking feature which may be integrated on the distal end of the elongate pusher.

Turning back to the anchor interlocking features, FIGS. 52A and 52B show perspective views of distal anchor 58 and proximal anchor 60, respectively, having one variation for temporarily interlocking the anchors. The anchors 58, 60 are shown in their unexpanded delivery configuration when positioned within the tubular delivery sheath or catheter 654. As shown, the proximal collar of distal anchor 58 may have a circumferential-tab locking feature 744, as shown in FIG. 52A, which is configured to inter-fit in a complementary manner with circumferential-tab locking feature 742 on proximal anchor 60, as shown in FIG. 52B. Likewise, the proximal collar of proximal anchor 60 may also have a circumferential-tab locking feature 740 which is configured to inter-fit also in a complementary manner with the locking feature 746 located on the distal end of elongate pusher 666, as shown in the detail perspective view of FIG. 52C.

Figure 53A:
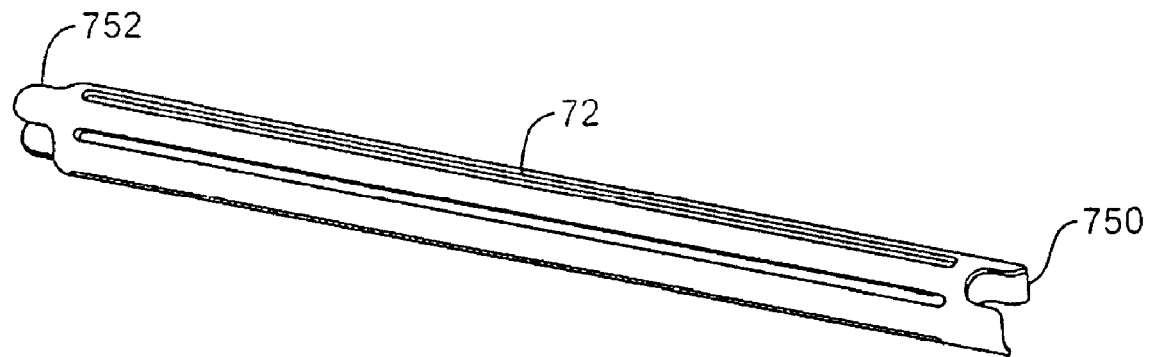
FIGS. 53A and 53B show another variation of an interlocking feature which may be integrated into one or more anchors.
Figure 53B:
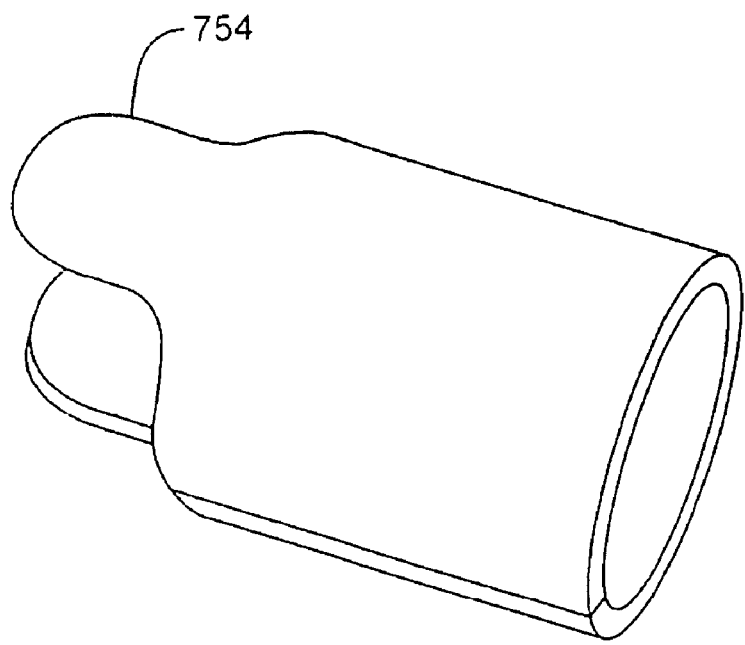

FIGS. 53A and 53B show another variation on the interlocking feature where the anchor may have a longitudinal-tab locking feature 750 or a receiving-tab locking feature 752 which is configured to inter-fit with one another in a complementary manner. FIG. 53B shows the distal end of an elongate pusher variation having a longitudinal-tab locking feature 754 for inter-fitting with the proximal collar of an adjacent anchor.

With any of the interlocking features described herein, they are preferably configured to temporarily lock adjacent anchors and/or the anchor to the elongate pusher to one another. The positioning and orientation of the adjacent anchors and elongate pusher may be such that the abutting ends of each are configured to remain interlocked with one another when constrained by the inner surface of the sheath 654. However, when an anchor is ejected from the constraints of the sheath 654 and the alignment of the anchors is skewed, the interlocking feature is preferably adapted to thus unlock itself and thereby release the ejected anchor.

Figure 54A:
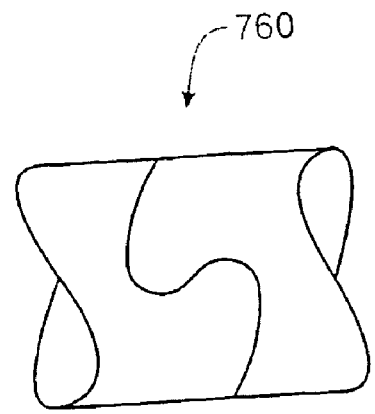
FIGS. 54A to 54C show a curved-tab locking feature variation which may be utilized in deploying one or more anchors.
Figure 54B:
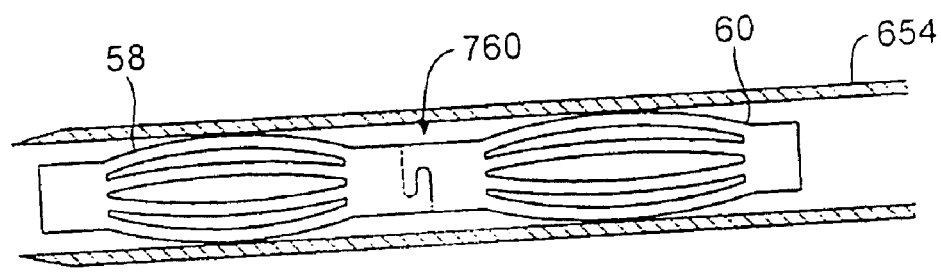
Figure 54C:
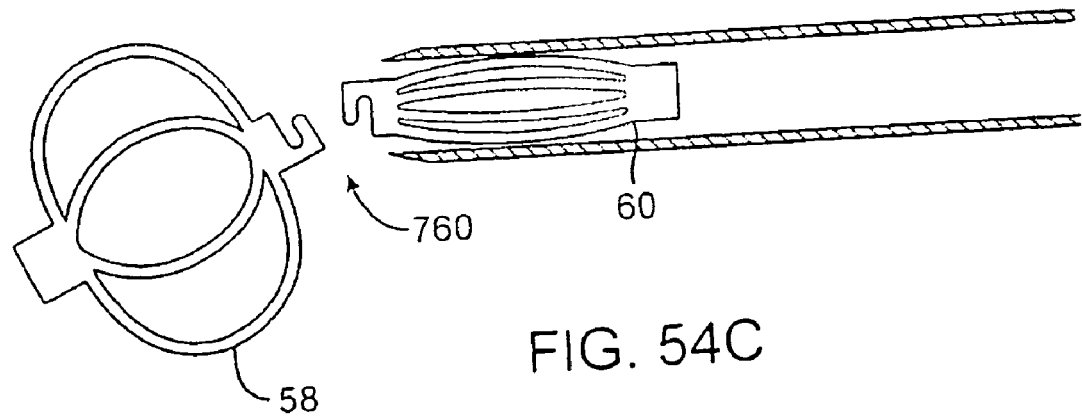

FIG. 54A shows another variation on a curved-tab interlocking feature 760. FIG. 54B shows distal and proximal anchors 58, 60, respectively, interlocked via the curved-tab feature 760 when constrained in the sheath 654. FIG. 54C shows distal anchor 58 having been ejected and released from the interlocking feature 760. The interlocking feature is not shown on the proximal end of proximal anchor 60 and other features such as the elongate pusher and suture have been omitted merely for the sake of clarity.

Figure 55A:
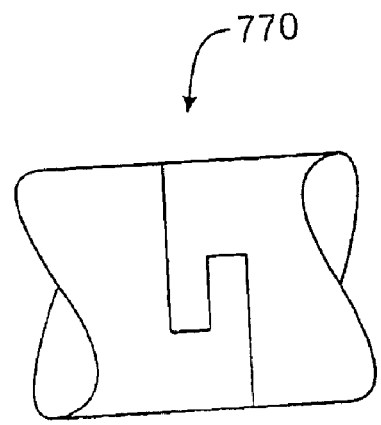
FIGS. 55A to 55C show an interlocking feature variation which may be utilized in deploying one or more anchors.
Figure 55B:
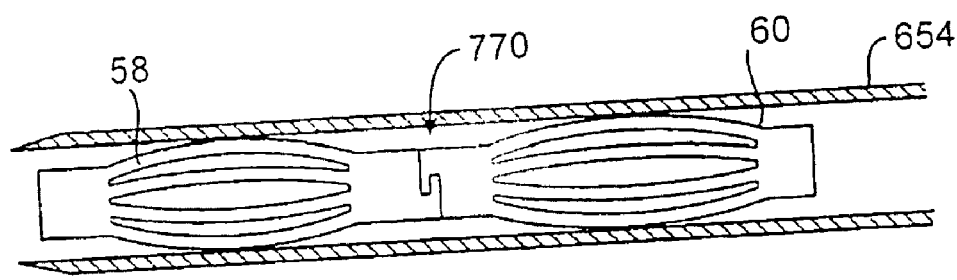
Figure 55C:
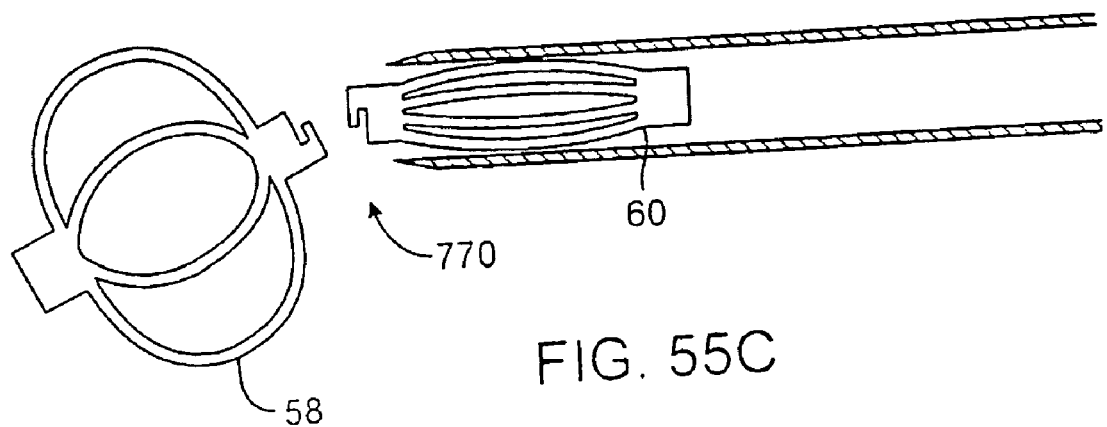

FIGS. 55A, 55B, and 55C likewise show angled interlocking feature 770 in a detail view, between adjacent anchors, and with distal anchor 58 being released from the interlocking feature 770, respectively.

Figure 56A:
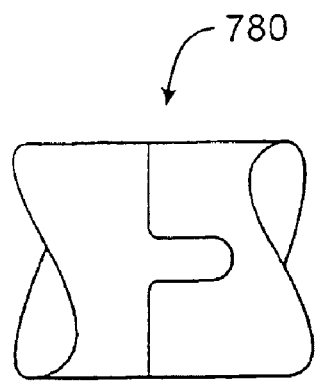
FIGS. 56A to 56C show a tabbed locking feature variation which may be utilized in deploying one or more anchors.
Figure 56B:
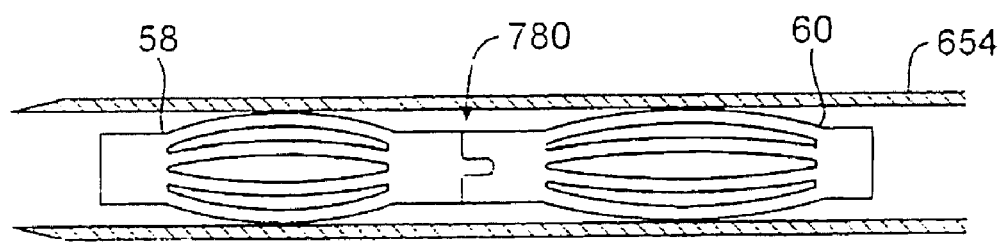
Figure 56C:
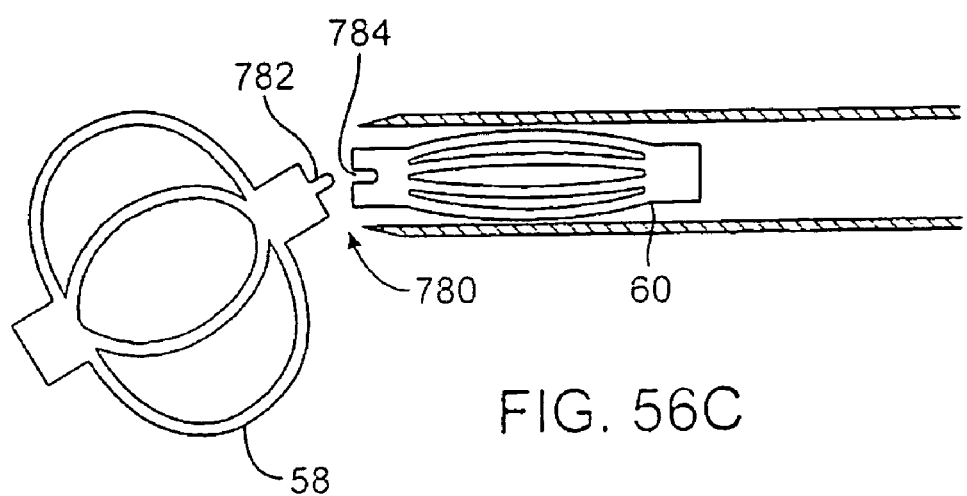
Figure 57A:
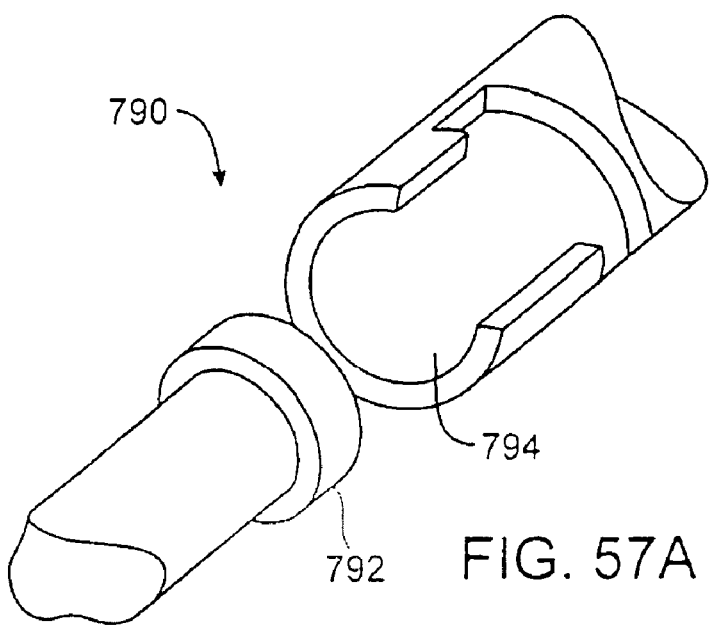
FIGS. 57A to 57C show a pin and groove locking feature variation which may be utilized in deploying one or more anchors.
Figure 57B:
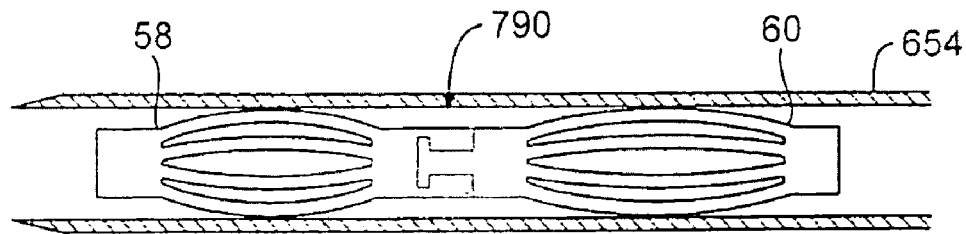
Figure 57C:
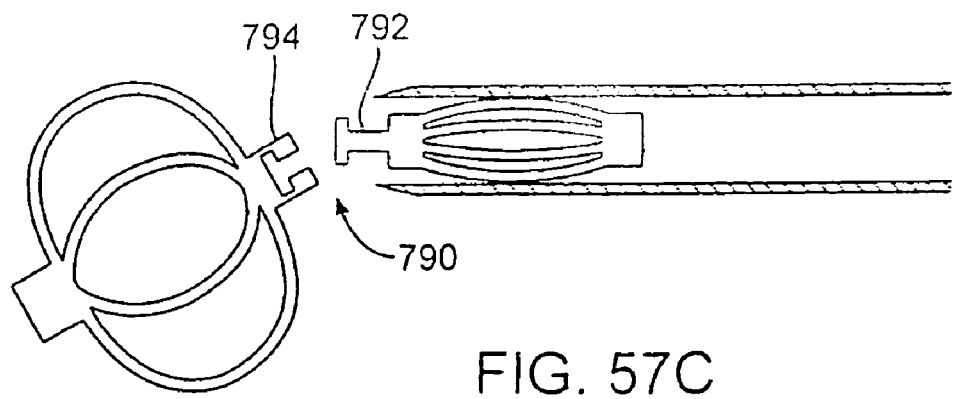
Figure 58A:
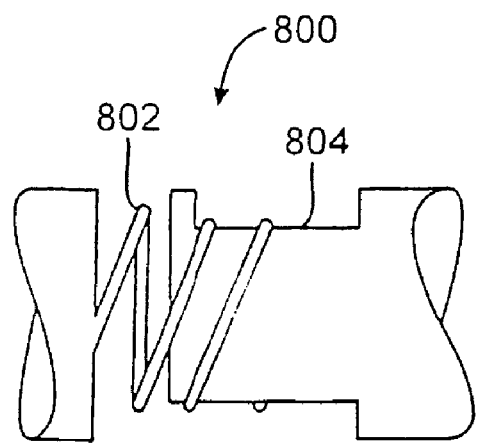
FIGS. 58A to 58C show a rotational coil locking feature variation which may be utilized in deploying one or more anchors.
Figure 58B:
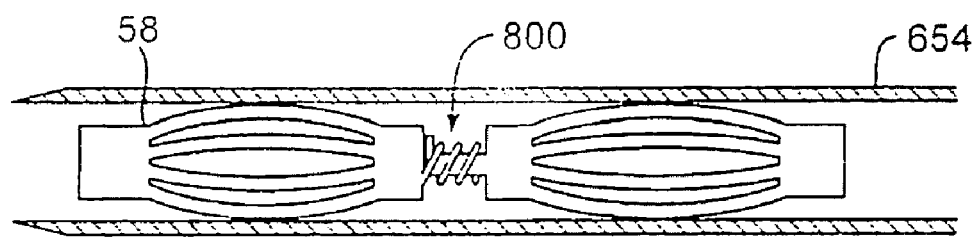
Figure 58C:
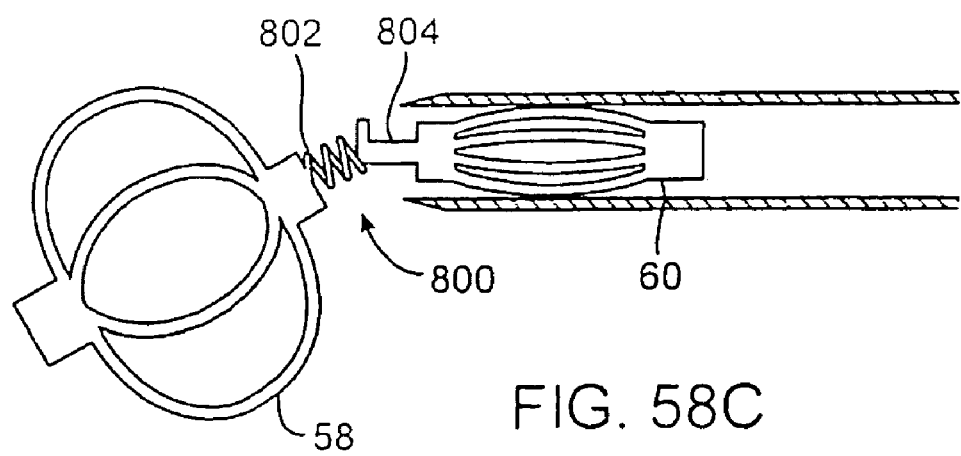

FIGS. 56A, 56B, and 56C likewise show interlocking feature 780 having a tab 782 and a complementary receiving groove 784 in a detail view, between adjacent anchors, and with distal anchor 58 being released from the interlocking feature 780, respectively. FIGS. 57A, 57B, and 57C likewise show interlocking feature 790 having a pin 792 and a complementary receiving groove 794 in a detail view, between adjacent anchors, and with distal anchor 58 being released from the interlocking feature 790, respectively. FIGS. 58A, 58B, and 58C likewise show rotational interlocking feature 800 having a helix or coil 802 and a complementary inter-fitting pin 804 in a detail view, between adjacent anchors, and with distal anchor 58 being released from the interlocking feature 800, respectively.

Figure 59A:
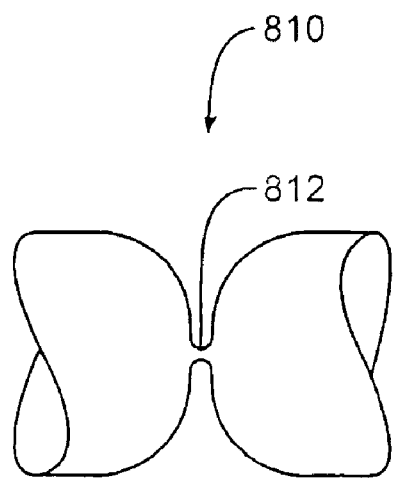
FIGS. 59A to 59C show an electrolytic joint locking feature variation which may be utilized in deploying one or more anchors.
Figure 59B:
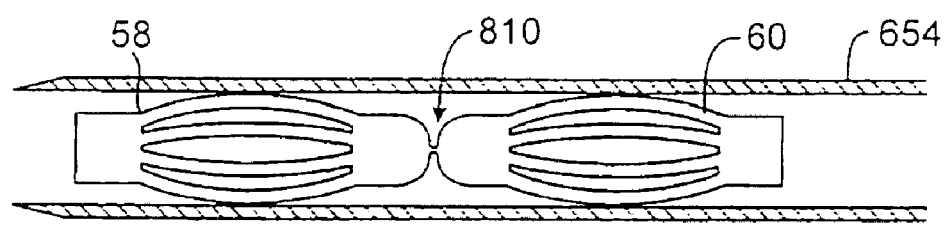
Figure 59C:
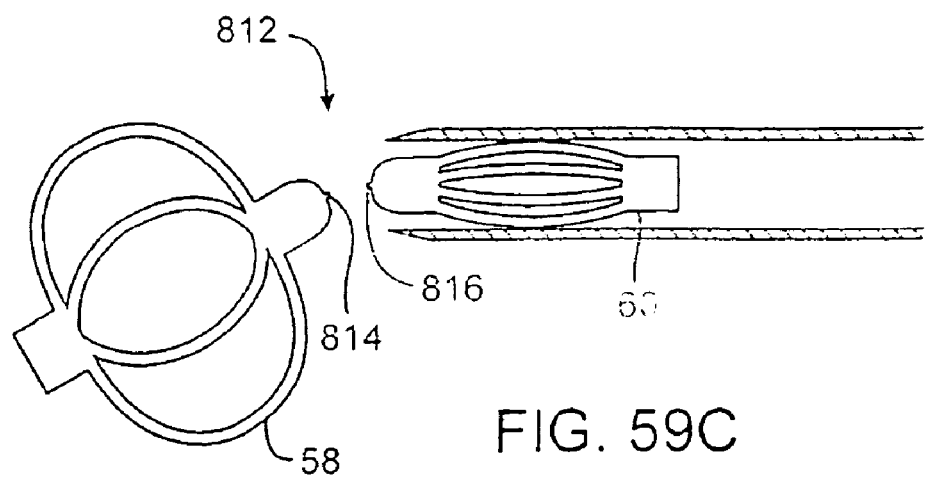

FIGS. 59A, 59B, and 59C likewise show electrolytic interlocking feature 810 having an inter-joined electrolytically-erodable joint 812 in a detail view, between adjacent anchors, and with distal anchor 58 being released from the interlocking feature 780, respectively. The electrolytically-erodable joint 812 may be electrically connected via wires (not shown) routed through sheath 654 to a power source located outside the patient. For release of the anchor, the electrolytically-erodable joint 812 may be eroded and leave eroded joint ends 814, 816 on adjacent anchors.

Figure 60A:
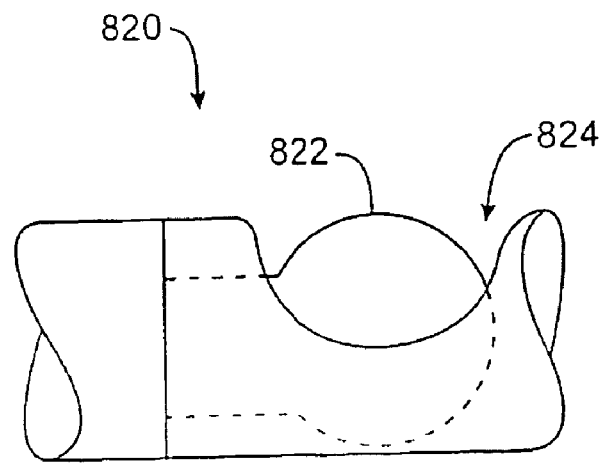
FIGS. 60A to 60C show a ball-groove locking feature variation which may be utilized in deploying one or more anchors.
Figure 60B:
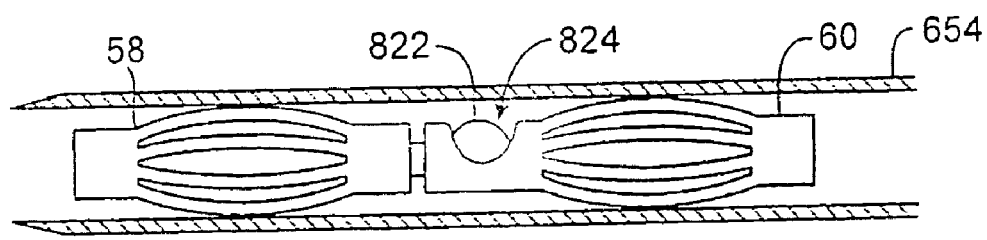
Figure 60C:
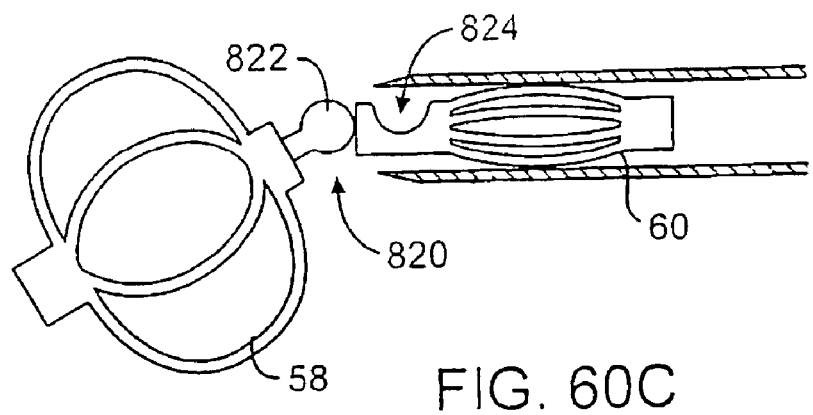

FIGS. 60A, 60B, and 60C likewise show interlocking feature 820 having a balled joint 822 and a complementary receiving groove 824 in a detail view, between adjacent anchors, and with distal anchor 58 being released from the interlocking feature 820, respectively.

Figure 61A:
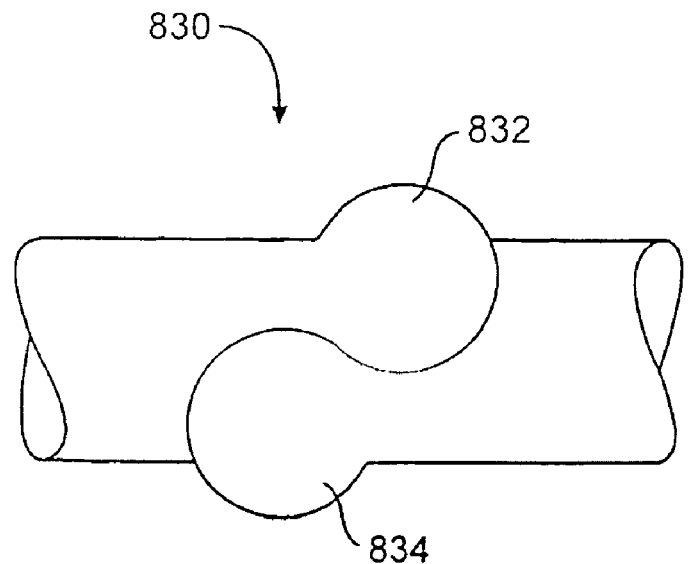
FIGS. 61A to 61C show a balled-joint locking feature variation which may be utilized in deploying one or more anchors.
Figure 61B:
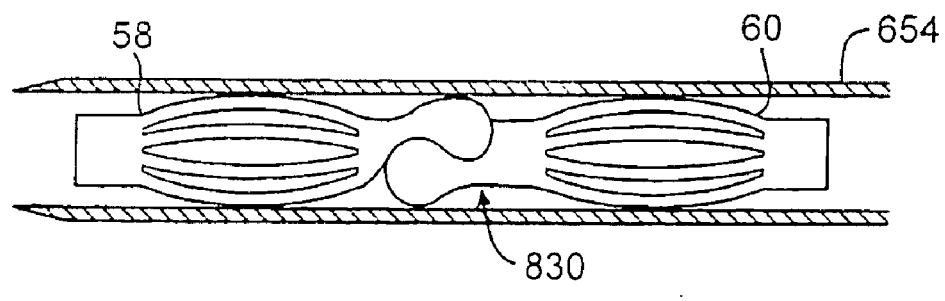
Figure 61C:
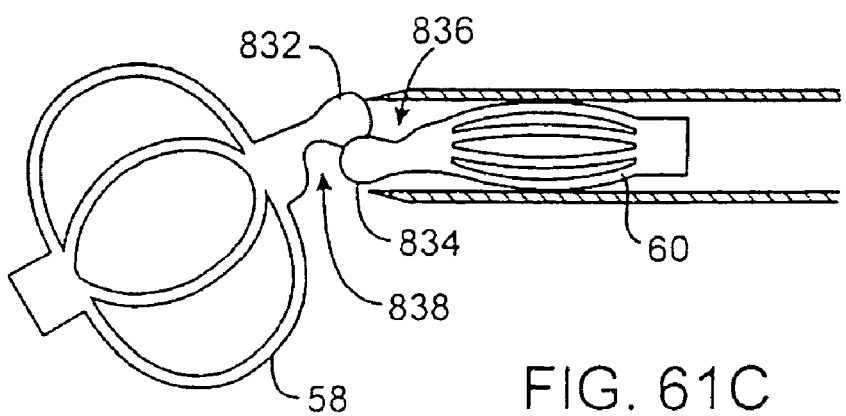

FIGS. 61A, 61B, and 61C likewise show balled interlocking feature 830 in a detail view, between adjacent anchors, and with distal anchor 58 being released from the interlocking feature 830, respectively. Each of the respective ball joints 832, 834 are configured to inter-fit with complementary receiving grooves 836, 838 on adjacent anchors.

Figure 62A:
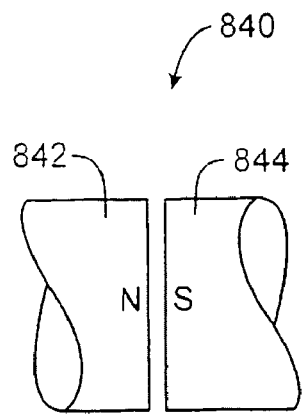
FIGS. 62A to 62C show a magnetic locking feature variation which may be utilized in deploying one or more anchors.
Figure 62B:
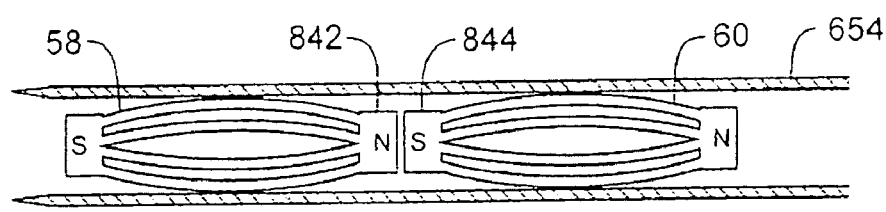
Figure 62C:
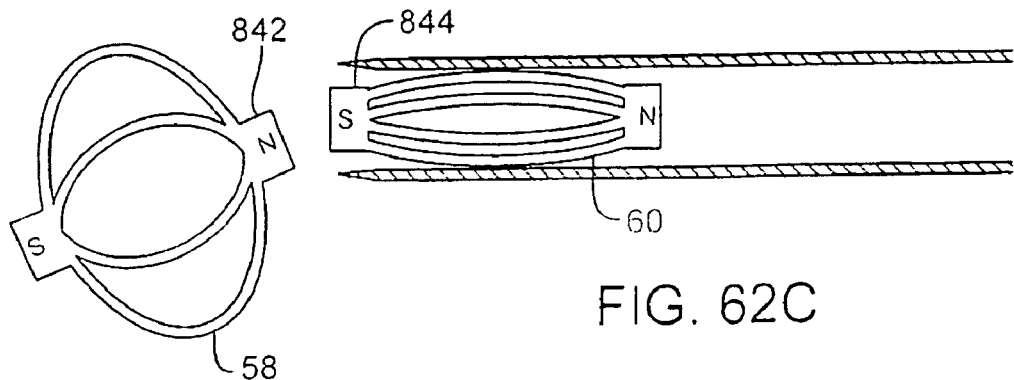

FIGS. 62A, 62B, and 62C likewise show magnetic locking feature 840 having respective anchors ends 842, 844 with opposing polarities in a detail view, between adjacent anchors, and with distal anchor 58 being released from the magnetic locking feature 840, respectively. Each of the magnets 842, 844 may be comprised of ferromagnetic materials, or they may be electromagnetically charged.

Figure 63:
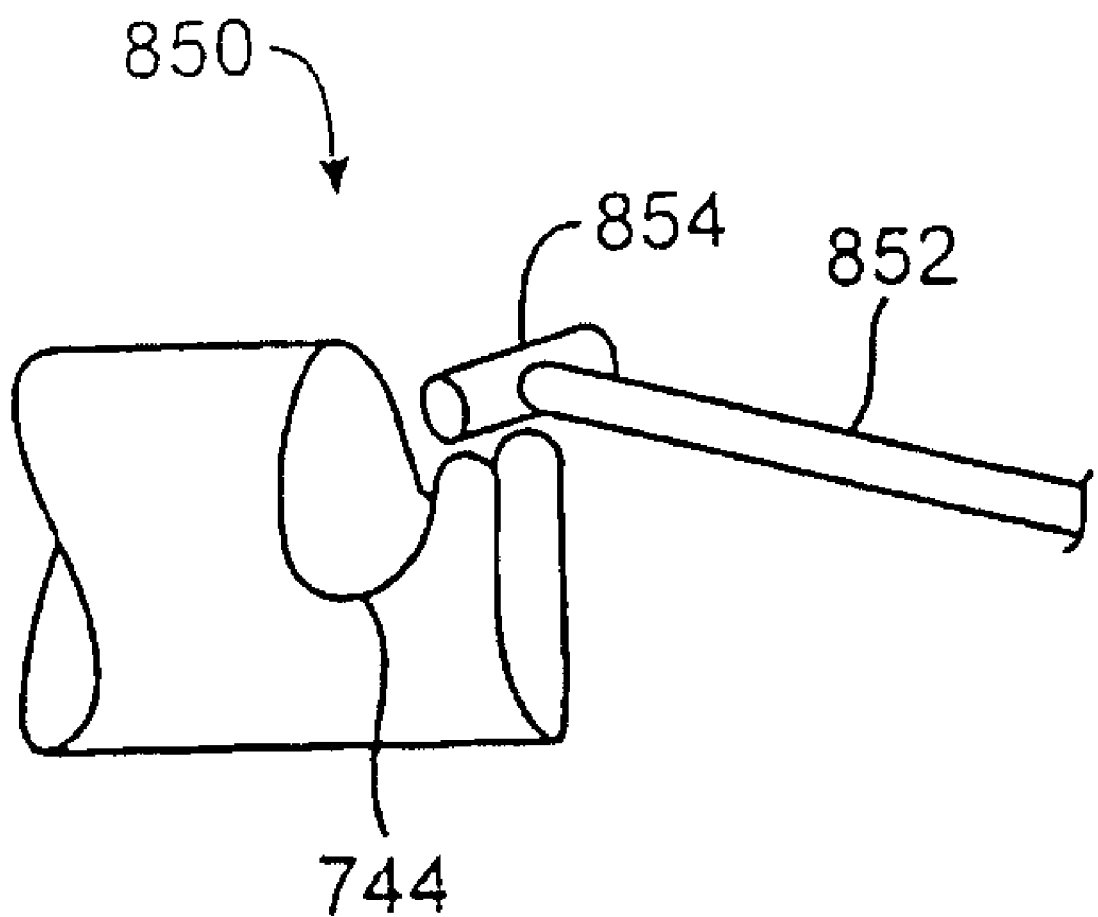
FIG. 63 shows a locking feature variation utilizing a cross-member.

FIG. 63 shows yet another variation which may be utilized particularly between an anchor and the elongate pusher. The interlocking feature 850 may comprise a curved or arcuate feature, e.g., circumferential-tab locking feature 744, which may receive a cross-member 854 extending perpendicularly from elongate member 852.

Figure 64A:
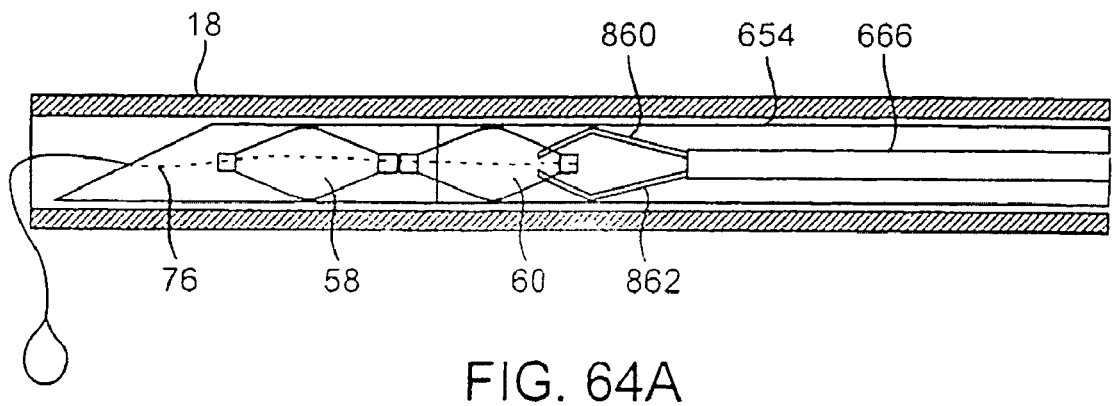
FIGS. 64A to 64C show various additional feature for controlling the deployment of anchors.

FIG. 64A shows yet another variation where elongate pusher 666 may have one or several biased retaining arms 860, 862 extending from the distal end of pusher 666. Retaining arms 860, 862 may be biased to extend radially but may be constrained to extend radially inward when positioned within sheath 654. The distal ends of arms 860, 862 may protrude inwardly between the struts of the anchor 60 for manipulation and deployment. When pusher 666 is advanced distally, arms 860, 862 may spring radially open to thereby release anchor 60. The proximal portions of arms 860, 862 may be tapered such that when pusher 666 is withdrawn proximally into sheath 654, the taper on each of the arms 860, 862 allows them to be drawn back into sheath 654.

Figure 64B:
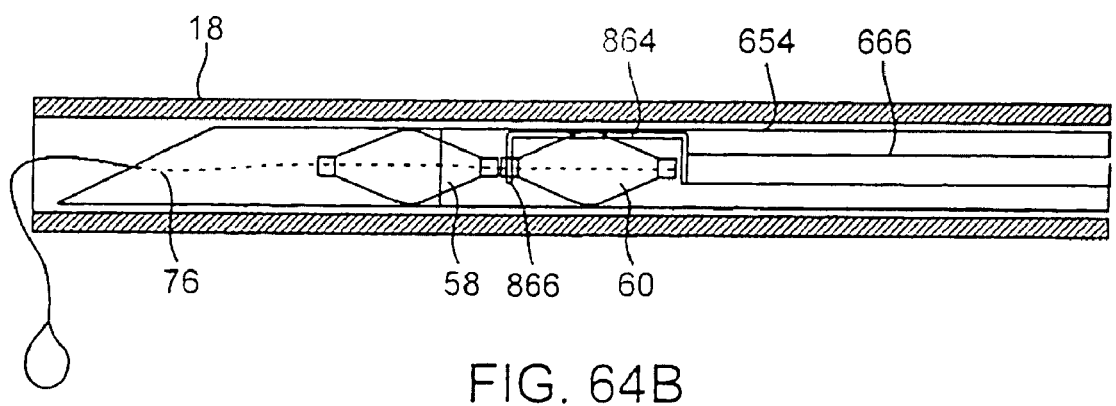

FIG. 64B shows another variation in which extension member 864 may extend distally from elongate pusher 666 to form at least one retaining arm 866 which may extend between one or more adjacent anchors 58, 60. As pusher 666 is advanced distally, proximal anchor 60 may be released when retaining arm 866 is fully advanced outside of sheath 654 and needle body 662.

Figure 64C:
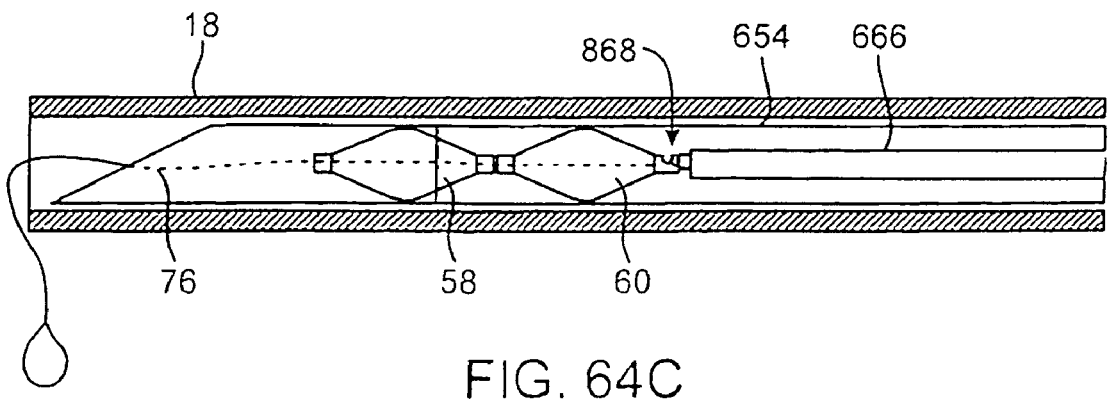

FIG. 64C shows yet another variation where the proximal anchor 60 may be retained to pusher 666 via a looped member 868 extending from the distal end of pusher 666. Looped member 868 may simply be looped about the proximal end of proximal anchor 60 and released by simply advancing anchor 60 out of sheath 654.

Figure 65:
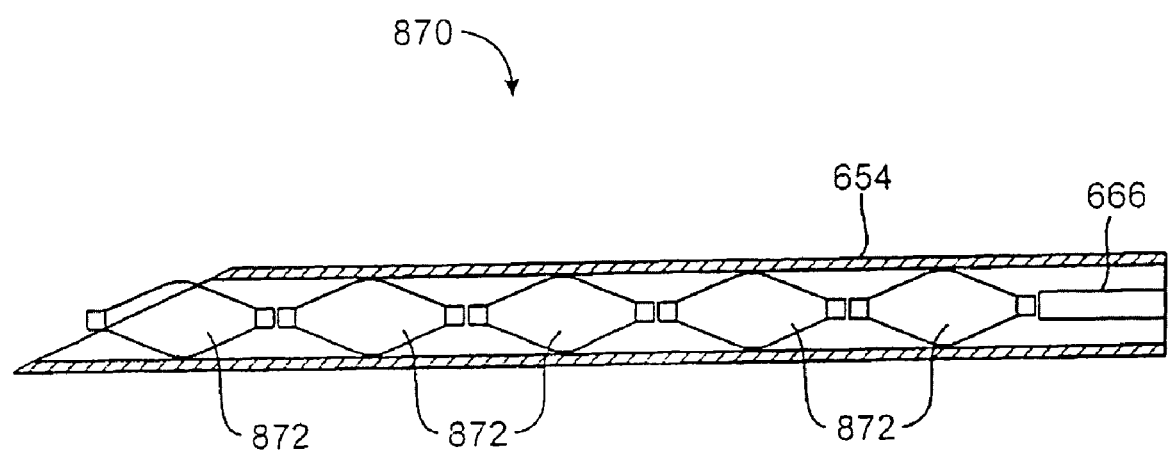
FIG. 65 shows a variation for deploying multiple anchors adjacently aligned within a single needle assembly.

In utilizing any of the interlocking features described herein, needle assemblies may be utilized having multiple anchors for deployment into or through tissue. FIG. 65 shows a partial cross-sectional view of multi-anchor variation 870 in which multiple anchors 872 may be aligned adjacently to one another in series within the sheath 654. Each of the anchors 872 may be temporarily interlocked with one another such that each anchor 872 may be deployed sequentially in a controlled manner.

Figure 66A:
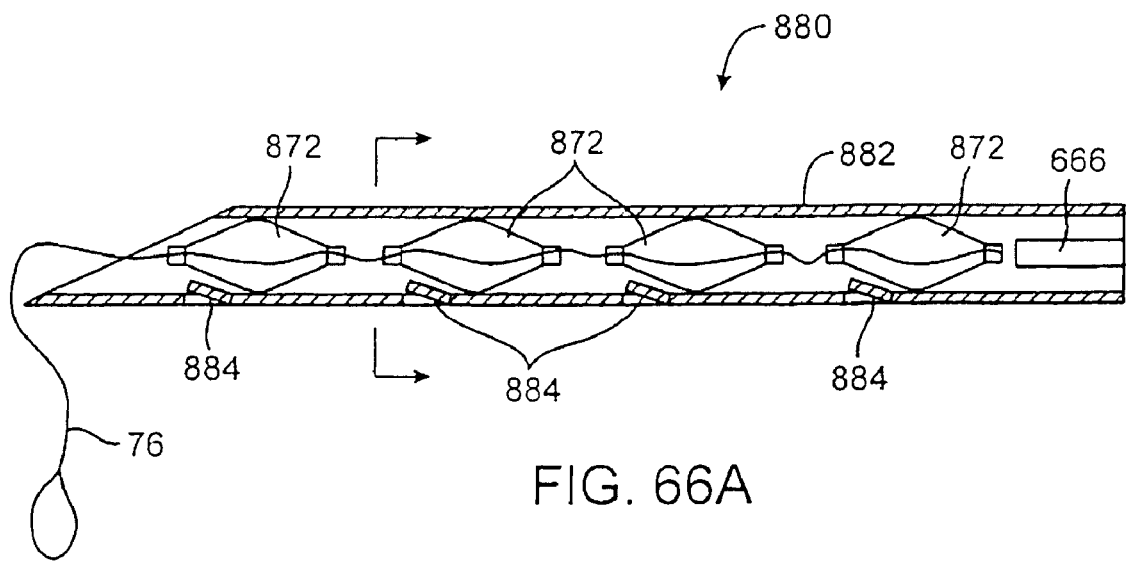
FIGS. 66A to 66C show partial cross-sectional side, bottom, and end views, respectively, of another variation for deploying multiple anchors in a controlled manner via corresponding retaining tabs.
Figure 66B:
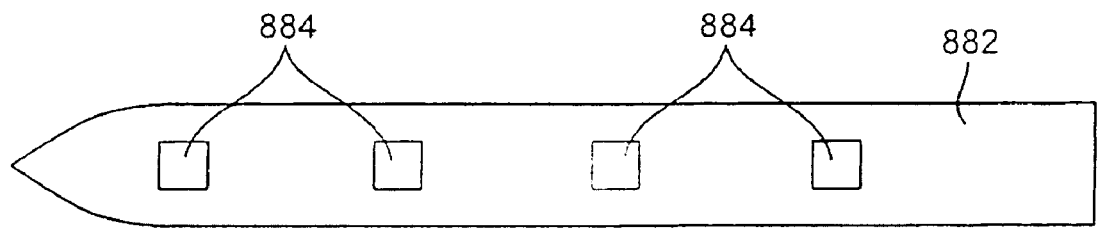
Figure 66C:
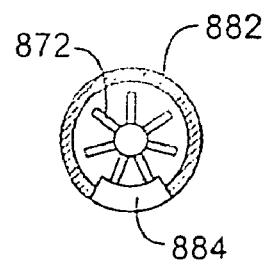

FIGS. 66A and 66B show partial cross-sectional side and bottom views of yet another multi-anchor variation 880. In this variation, sheath 882 may comprise a multi-tabbed assembly having multiple retaining tabs 884 extending partially into the sheath lumen. Each of the tabs 884 may be spaced uniformly relative to one another such that a single anchor 872 may be retained by a single tab 884, as shown in the FIG. 66A. As pusher 666 advances distally, each of the anchors, with or without interlocking features between adjacent anchors, may be advanced past a tab 884 until the desired number of anchors 872 has been deployed. Each tab 884 is preferably configured to extend only partially into the lumen, as mentioned and as shown in the cross-sectional view of FIG. 66C, and is preferably configured to flex and thereby allow for passage of an anchor 872.

Although a number of illustrative variations are described above, it will be apparent to those skilled in the art that various changes and modifications may be made thereto without departing from the scope of the invention. Moreover, although specific configurations and applications may be shown, it is intended that the various features may be utilized in various types of procedures in various combinations as practicable. It is intended in the appended claims to cover all such changes and modifications that fall within the true spirit and scope of the invention.

We claim:

1. An apparatus for forming a tissue fold, comprising:
   an elongate member having a proximal end, a distal end, and a length therebetween;
   a first stabilizing member and a second stabilizing member pivotably attached near or at the distal end of the elongate member and adapted to stabilize tissue therebetween;
   an engagement member movably positioned at or near the distal end of the elongate member and adapted to engage the tissue thereto; and
   a delivery tube pivotably attached directly to a distal end of said first stabilizing member and adapted to be positioned substantially transversely to the tissue.

2. The apparatus of claim 1 further comprising a needle assembly slidably disposed within the delivery tube.

3. The apparatus of claim 2 further comprising al least one expandable anchor slidably disposed within the needle assembly for securement against the tissue fold.

4. The apparatus of claim 1 wherein the elongate member comprises a flexible length.

5. The apparatus of claim 4 wherein the flexible length is adapted to be advanced through an endoscopic device.

6. The apparatus of claim 5 wherein the endoscopic device comprises a shape-lockable endoscopic body.

7. The apparatus of claim 5 wherein the endoscopic device is steerable.

8. The apparatus of claim 1 wherein the distal end of the engagement member comprises a helically-wound member configured to pierce the tissue when rotated about its longitudinal axis.

9. The apparatus of claim 1 wherein the second stabilizing member is pivotable relative to the first stabilizing member.

10. The apparatus of claim 1 wherein the delivery tube is articulatable between a low-profile configuration and a pivoted launch configuration.

11. An apparatus for forming a tissue told, comprising:
    an elongate tubular member having a proximal end, a distal end, and a length therebetween;
    an engagement member having a distal end adapted to engage tissue;
    a first stabilizing member and a second stabilizing member positioned at the tubular member distal end and adapted to stabilize tissue therebetween, wherein the first stabilizing member has a first position in which it is biased away from the second stabilizing member, and a second position in which it is moved toward the second stabilizing member relative to the first position; and a delivery tube attached directly to and adapted to pivot about the first stabilizing member.

12. The apparatus of claim 11 further comprising a needle assembly slidably disposed within the delivery tube.

13. The apparatus of claim 12 further comprising at least one expandable anchor slidably disposed within the needle assembly for securement against the tissue fold.

14. The apparatus of claim 11 wherein the elongate member comprises a flexible length.

15. The apparatus of claim 14 wherein the flexible length is adapted to be advanced through an endoscopic device.

16. The apparatus of claim 15 wherein the endoscopic device comprises a shape-lockable endoscopic body.

17. The apparatus of claim 15 wherein the endoscopic device is steerable.

18. The apparatus of claim 11 wherein the distal end of the engagement member comprises a helically-wound member configured to pierce the tissue when rotated about its longitudinal axis.

19. The apparatus of claim 11 wherein the second stabilizing member is pivotable relative to the first stabilizing member.

20. The apparatus of claim 11 wherein the delivery tube is articulatable between a low-profile configuration and a pivoted launch configuration.

21. An apparatus for forming a tissue fold, comprising:

an elongate tubular member having a proximal end, a distal end, and a flexible length therebetween;

an engagement member adapted to engage tissue and slidably disposed adjacent the tubular member;

a first stabilizing member and a second stabilizing member positioned at the tubular member distal end and adapted to stabilize tissue therebetween, wherein the first and second stabilizing members are further adapted to be angled relative to a longitudinal axis of the elongate tubular member;

a delivery tube having a distal end that is attached directly to and adapted to pivot about the first stabilizing member; and a needle assembly having a needle body slidably disposed within the delivery tube.

22. The apparatus of claim 21 further comprising at least one expandable anchor slidably disposed within the needle assembly for securement against the tissue fold.

23. The apparatus of claim 21 wherein the elongate member comprises a flexible length.

24. The apparatus of claim 23 wherein the flexible length is adapted to be advanced through an endoscopic device.

25. The apparatus of claim 24 wherein the endoscopic device comprises a shape-lockable endoscopic body.

26. The apparatus of claim 24 wherein the endoscopic device is steerable.

27. The apparatus of claim 21 wherein the distal end of the engagement member comprises a helically-wound member configured to pierce the tissue when rotated about its longitudinal axis.

28. The apparatus of claim 21 wherein the second stabilizing member is pivotable relative to the first stabilizing member.

29. The apparatus of claim 21 wherein the delivery tube is articulatable between a low-profile configuration and a pivoted launch configuration.

* * * * *